US006454706B1

(12) United States Patent
Pullman

(10) Patent No.: US 6,454,706 B1
(45) Date of Patent: Sep. 24, 2002

(54) SYSTEM AND METHOD FOR CLINICALLY ASSESSING MOTOR FUNCTION

(75) Inventor: Seth L. Pullman, Scarsdale, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/517,845

(22) Filed: Mar. 2, 2000

(51) Int. Cl.$^7$ ............................. A61B 5/00; A61B 5/103
(52) U.S. Cl. ......................................... 600/300; 600/595
(58) Field of Search ............................... 600/595, 300; 128/897, 898, 923–925

(56) References Cited

U.S. PATENT DOCUMENTS 4,922,925 A * 5/1990 Crandall et al. ............ 128/782
5,772,611 A * 6/1998 Hocherman .................. 600/595
5,885,231 A * 3/1999 Cramer et al. ............... 600/595

OTHER PUBLICATIONS

Elble, R.J. et al, "Quantification of Essential Tremor in Writing and Drawing", Movement Disorders, vol. 11 No. 1, pp. 70–78, 1996.*

Blyler CR, Maher BA, Manschreck TC, Fenton WS. Line drawing as a possible measure of lateralized motor performance in schizophrenia. Schizophr Res Jul. 25, 1997;26(1): 15–23.

Filipová M, Filip V, Macek Z, Müllerová J, Káš S, Žižková B, Křivka J. Votavová M, Krejčová H. Terguride in parkinsonism. A multicenter trial. Eur Arch Psychiatry Neurol Sci 1988; 237(5):298–303.

Rice GP, Lesaux J, Vandervoort P, Macewan L, Ebers GC. Ondansetron, a 5–HT3 antagonist, improves cerebellar tremor. J Neurol Neurosurg Psychiatry 1997 Mar;62(3):282–284.

Wissel J, Kabus C, Wenzel R, Klepsch S, Schwarz U, Nebe A, Schelosky L, Scholz U, Poewe W. Botulinum toxin in writer's cramp: objective response evaluation in 31 patients. J Neurol Neurosurg Psychiatry Aug. 1996;61(2):172–17.

Eichhron TE, Gasser T, Mai N, Marquardt C, Arnold G, Schwarz J, Oertel WH. Computational Analysis of open loop handwriting movements in Parkinson's disease: a rapid method to detect dopamimetic effects. Mov Disord May 1996:11(3):289–297.

Lang, ALT, Fahn S. Assessment of Parkinson's Disease. In "Quantification of Neurologic Deficit." Munsat ed., 1989. Butterworth–Heinemann: Storeham, MA. Pp. 285–309.

Simpson GM, Angus JWS. A rating scale for extrapyramidal side effects. Acta Pyschiatr Scand 1970;212 (Suppl.):11–19.

Slavin MJ, Phillips JG, Bradshaw JL, Hall KA, Presnell I. Consistency of handwriting movements in dementia of the Alzheimer's type: a comparison with Huntington's and Parkinson'diseases. J Int Neuropsychol Soc Jan. 1999;5(1):20–25.

(List continued on next page.)

*Primary Examiner*—Eric F. Winakur
*Assistant Examiner*—David McCrosky

(57) ABSTRACT

In particular, the present invention relates to a computerized system and method for clinically assessing motor function comprising correlating geometric indices, computed from digital information obtained from a geometric shape drawn by a subject to be evaluated, with a rating score derived using a "standard of reference" generated by one or more clinical expert. Interpretation is thereby rendered more objective and consistent. Furthermore, the test may be administered and interpreted by physicians who are not skilled or experienced in evaluating motor disorders, for example general practitioners or pediatricians who are not certified in the practice of neurology. The present invention therefore provides a means for evaluating persons early in the course of disease, and for screening patients for motor dysfunction or, in the case of children, disorders of motor development.

17 Claims, 35 Drawing Sheets

Microfiche Appendix Included
(2 Microfiche, 151 Pages)

OTHER PUBLICATIONS

Lange–Küttner C. Pressure, velocity, and time in speeded drawing of basic graphic patterns by young children. Percept Mot Skills Jun. 1998 ;86(3 Pt 2):1299–1310.

Singer Y, Tishby N. Dynamical encoding of cursive handwriting. Biol Cybern 1994;71(3):227–237.

Van Den Heuvel CE, van Galen GP, Teulings HL, van Gemmert AW. Axial pen force increases with processing demands in handwriting. Acta Psychol Nov. 1998 ;100(1–2):145–159.

Morasso P, Sanguineti V. Neurocomputing aspects in modelling cursive handwriting. Acta Psychol (Amst) Mar. 1993;82(1–3):213–235.

Pullman SL, Wang Y, Pedersen SF, Fahn S. Computerized spiral analysis in patients with movement disorders. Neurology 1995;45 (Suppl 4):A218 (abstract 208S).

Yu QP, Pullman SL, Fahn S, Pedersen SF. Homonymous hemi–spiral abnormalities in patients with Parkinson's disease. Society for Neuroscience 1997;23:737.8 (abstract).

Yu Qp, Wen HP, Seltzer B, Pullman SL. Force–time residual and hemi–force characteristics in patients with Parkinson's disease and essential tremor. Society of Neuroscience 1998;24:672.2 (abstract).

* cited by examiner

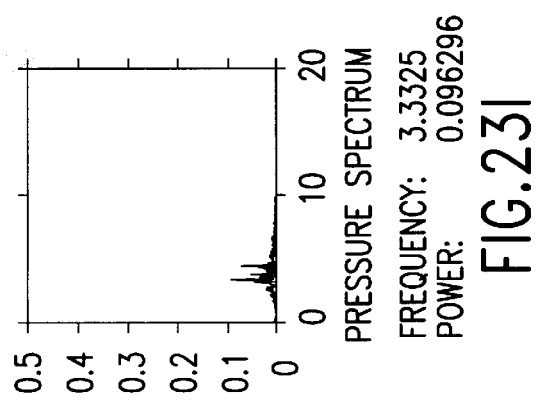
FREQUENCY: 0.73242
POWER: 0.0019174
X SPECTRUM
FIG.23G
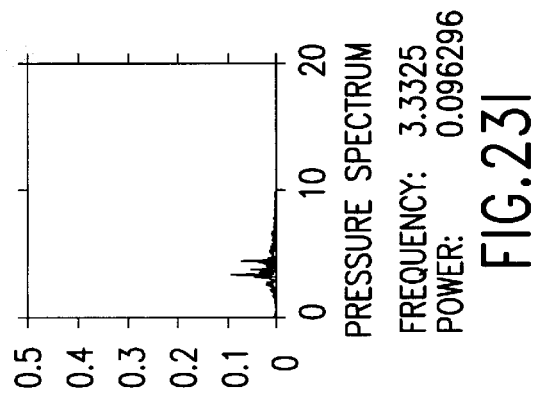
FREQUENCY: 0.71045
POWER: 0.00098593
Y SPECTRUM
FIG.23H
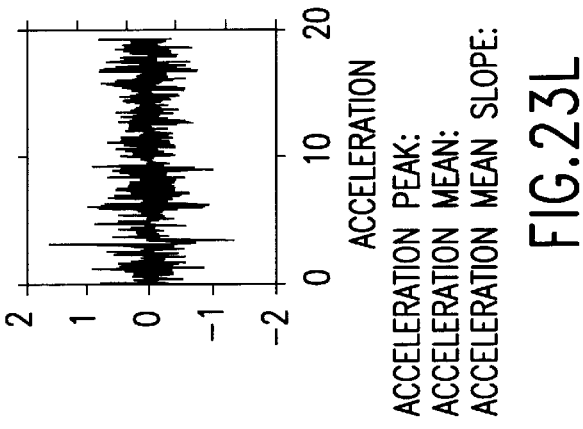
FREQUENCY: 3.3325
POWER: 0.096296
PRESSURE SPECTRUM
FIG.23I
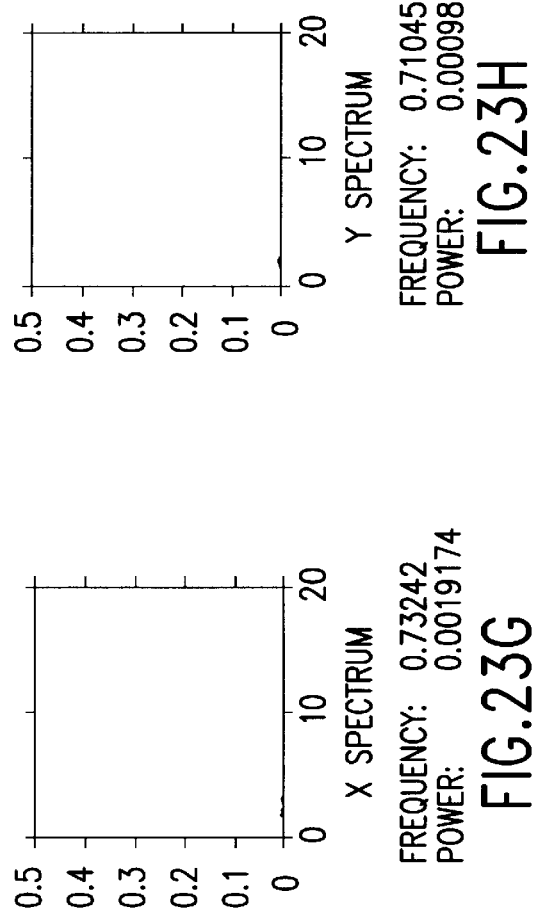
SPEED
FIG.23J
SPEED PEAK: 8.3495
SPEED MEAN: 4.0833
SPEED MEAN SLOPE: 0.007768
FREQUENCY: 0.21973
POWER: 0.051075
SPEED SPECTRUM
FIG.23K
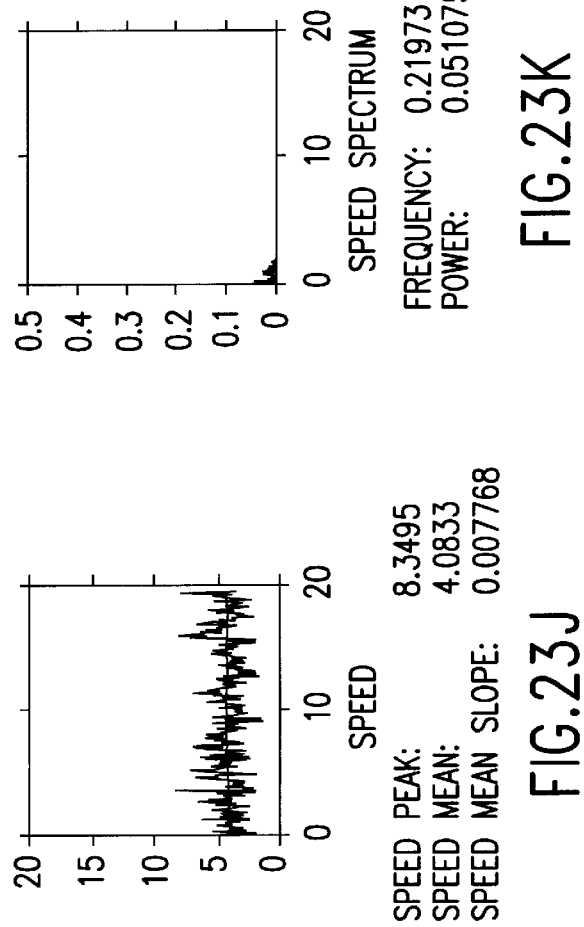
ACCELERATION
FIG.23L
ACCELERATION PEAK: 1.6081
ACCELERATION MEAN: 0.0032186
ACCELERATION MEAN SLOPE: 5.6582e−05

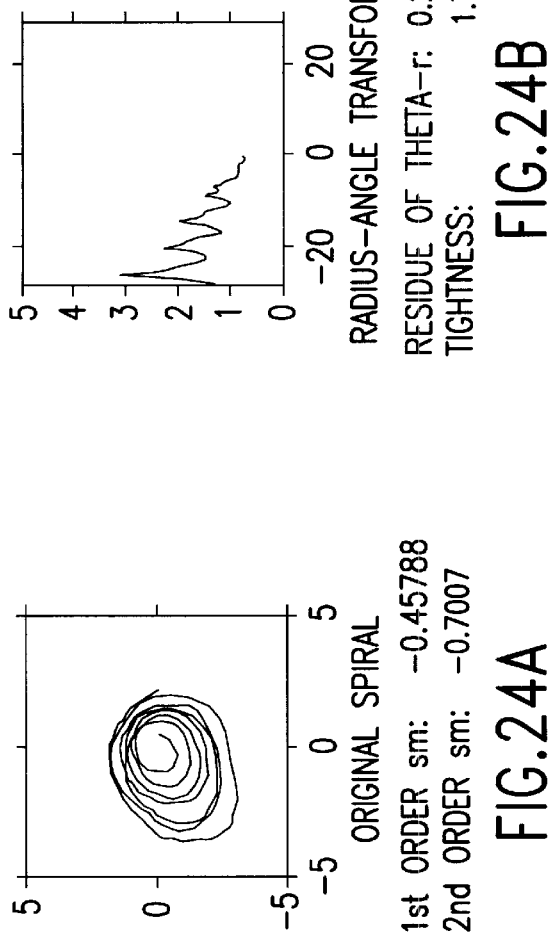
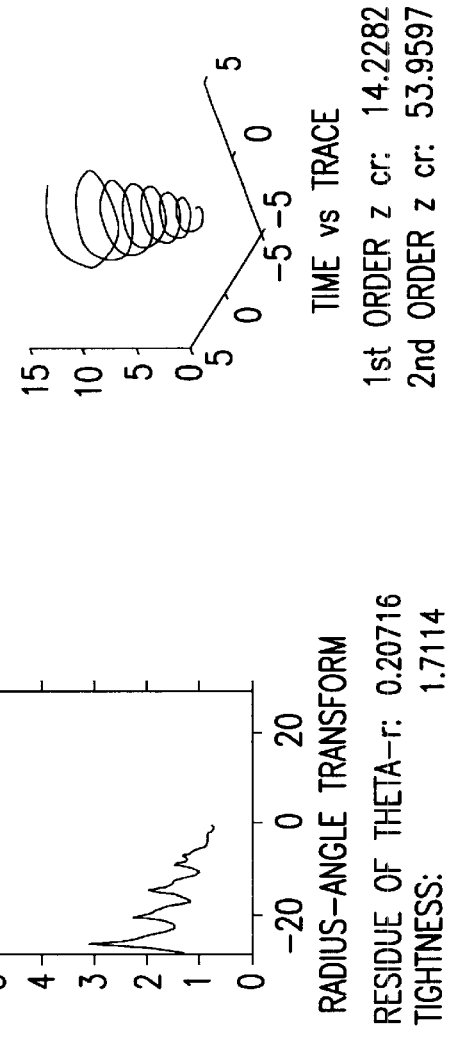
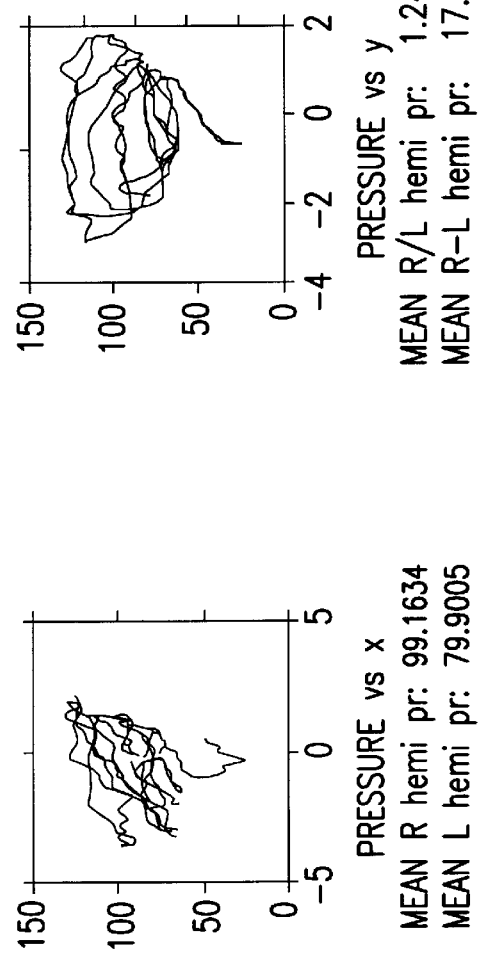
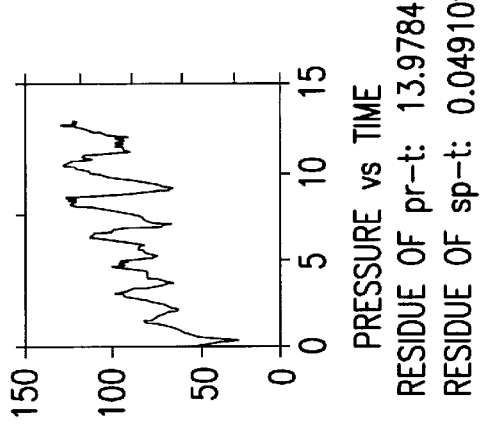
FIG.24A FIG.24B FIG.24C FIG.24D FIG.24E FIG.24F

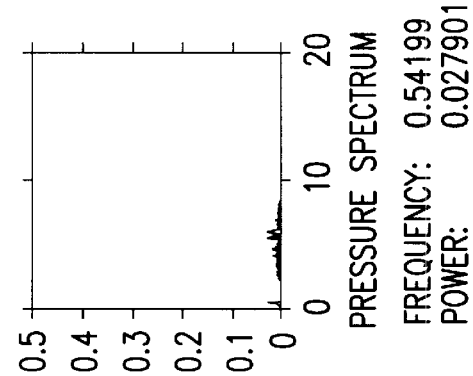
FIG.24G — X SPECTRUM
FREQUENCY: 1.18650
POWER: 0.00081621
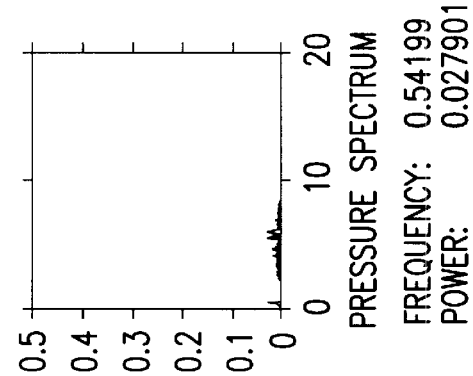
FIG.24H — Y SPECTRUM
FREQUENCY: 062988
POWER: 0.00053581
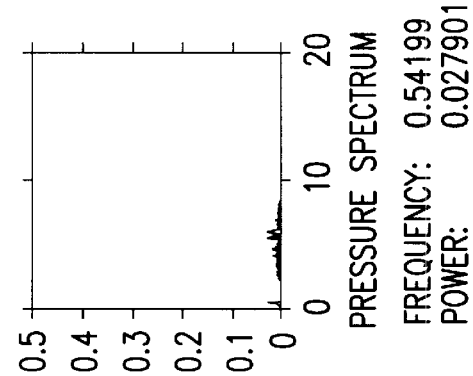
FIG.24I — PRESSURE SPECTRUM
FREQUENCY: 0.54199
POWER: 0.027901
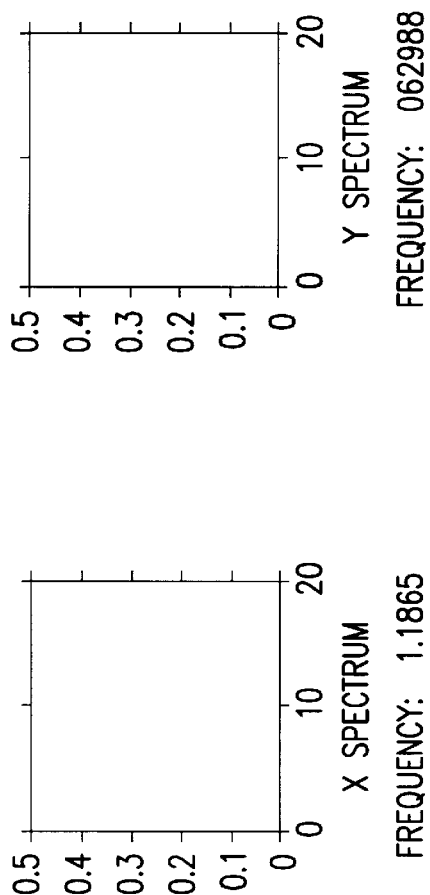
FIG.24J — SPEED
SPEED PEAK: 15.0426
SPEED MEAN: 6.0457
SPEED MEAN SLOPE: 0.1517
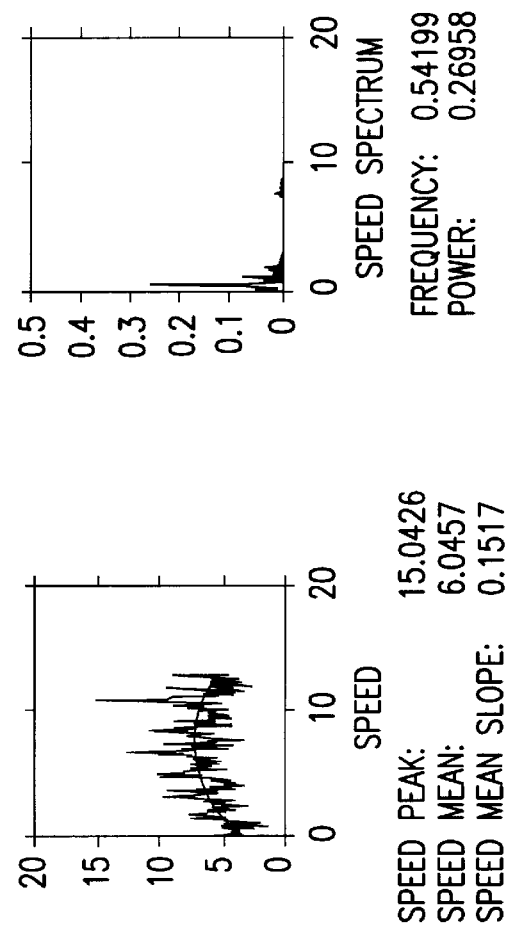
FIG.24K — SPEED SPECTRUM
FREQUENCY: 0.54199
POWER: 0.26958
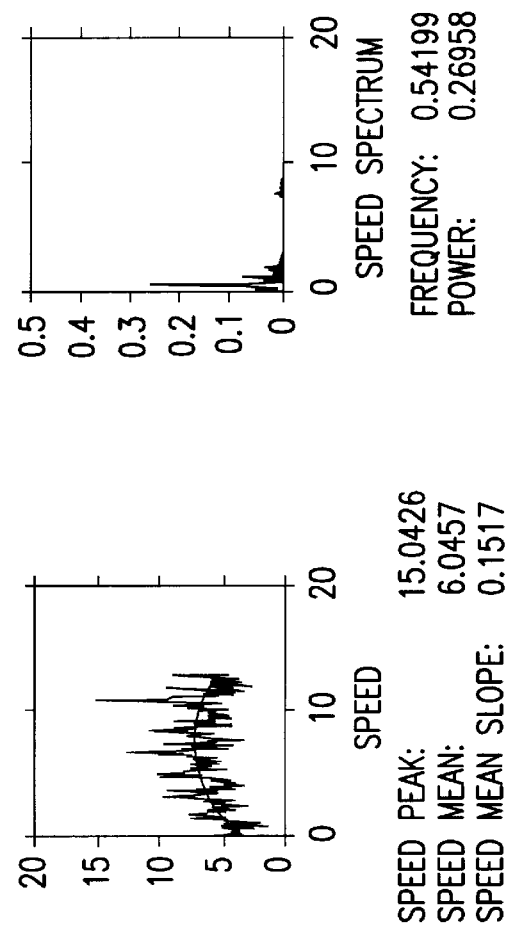
FIG.24L — ACCELERATION
ACCELERATION PEAK: 1.4751
ACCELERATION MEAN: 0.0046835
ACCELERATION MEAN SLOPE: −0.001430

TIME vs TRACE
1st ORDER z cr: 11.9734
2nd ORDER z cr: 46.5632

RADIUS-ANGLE TRANSFORM
RESIDUE OF THETA-r: 0.74962
TIGHTNESS: 1.8641

ORIGINAL SPIRAL
1st ORDER sm: −0.042043
2nd ORDER sm: −1.388

PRESSURE vs TIME
RESIDUE OF pr-t: 12.6003
RESIDUE OF sp-t: 0.045247

PRESSURE vs y
MEAN R/L hemi pr: 1.1733
MEAN R−L hemi pr: 16.2855%

PRESSURE vs x
MEAN R hemi pr: 122.4027
MEAN L hemi pr: 104.3259

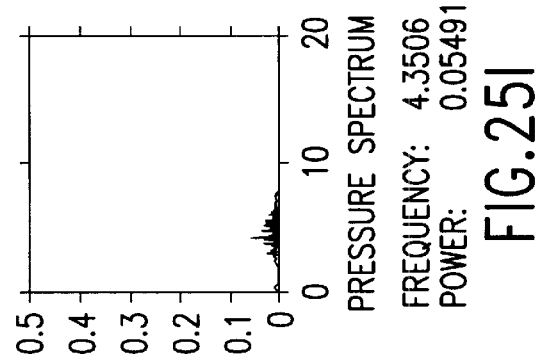
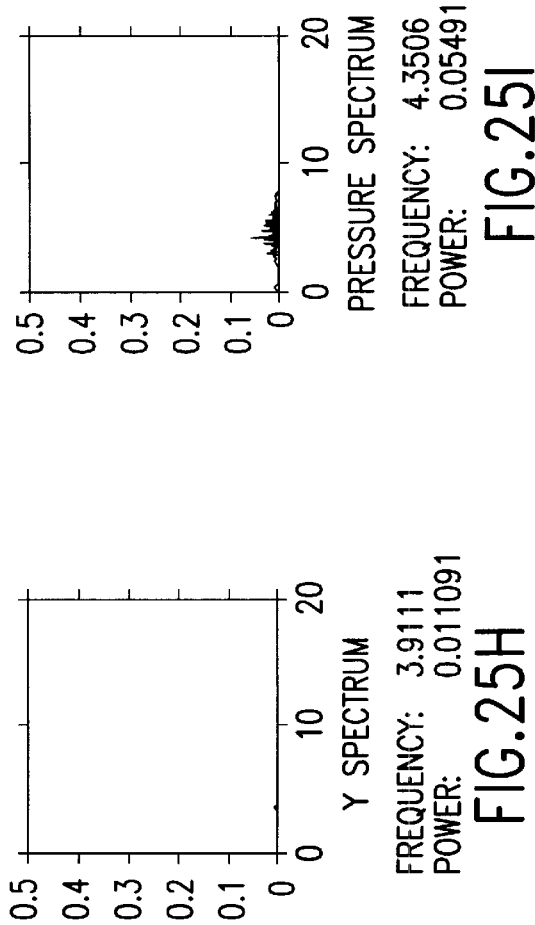
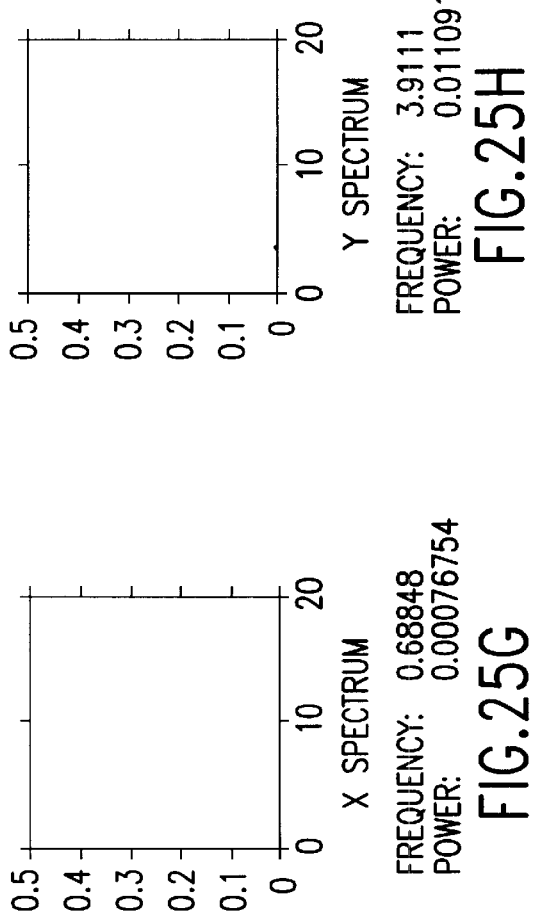
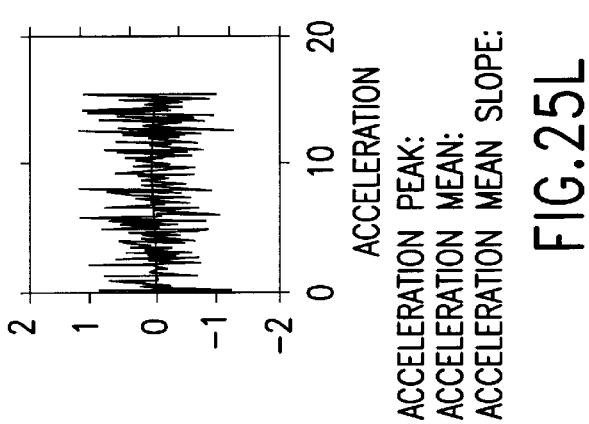
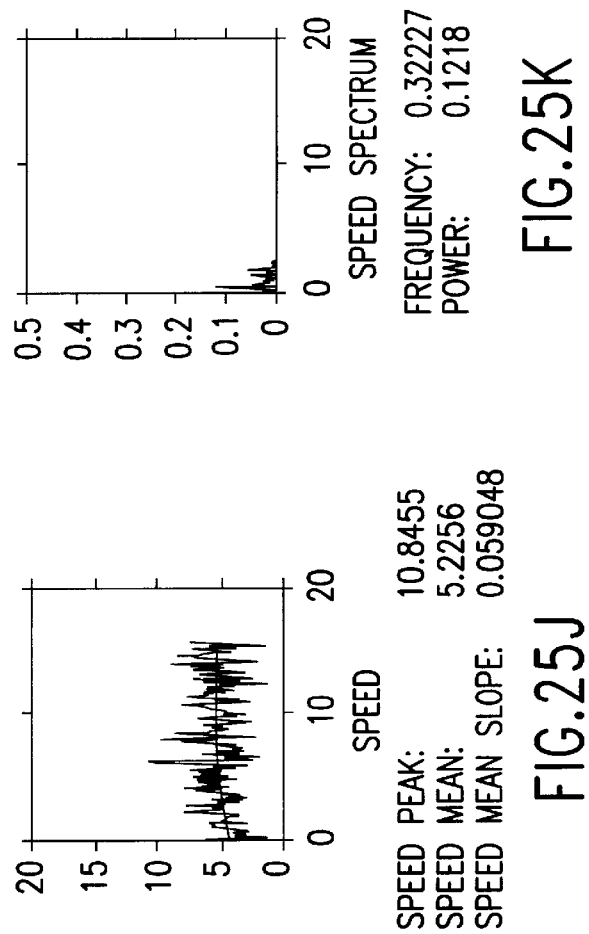

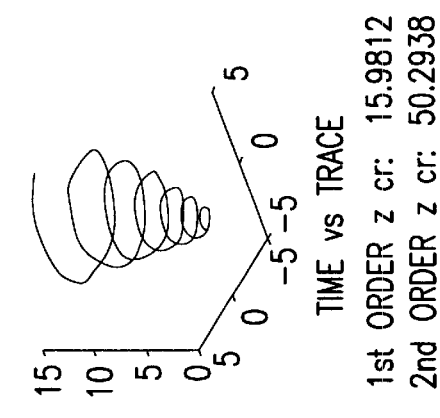
FIG.26C
TIME vs TRACE
1st ORDER z cr: 15.9812
2nd ORDER z cr: 50.2938
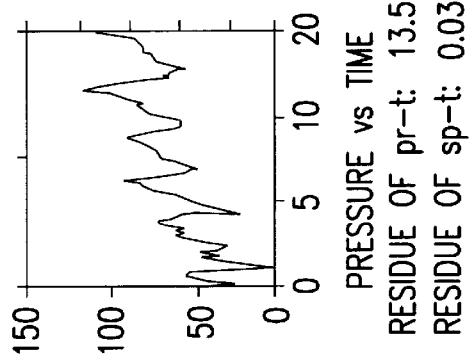
FIG.26F
PRESSURE vs TIME
RESIDUE OF pr-t: 13.5407
RESIDUE OF sp-t: 0.038145
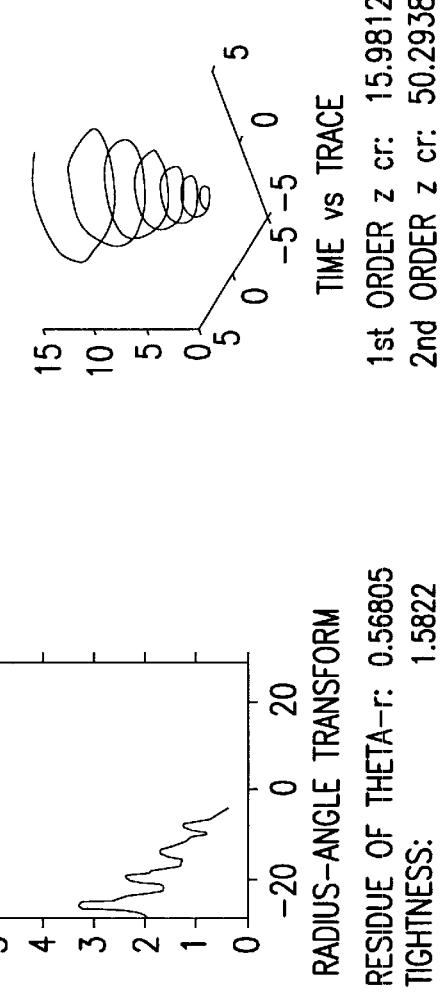
FIG.26B
RADIUS-ANGLE TRANSFORM
RESIDUE OF THETA-r: 0.56805
TIGHTNESS: 1.5822
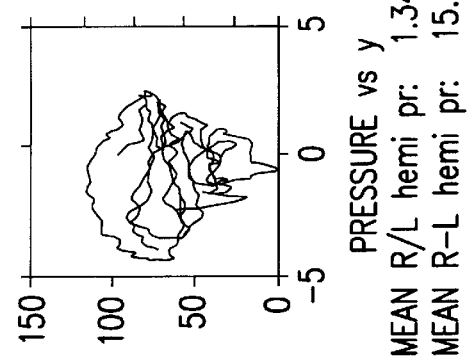
FIG.26E
PRESSURE vs y
MEAN R/L hemi pr: 1.3452
MEAN R-L hemi pr: 15.7708%
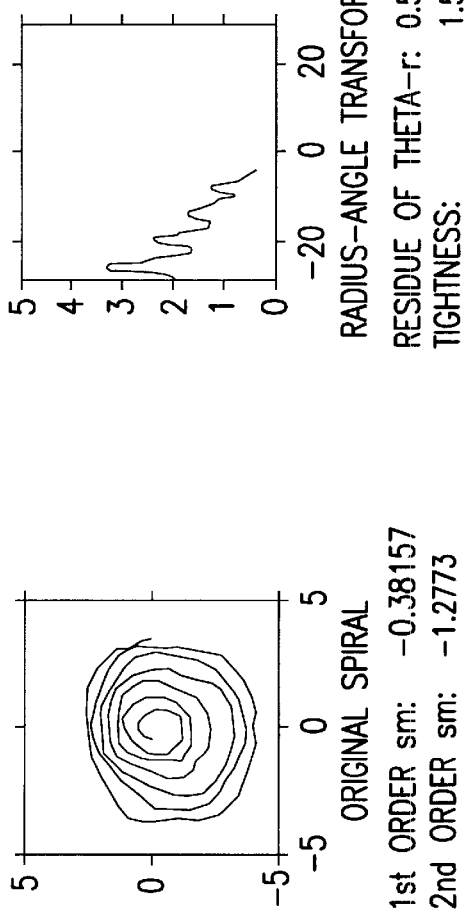
FIG.26A
ORIGINAL SPIRAL
1st ORDER sm: −0.38157
2nd ORDER sm: −1.2773
FIG.26D
PRESSURE vs x
MEAN R hemi pr: 72.5222
MEAN L hemi pr: 53.9127

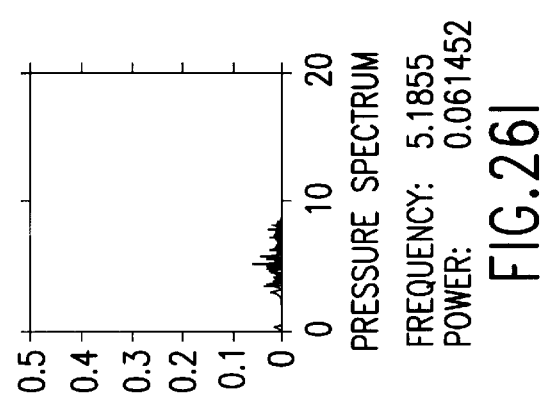
FIG. 26G — X SPECTRUM
FREQUENCY: 1.04
POWER: 0.00078855
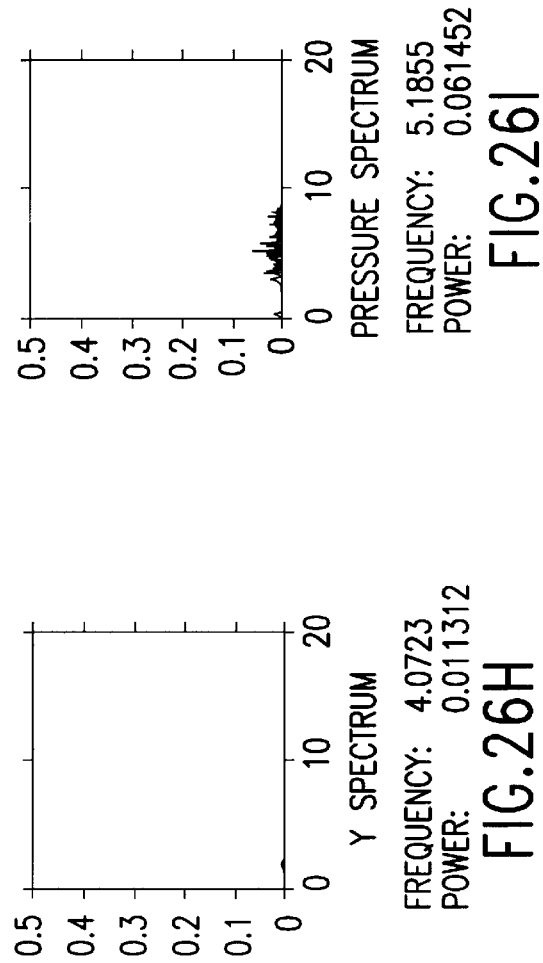
FIG. 26H — Y SPECTRUM
FREQUENCY: 4.0723
POWER: 0.011312
FIG. 26I — PRESSURE SPECTRUM
FREQUENCY: 5.1855
POWER: 0.061452
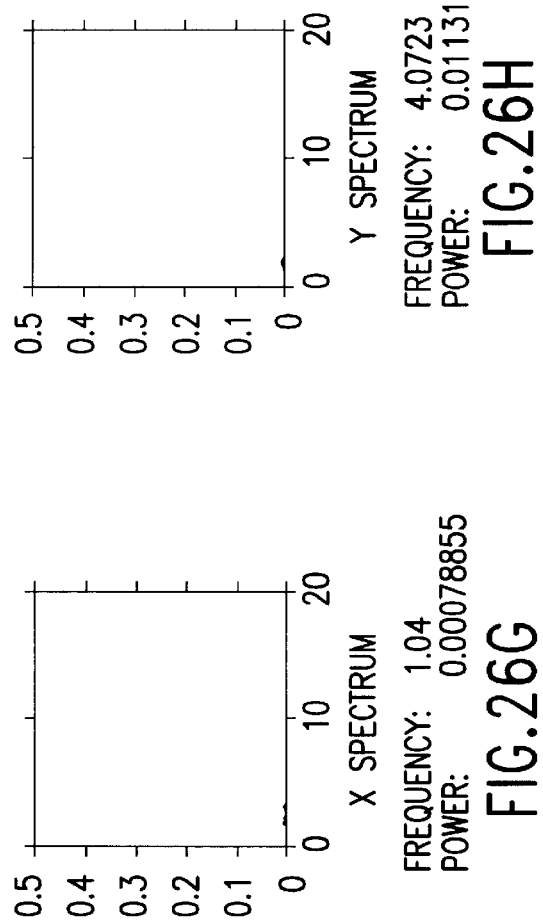
FIG. 26J — SPEED
SPEED PEAK: 9.9972
SPEED MEAN: 6.1496
SPEED MEAN SLOPE: 0.17253
FIG. 26K — SPEED SPECTRUM
FREQUENCY: 0.39551
POWER: 0.045468
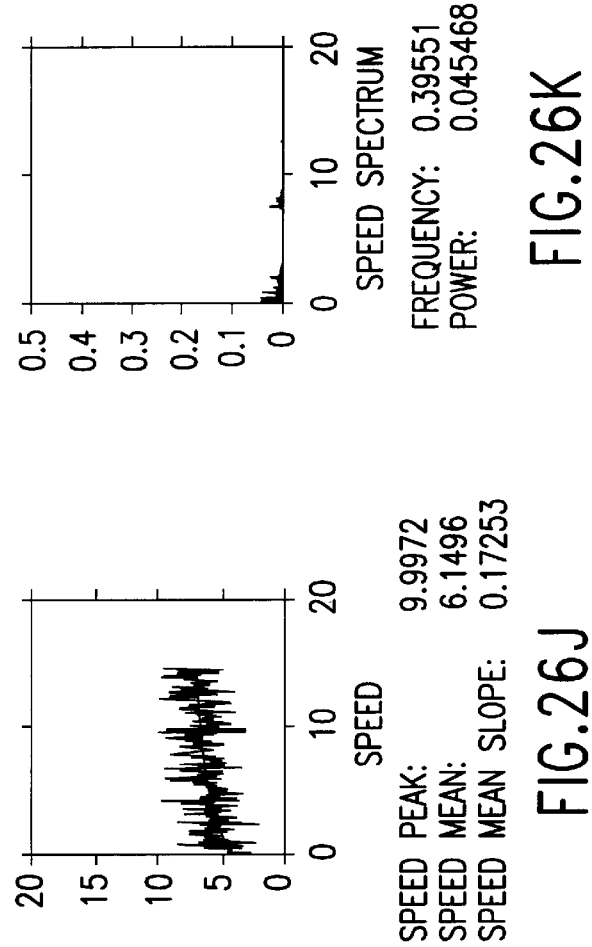
FIG. 26L — ACCELERATION
ACCELERATION PEAK: 1.5307
ACCELERATION MEAN: 0.0093746
ACCELERATION MEAN SLOPE: −0.0016213
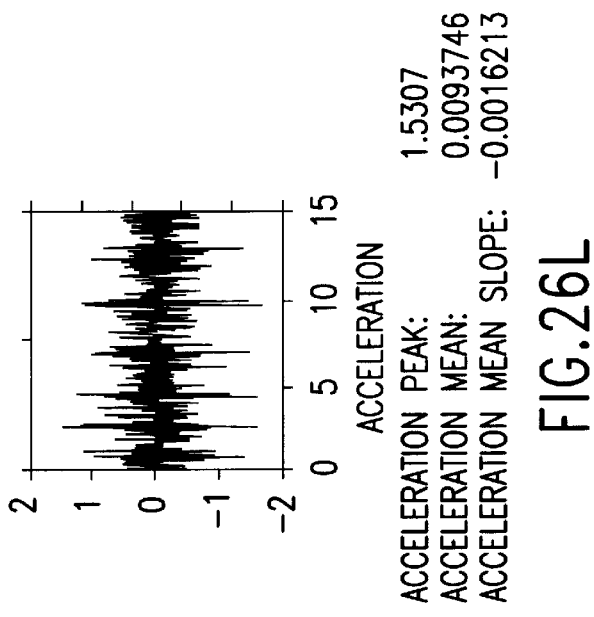

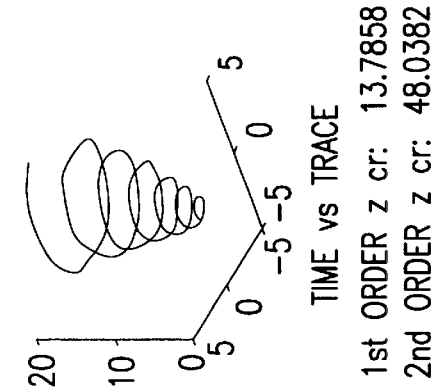
FIG.27C
TIME vs TRACE
1st ORDER z cr: 13.7858
2nd ORDER z cr: 48.0382
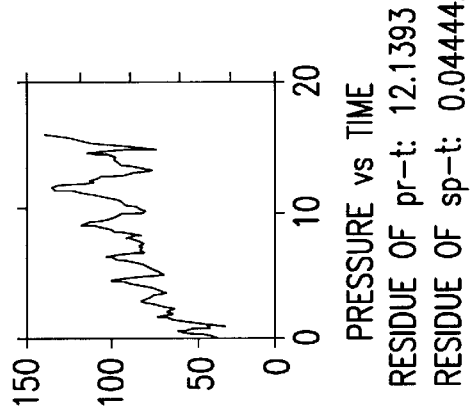
FIG.27F
PRESSURE vs TIME
RESIDUE OF pr-t: 12.1393
RESIDUE OF sp-t: 0.044442
FIG.27B
RADIUS-ANGLE TRANSFORM
RESIDUE OF THETA-r: 0.56693
TIGHTNESS: 1.9812
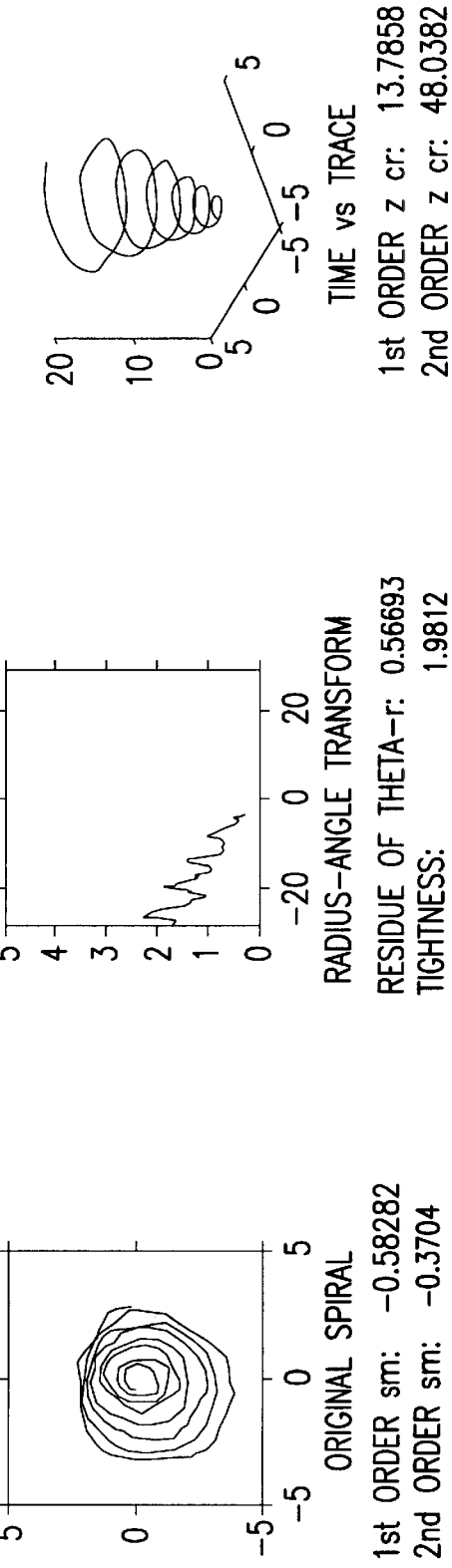
FIG.27E
PRESSURE vs y
MEAN R/L hemi pr: 1.212
MEAN R-L hemi pr: 15.39605%
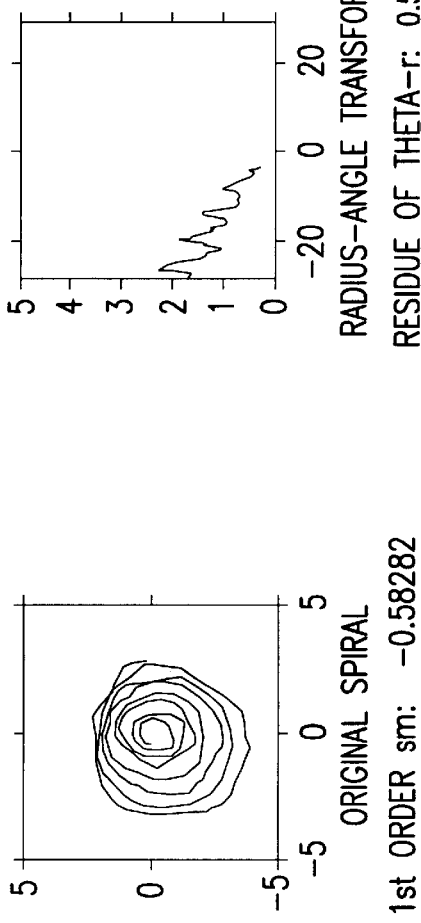
FIG.27A
ORIGINAL SPIRAL
1st ORDER sm: -0.58282
2nd ORDER sm: -0.3704
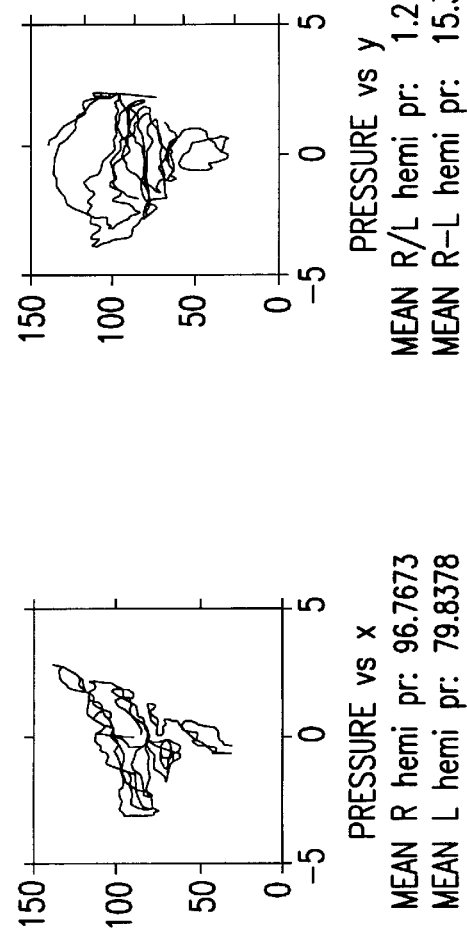
FIG.27D
PRESSURE vs x
MEAN R hemi pr: 96.7673
MEAN L hemi pr: 79.8378

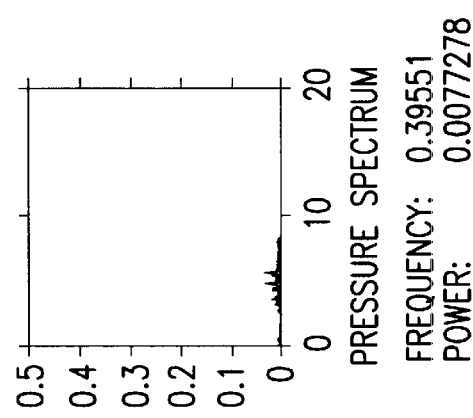
FIG.27G  X SPECTRUM
FREQUENCY: 0.98145
POWER: 0.00079653
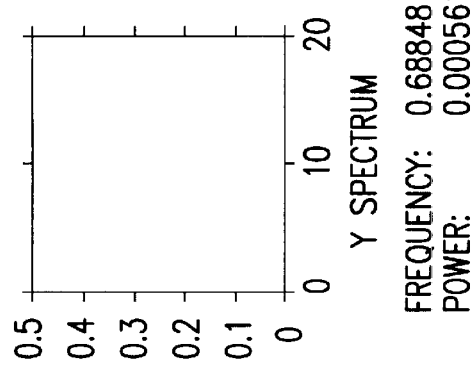
FIG.27H  Y SPECTRUM
FREQUENCY: 0.68848
POWER: 0.00056112
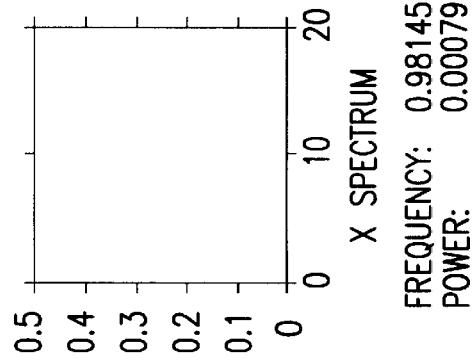
FIG.27I  PRESSURE SPECTRUM
FREQUENCY: 0.39551
POWER: 0.0077278
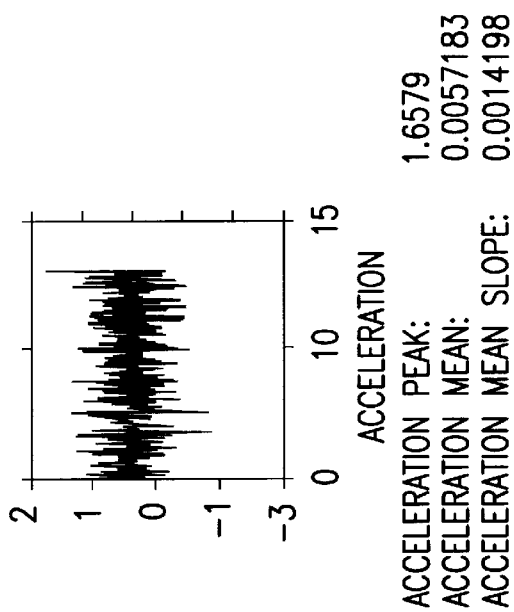
FIG.27J  SPEED
SPEED PEAK: 10.1037
SPEED MEAN: 5.272
SPEED MEAN SLOPE: −0.02886
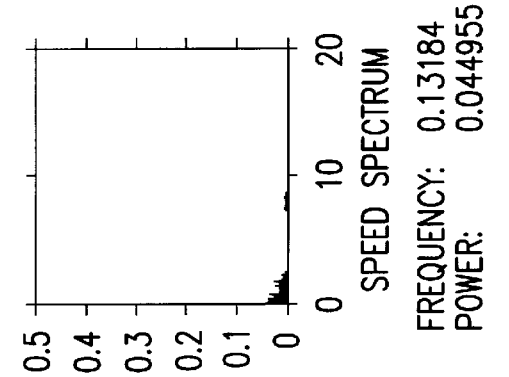
FIG.27K  SPEED SPECTRUM
FREQUENCY: 0.13184
POWER: 0.044955
FIG.27L  ACCELERATION
ACCELERATION PEAK: 1.6579
ACCELERATION MEAN: 0.0057183
ACCELERATION MEAN SLOPE: 0.0014198

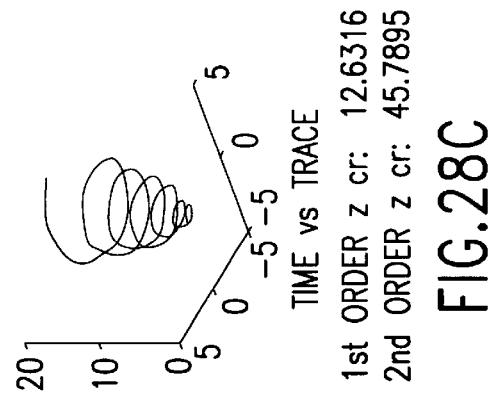
FIG.28C
TIME vs TRACE
1st ORDER z cr: 12.6316
2nd ORDER z cr: 45.7895
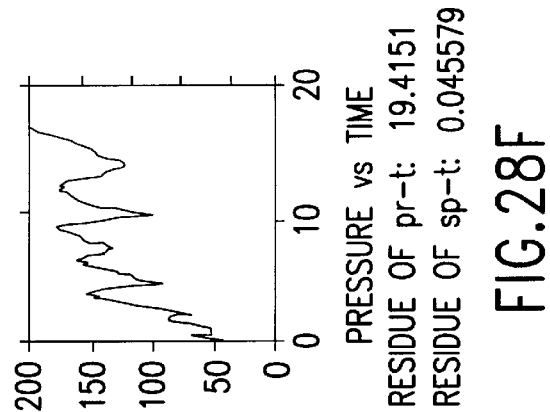
FIG.28F
PRESSURE vs TIME
RESIDUE OF pr-t: 19.4151
RESIDUE OF sp-t: 0.045579
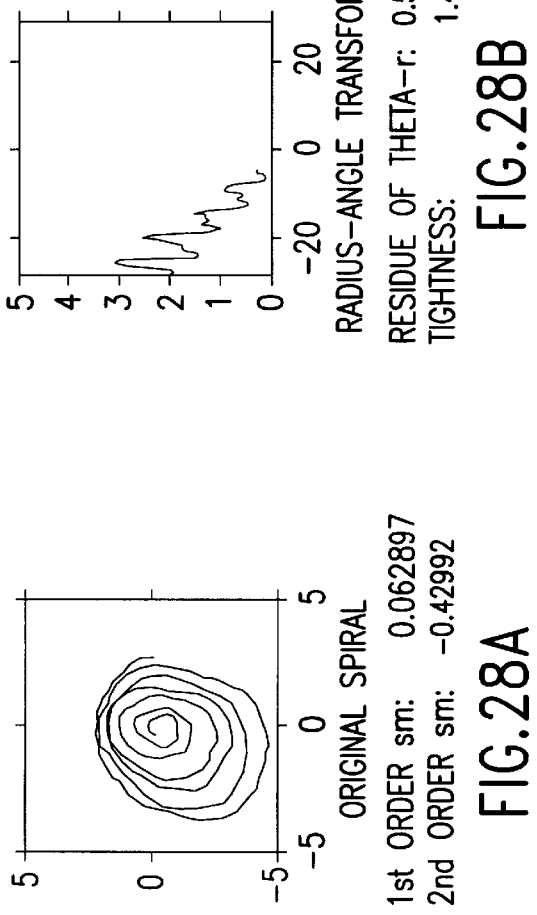
FIG.28B
RADIUS-ANGLE TRANSFORM
RESIDUE OF THETA-r: 0.53129
TIGHTNESS: 1.4456
FIG.28A
ORIGINAL SPIRAL
1st ORDER sm: 0.062897
2nd ORDER sm: -0.42992
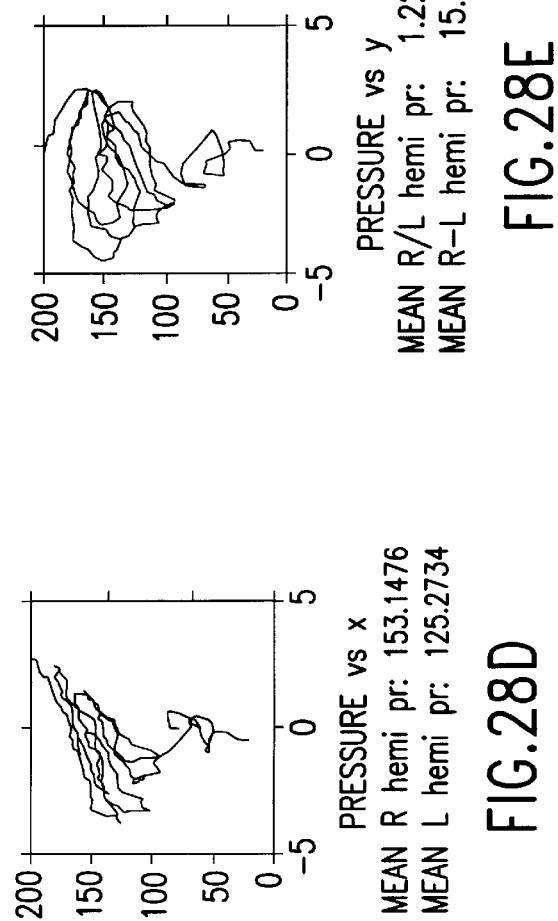
FIG.28E
PRESSURE vs y
MEAN R/L hemi pr: 1.2225
MEAN R-L hemi pr: 15.65697%
FIG.28D
PRESSURE vs x
MEAN R hemi pr: 153.1476
MEAN L hemi pr: 125.2734

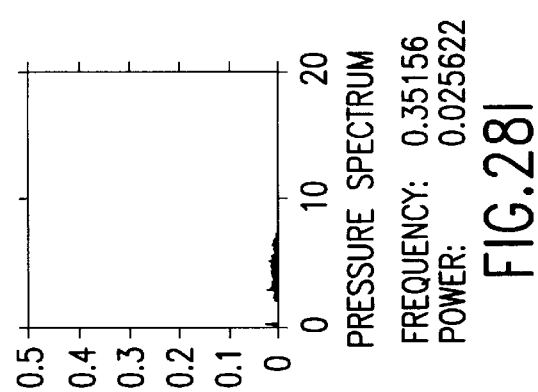
FIG.28G — X SPECTRUM
FREQUENCY: 1.1865
POWER: 0.00062246
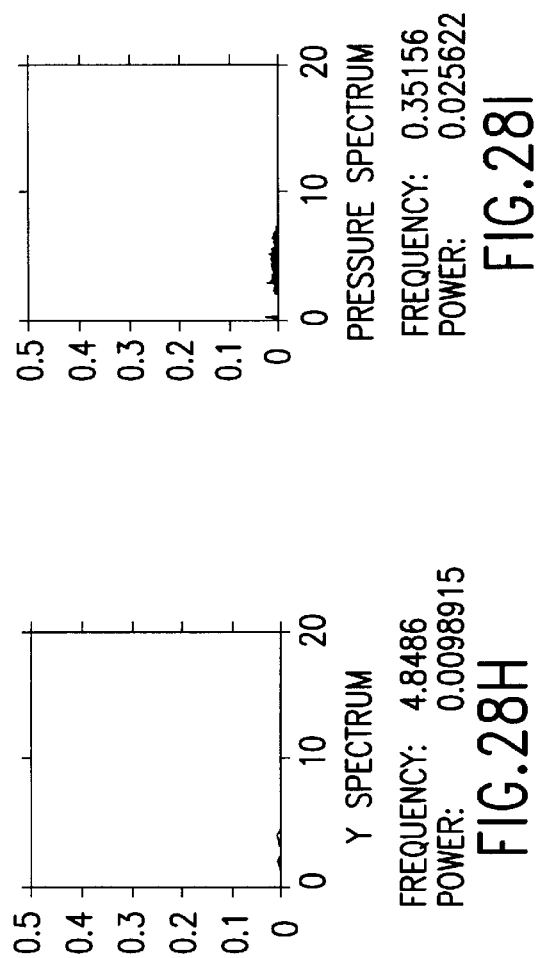
FIG.28H — Y SPECTRUM
FREQUENCY: 4.8486
POWER: 0.0098915
FIG.28I — PRESSURE SPECTRUM
FREQUENCY: 0.35156
POWER: 0.025622
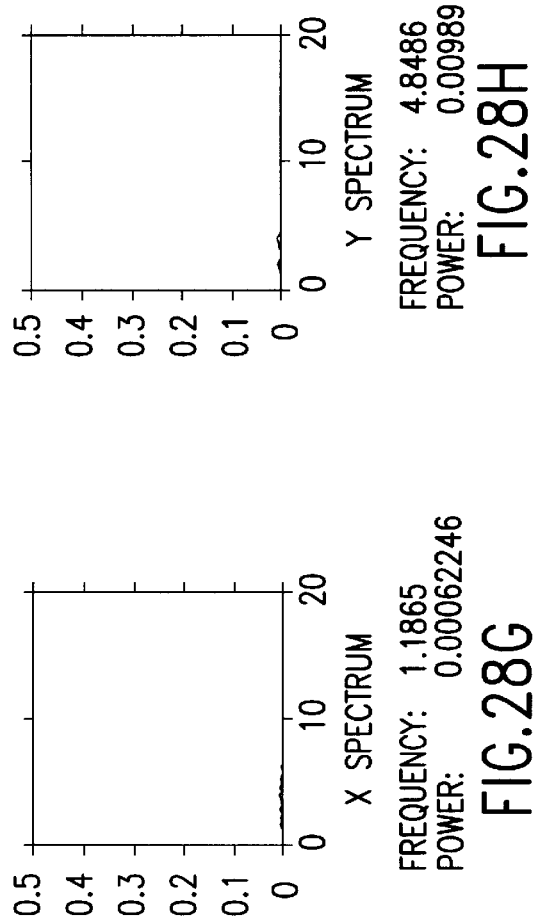
FIG.28J — SPEED
SPEED PEAK: 11.4363
SPEED MEAN: 4.903
SPEED MEAN SLOPE: 0.020919
FIG.28K — SPEED SPECTRUM
FREQUENCY: 0.32227
POWER: 0.081702
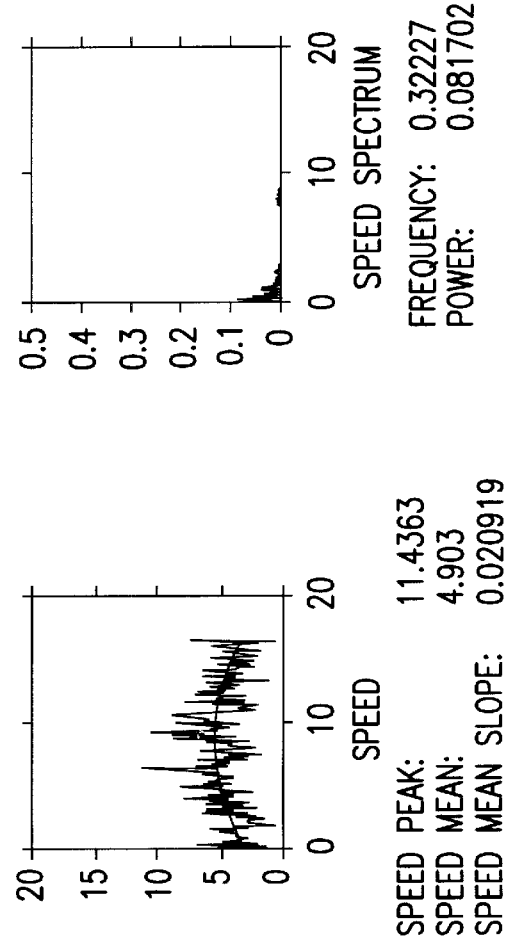
FIG.28L — ACCELERATION
ACCELERATION PEAK: 1.7086
ACCELERATION MEAN: 0.0051561
ACCELERATION MEAN SLOPE: −0.001945
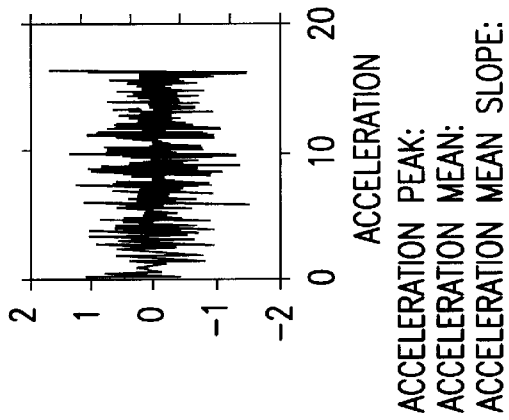

SYSTEM AND METHOD FOR CLINICALLY ASSESSING MOTOR FUNCTION

A portion of the disclosure of this patent document contains material which is subject to copyright protection. The copyright owner has no objection to the facsimile reproduction by anyone of any portion of the patent document, as it appears in any patent granted from the present application or in the Patent and Trademark Office file or records available to the public, but otherwise reserves all copyright rights whatsoever.

A microfiche appendix containing source code utilized in practicing an exemplary embodiment of the invention is included as part of the Specification and is hereinafter referred to as Appendix A. Appendix A includes a total of 2 microfiche and a total of 151 frames.

FIELD OF THE INVENTION

This invention relates in general to the field of neurology and neurological testing. More particularly, the present invention relates to the objective clinical assessment of motor function by computer analysis of a digitized writing sample, as may be used in the diagnosis and monitoring of motor disorders as well as the evaluation of motor development and handedness in children.

BACKGROUND OF THE INVENTION

A patient may seek medical treatment for a variety of complaints which suggest a disturbance of motor function, such as weakness, stiffness, tremor, clumsiness, or difficulty in executing movements. It then is the physician's responsibility to correctly diagnose the patient, and to implement the appropriate course of treatment. A number of syndromes which involve motor dysfunction exist, and are defined by their clinical manifestations.

For example, Parkinson's Disease, which results from a degeneration of cells in the basal ganglia of the brain, is associated with slowness of movement ("bradykinesia"), muscle rigidity, and a tremor often said to have a "pill rolling" quality which occurs at rest but tends to diminish with voluntary movements. In addition, patients suffering from Parkinson's Disease may exhibit a loss of facial expression, a difficulty in initiating movements, and a diminution of their handwriting ("micrographia").

Another fairly common motor disorder is essential tremor, an inherited condition which can present in childhood but more typically appears later in adult life. It usually involves the upper limbs, but may also affect the head, jaw, lips, tongue and pharynx. This tremor may abate upon ingestion of alcohol or beta-adrenergic antagonists. It may interfere with voluntary movements to the point where a sufferer is unable to drink from a glass or raise a spoon without spilling its contents.

There are numerous other motor disorders from hyperkinetic conditions such as essential tremor mentioned above to complex akinetic-rigid and other degenerative syndromes. Motor disorders may be considered primary when there are no known causes (other than genetics) and secondary, or symptomatic, when a known etiologic agent exists. Examples of primary motor disorders include Parkinson's disease, essential tremor and adult onset focal dystonia such as writer's cramp. Secondary motor disorders are more numerous and include Parkinsonian syndromes, side effects of medications such as tardive dyskinesia from neuroleptic use, immune, ischemic or even traumatic causes.

The multitude of motor disorders share many overlapping symptoms and signs. Even though sophisticated rating systems have been developed for some disorders (e.g., Parkinson's Disease) to aid in the accuracy of diagnosis, in the hands of inexperienced practitioners, or where the disease is in its early stages and clinical signs are subtle, the potential for an erroneous diagnosis is substantial. Diagnosis by a traditional neurologic exam may also be difficult where the patient is unable to comply with fairly detailed instructions for tests used to evaluate motor function. As an example, a young child or a demented adult suspected of having a defect in motor development may be difficult to evaluate.

If an error in diagnosis is made, there may be significant adverse consequences. For example, the appropriate therapies for Parkinson's Disease and essential tremor are very different, in that patients with Parkinson's Disease are treated with agents that increase or facilitate dopamine activity whereas patients with essential tremor are treated with agents that block beta-adrenergic neurotransmitters. Not only would misdiagnosis result in a lack of a clinical benefit, but administering the inappropriate drug could have undesirable or even toxic side effects.

For example, beta adrenergic blocking agents can adversely affect cardiac or pulmonary functions; unnecessary use in a Parkinson's Disease patient, particularly an older patient, could be dangerous. Similarly, use of agents that treat Parkinson's disease in a patient without that condition could have harmful consequences. Specific examples of Parkinson's Disease treating agents include artane, sinemet and baclofen. Artane, an anticholinergic agent used to treat Parkinsonian tremors and dystonia can severely affect cognition, cardiac, visual and urinary function. Sinemet, a mainstay drug for Parkinson's disease, causes nausea, vomiting, hallucinations and low blood pressure. Baclofen, an anti-spasmodic agent, and clonazepam, an anxiolytic and muscle relaxant, are used in many motor disorders but can alter mental status, blood pressure and can even be fatal when used inappropriately.

Further, even where the correct diagnosis has been made, it is important to be able to evaluate the clinical progress of a patient. Often the methods for measuring progress are extremely subjective.

One means by which clinicians have attempted to decrease subjectivity in diagnosis and monitoring motor function has been through the use of standardized clinical tests. Examples of such tests include asking the patient to touch his finger to, alternately, his nose and the outstretched finger of the examiner, or to run her heel up and down her shin, or to touch his or her thumb to, in succession, each of the other fingertips of the same hand.

Drawing has been used to evaluate motor function for many years. The famous neuropsychiatrist Kraepelin, at the beginning of this century, adapted an instrument to quantitatively analyze signatures for the evaluation of motor function in schizophrenic patients (Blyler et al., 1997, Schizophrenia Res. 26: 15–23, citing Hoch, 1904, Psychol. Bull. 1:241–257). One common test involves asking the patient to draw an Archimedes spiral. A thorough discussion of the spiral drawing test may be found in Bain & Findley, in "Standards in Neurology, Series A: Assessment, diagnosis and evaluation, Book I: Assessing Tremor Severity," published by Smith Gordon and Co., Ltd., London, England/Nishimura Co., Ltd., Niigata-Shi, Japan, copies of which can be obtained in the United States through Books International Inc., Herndon, Virginia. According to that reference, the severity of tremor apparent in the spiral is rated from 0–10, where critical factors in determining the grade of a particular spiral are the degree of perpendicular displacement of the track from the intended trajectory and the extent to which tremor persists during each turn (Bain & Findley, p.9). Tremor is said to become more apparent in the outward turns of the spiral. An example of a study which used spiral analysis to quantify the effects of the drug terguride in Parkinson's Disease patients is reported in Filipova et al., 1988, Eur. Arch. Psychiatr. Neurol. Sci.237:298–303. Another study which used spiral copying ability to evaluate the effect of the drug ondasetron on cerebellar tremor is described in Rice et al., 1997, J. Neurol. Neurosur. & Psychiat. 62:282–284.

A number of investigators have attempted to lessen the subjectivity of evaluation by using computer assistance. For example, Elble et al. (1996, Movement Disorders 11:70–78) asked patients with essential tremor to write a series of cursive e's and l's and, in some cases, to draw an Archimedes spiral on a digitizing tablet. They reported detecting changes in mean acceleration amplitude and tremor frequency with an accuracy which indicated that use of such a tablet was an accurate and less-costly alternative to accelerometry for tremor evaluation.

Wissel et al. (1996, J. Neurol. Neurosurg. & Psychiat. 61:172–175) used a digitizing tablet to measure writing speed in an evaluation of the effectiveness of botulinum toxin for treating writer's cramp.

Eichorn et al., 1996, (Movement Disorders 11:289–297) used a computational analysis of open loop handwriting movements, as captured by a digitizing tablet, to monitor the effect of apomorphine on patients with early untreated Parkinson's Disease. They reported that computer-assisted analysis of automated handwriting movements can be a quick method for quantifying dopamimetic effects on handwriting movements in parkinsonian patients. However, they also found that there was no statistically significant correlation when changes in the individual handwriting parameters were correlated with a subscore obtained using the Unified Parkinson's Disease Rating Scale ("UPDRS"; Lang and Fahn, 1989, in "Quantification of neurologic deficit," Munsat, ed., Butterworth-Heinemann, Storeham, Mass., pp. 285–309) for the writing hand, an observation which they indicated was expected, as the LPDRS assesses different kinds of parkinsonian symptoms, such as rigidity, akinesia, and tremor.

Blyler et al. (1997, Schizophrenia Res. 26: 15–23) used line drawing to measure lateralized motor performance in schizophrenic patients. The patients drew lines on a piece of paper, which were then scanned into a computer and a regression was run on the points of the line and used to calculate the deviation from straightness. The results were found to correlate with clinical rating scales of motor function, including the Simpson—Argus Rating Scale (Simpson and Argus, 1970, Acta Psychiatr. Scand. 212 (Suppl.), 9–11) for parkinsonian symptoms.

Slavin et al., 1999, J. Internatl. Neuropsychol. Soc. 5:20–25, used a digitizing tablet to analyze writing samples from patients with dementia of Alzheimer's type ("DAT"). Kinematic measures of stroke length, duration, and peak velocity were expressed in terms of consistency via a signal-to-noise ratio. Patterns typical of DAT but not Parkinson's disease were observed.

Lange-Küttner (1998, Perceptual and Motor Skills 86:1299–1310) report that speeded drawing of basic graphic patterns by young children, as captured on a digitizing tablet, could be used to identify psychophysical problems.

Computational analysis of handwriting, for identification or analytical purposes, is described in Singer and Tishby, 1994, Biol. Cybern. 71: 227–237; van den Heuvel et al., 1998, Acta Psychologica 100: 145–159; and Morasso and Sanguineti, 1993, Acta Psychologica 82: 213–235.

In recent years the inventor has reported the use of a digitizing tablet and computer analysis of written spirals to evaluate motor disorders such as Parkinson's Disease and essential tremor (Pullman et al., 1995, Neurology 45 (Suppl 4):A218 (abstract 208S); Yu et al., 1997, Society for Neuroscience Abstracts 23:abstract 737.8; Yu et al., 1998, Society for Neuroscience Abstracts 24:abstract 672.2). During this period of time, the inventor has been developing a method of producing a clinical rating which, unlike Eichorn's measurements, correlates with the UPDRS score based on the computer analysis of handwritten spirals. This method is not described in any of the foregoing disclosures, but is disclosed herein.

SUMMARY OF THE INVENTION

The aforedescribed limitations and inadequacies of conventional systems and methods for analyzing movement disorders are substantially overcome by the present invention, in which a primary object is to provide a relatively inexpensive and non-invasive computerized system and method for clinically assessing motor function. Such a system and method can be adapted for analyzing movement disorders such as Parkinson's disease, essential tremor and dystonia, and for characterizing neurological development and handedness in children.

In particular, the present invention relates to a computerized system and method for clinically assessing motor function comprising correlating geometric indices, computed from digital information obtained from a geometric shape drawn by a subject to be evaluated, with a clinical rating score derived using a "standard of reference" generated by one or more clinical expert. By analogy to a biochemical assay, which measures the amount of reactant by comparison to a standard curve, the present invention provides a method and system by which a medical practitioner can evaluate the motor function of a subject by generating a digitized writing sample and computationally comparing geometric indices obtained therefrom with values associated with clinical ratings assigned by skilled neurologists. Interpretation is thereby rendered more objective and consistent. Furthermore, the test may be administered and interpreted by physicians who are not skilled or experienced in evaluating motor disorders, for example general practitioners or pediatricians who are not specialized in the practice of neurology. The present invention therefore provides a means for evaluating persons early in the course of disease, and for screening patients for motor dysfunction or, in the case of children, disorders of motor development.

Hence, in accordance with a first aspect of the present invention, a system for clinically assessing motor function in a subject is provided that includes: an electronic digitizing tablet having a writing device for obtaining a geometric pattern handwritten by the subject and providing one or more digital signals representing the pattern; and a microprocessor for processing the signals to derive one or more geometric indices representative of motor function and for computing from the indices, using the aforementioned expert-generated "standard of reference", a clinical rating score indicative of motor function of the subject.

In another aspect of the present invention, a preferred method for analyzing movement disorders includes: a method for clinically assessing motor function in a subject comprising: obtaining a geometric pattern handwritten by the subject on a digitizing tablet; generating one or more digital signals representing the geometric pattern; processing the signals to derive one or more geometric indices representative of motor function; and computing from the geometric indices, using the aforementioned expert-generated "standard of reference", a clinical rating score indicative of motor function of the subject.

Further objects, features and advantages of the invention will become apparent from the following detailed description taken in conjunction with the accompanying figures showing illustrative embodiments of the invention.

BRIEF DESCRIPTION OF THE DRAWINGS

For a complete understanding of the present invention and the advantages thereof, reference is now made to the following description taken in conjunction with the accompanying drawings in which like reference numbers indicate like features and wherein:

FIG. 23A–L through 28A–L present clinical data and its analysis, using the method of the invention, of spiral analysis performed on a patient suffering from Parkinson's Disease.

Figure 2:
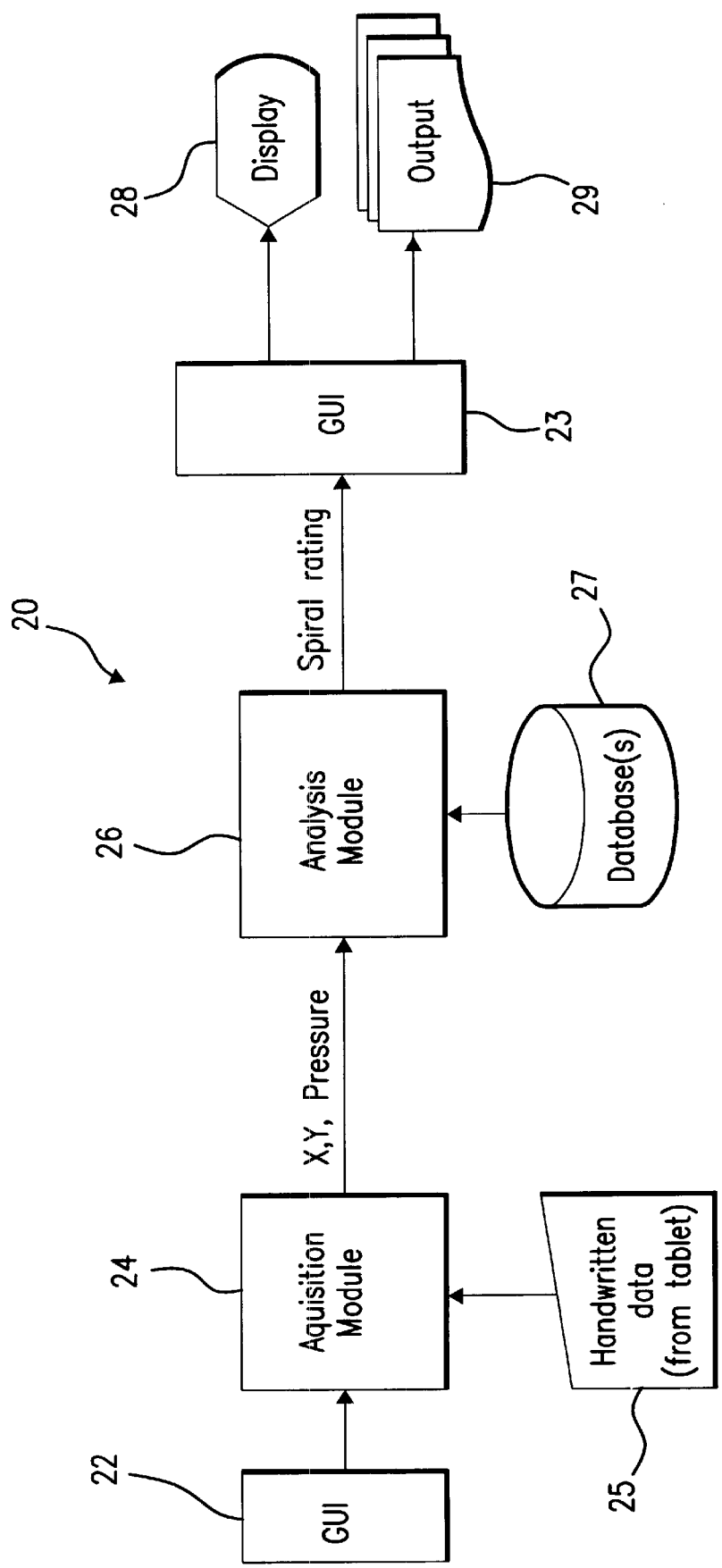
FIG. 2 is a software block diagram corresponding to the system of FIG. 1.

Appendix A hereto (in Microfiche form) includes a printout of computer source code corresponding to the software elements shown in FIG. 2.

While the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF THE PREFERRED EMBODIMENTS

Figure 1:
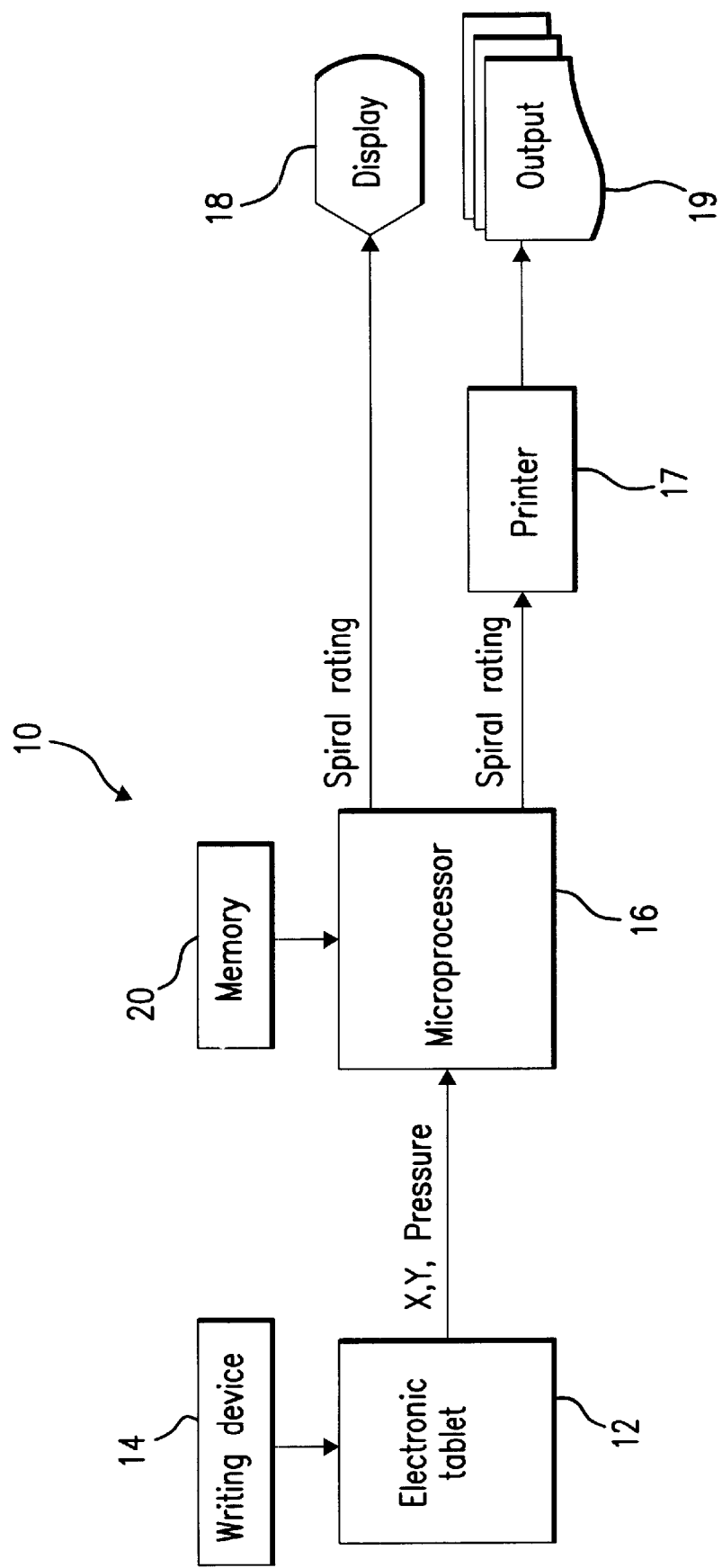
FIG. 1 is a hardware block diagram of a system for analyzing movement disorders in accordance with a preferred embodiment of the present invention.

FIG. 1 shows a hardware block diagram of a system 10 for clinically assessing motor function in accordance with a preferred embodiment of the present invention. The system 10 includes an electronic digitizing tablet 12 having a writing device 14 for obtaining a geometric pattern handwritten by the subject and providing one or more signals representing the pattern, and a microprocessor 16 for processing the signals to derive one or more geometric indices representative of motor function and for computing from the indices, using an expert-generated "standard of reference," a clinical rating score indicative of motor function.

The term "expert", as used herein, refers to a person skilled in the assessment of motor function and/or in the diagnosis and assessment of one or more motor disorder. Non-limiting specific examples of suitable experts include physicians, preferably neurologists, and more preferably neurologists specialized in the field of motor disorders.

In a preferred embodiment of the present invention, the handwritten samples are freehand Archimedes spiral patterns, drawn on an electronic tablet 12, that are digitized and analyzed by the microprocessor 16 in accordance with a set of spiral indices shown to be indicative of motor function. Further as shown in FIG. 1, a display device 18 and/or printer 17 are provided for displaying and/or printing an output 19 of the clinical rating, geometric indices and other relevant information.

The system of FIG. 1 can be adapted, for example, for diagnosing and/or monitoring movement disorders such as Parkinson's disease, essential tremor and dystonia, for evaluating neurological development and handedness in children, and for rehabilitative purposes. The spiral analysis program is also capable of analyzing any motor disorder involving the upper limbs, e.g., hand, forearm, arm, shoulder. The system can also be adapted for handwriting identification and psychiatric evaluation purposes. With proper use of controls and normative data, spiral analysis should be of use in any condition from tremors to developmental abnormalities.

FIG. 2 shows a software block diagram corresponding to the system of FIG. 1. In a preferred embodiment of the present invention, the software 20 includes: an input graphical user interface (GUI) 22, an acquisition module 24, an analysis module 26, an analysis database 27 and an output GUI 23 which can deliver the results of analysis via a display device 28 and/or printer output 29. The acquisition module 24, via the GUI 22, instructs the user to provide any user-related information including user-defined parameters for generating a digitized geometric pattern. Handwritten "manual" data 25 is provided by the patient as instructed by the acquisition module. The X-position, Y-position and pressure data is then forwarded to the analysis module 26 for the determination of disorder severity. Software code listings, which are non-limiting working examples for the acquisition and analysis modules of free-hand spirals 24 and 26, can be found in Appendix A (also referred to herein as "the Appendix"), and incorporate a correlation between the observed indices and a standard of reference established by an expert panel of neurologists, as set forth below. In the Appendix, the acquisition module 24 is embodied in C-language routines, whereas the analysis module is embodied in MatLab routines.

Referring again to FIG. 1, the data output from the electronic tablet is provided to the microprocessor 16, which is preferably an Apple MacIntosh or IBM-compatible personal computer. The microprocessor 16 is coupled to computer memory 20, which contains the analysis software module 26 shown in FIG. 2. The microprocessor 16 thus runs the analysis module 26, which in turn accesses an analysis database 27 (FIG. 2). The database 27 is used for storing and retrieving, for example, patient demographics and indices output. The analysis module 26 receives the X-position, Y-position and pressure data from the acquisition module 24 and computes a plurality of geometric indices used to assess the upper limb motor abilities of the patient. Although the analysis module 26 can be applied to analyze a variety of geometric patterns, the analysis module 26 of a preferred specific embodiment of the invention includes an algorithm that analyzes hand-drawn (Archimedean) spirals.

Figure 3:
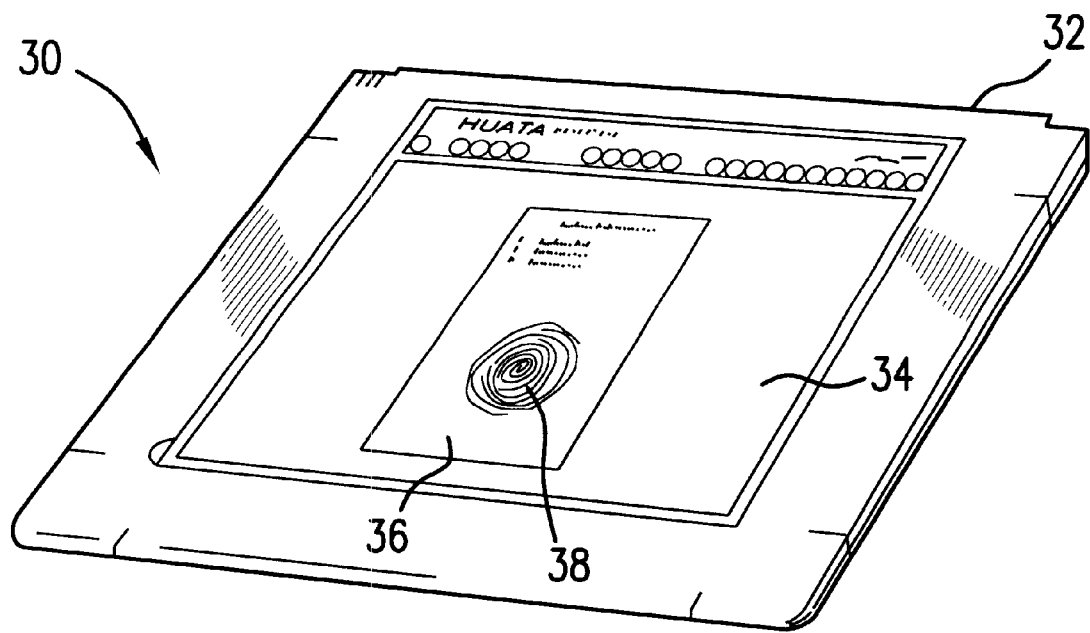
FIG. 3 is an illustration of an electronic tablet in accordance with a preferred embodiment of the present invention.
Figure 4A:
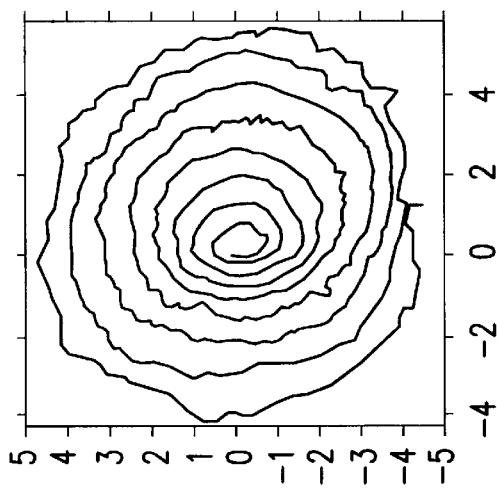
FIGS. 4(a) through 4(f) are examples of spirals and corresponding r versus θ plots.
Figure 4B:
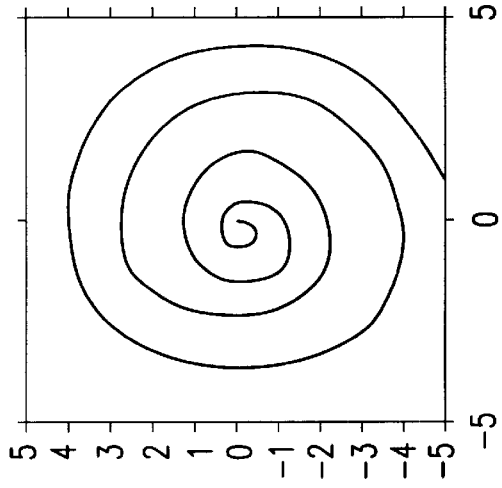
Figure 4C:
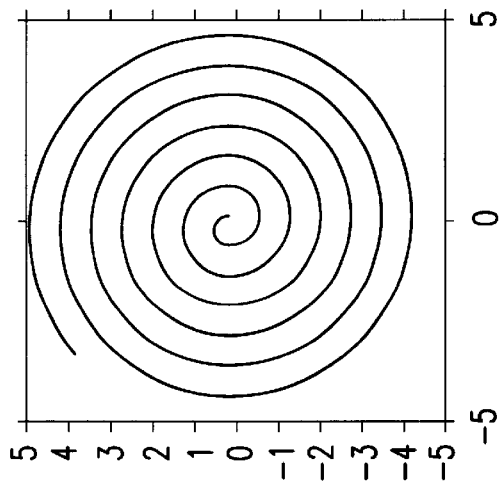
Figure 4D:
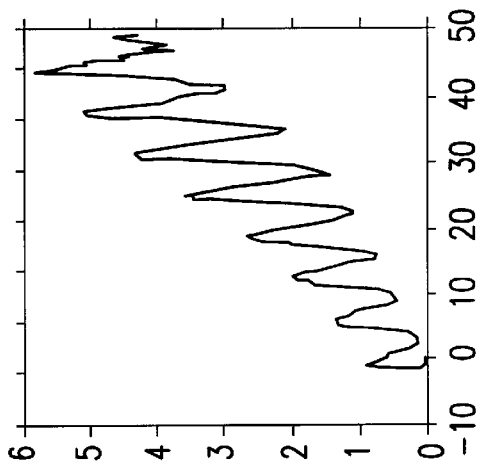
Figure 4E:
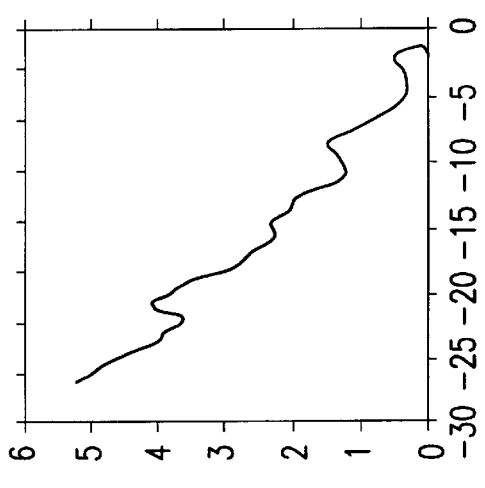
Figure 4F:
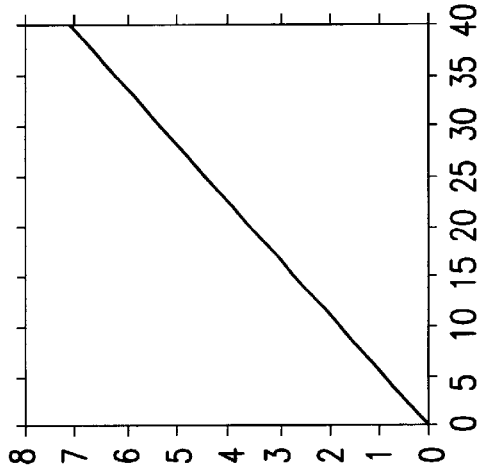

FIG. 3 shows an illustration of an electronic tablet 30 for use with the system of FIG. 1. The electronic tablet 30 is a portable digitizing tablet such as the tablet produced by Kurta. Inc. as the Kurta XGT™ 6"×8", which is sold together with a pressure pen, and is shown by way of example and not limitation. Other suitable "tablet" devices may include, for example, any stationary or portable digitizing device having a stylus, pen or other active writing device. The electronic tablet 30 of FIG. 3, however, is preferred because it is designed for use with a cordless writing pen (not shown) that writes (i.e., creates a written image) on a sheet of paper placed on top the tablet. As such, the electronic tablet 30 provides a "pen-on-paper" feel that is much like drawing on an ordinary sheet of paper. In addition, a hardcopy original of the patient's drawing is made available for future reference. Non-limiting examples of other digitizing tablets which may be used according to the invention are the Wacom Digitizer Graphic Tablet No. UD-1212II and the Calcomp 9000 digitizing tablet. In order for the subject to visually monitor his or her drawing, a lightweight paper which shows pen tracings, such as thin thermal fax paper, or a connection to a computer having a screen which displays the image being drawn, may be used, as described, respectively, in Lange-Küttner (1998, Perceptual and Motor Skills 86: 1299–1310) and Van Den Heuvel et al. (1998, Acta Psychologica 100:145–159).

The electronic tablet 30 includes a back panel 32 and a digitizing screen 34. The electronic tablet 30 also includes a microprocessor (not shown), computer memory (not shown) and a computer program for controlling the operation of the electronic tablet. In a preferred embodiment of the present invention, the computer program is the acquisition module 24 described above with respect to FIG. 2. The digitizing screen 34, which supports a sheet of paper 36 on which a patient draws a pattern 38, is a pressure sensitive X-Y plane recording device that generates "tri-axial" signals indicative of the drawing position and the force exerted by the patient. The device normally provides a resolution of 2,540 points/inch (100 points/mm), with an accuracy of ±0.005 inch (0.127 mm) in the X-Y directions. Pressure readings are output using 256 distinct levels, nominally 2.5 gms/level, and optionally can be to assess motor function.

Preferably, the electronic tablet outputs an X-position, Y-position, pressure reading and a corresponding time stamp at each sample interval. Preferably, the sample rate is normally 220 samples per second, but must be at least 73 samples per second.

In further embodiments of the electronic tablet, a clip, fastener or other equivalent device (not shown) is provided for holding the sheet of paper 36 in a fixed position on top of the digitizing screen 34. Also, an ergonomically adaptable workstation (not shown) is provided along with the electronic tablet for optimal positioning and comfort.

A sample data output from an electronic tablet is provided in FIG. 4, where spiral (a) corresponds to r versus (also indicated herein by a tilda, "~") θ plot (d), spiral (b) corresponds to r versus θ plot (e), and spiral (c) corresponds to r versus θ plot (f). FIG. 4(a) shows an ideal, computer generated spiral, as compared to one drawn by a normal subject shown in FIG. 4(b). FIG. 4(c) further shows a spiral drawn by a patient suffering from a movement disorder.

Where the analysis module 26 is applied to the analysis of Archimedean spirals, it uses "spiral" indices to objectively characterize a hand-drawn spiral. The spiral is "unraveled" from a two-dimensional graphic representation into indices that capture clinical information, e.g., shape, speed. tremors. pressure applied, etc., related to a patient's motor function. A list of such indices is provided in the Table 1 below:

TABLE 1

List of Geometric Indices

| Index No. | Description |
|---|---|
| $I_1$ | First order smoothness. |
| $I_2$ | Second order smoothness. |
| $I_3$ | Tightness of Loops. |
| $I_4$ | First order "zero" crossing rate. |
| $I_5$ | Second order "zero" crossing rate. |
| $I_6$ | Residue of radius-angle regression (second order polynomial, least square) |
| $I_7$ | Residue of pressure-time regression (second order polynomial, least square) |
| $I_8$ | Residue of speed-time regression (second order polynomial, least square) |
| $I_9$ | X-axis frequency (dominant). |
| $I_{10}$ | Dominant X-axis frequency power. |
| $I_{11}$ | Y-axis frequency (dominant). |
| $I_{12}$ | Dominant Y-axis frequency power. |
| $I_{13}$ | Angular velocity frequency (dominant). |
| $I_{14}$ | Dominant angular speed frequency power. |

TABLE 1-continued

List of Geometric Indices

| Index No. | Description |
|---|---|
| $I_{15}$ | X-Y combined speed frequency (dominant). |
| $I_{16}$ | Dominant X-Y combined speed frequency power. |
| $I_{17}$ | Residue of angular velocity-time regression. |

As described below, some or all of the above-identified indices are used to clinically rate the motor function of the patient. However, in a preferred embodiment of the present invention, the clinical rating score is expressed as a function of $I_1$, $I_2$ and $I_5$, as shown below by Equation (1), where an asterisk (*) indicates the operation of multiplication and a tilda (~) means "versus":

$$\text{Clinical Rating Score} = 0.4615 * I_1 + 0.0544 * I_5 - 0.2331 * I_1^2 - 0.0726 * I_2^2 - 0.001 * I_5^2 + 0.2539 * I_1 * I_2 + 1.3668 \quad \text{Equation (1)}.$$

The rating score according to Equation (1) is clinically equivalent to those of the United Parkinson's Disease Rating Scale (UPDRS) established to rate the degree of severity of Parkinson's disease and related disorders. The rating score is based on UPDRS scale for upper limb motion with regard to several factors, including tremor, hand movements, handwriting and rigidity, and incorporates a "standard of reference" established by a plurality of expert neurologists.

The Clinical Rating Score calculated by Equation (1) may be used to determine whether a subject has normal or abnormal motor function. The abnormal motor function may correlate with a diagnosis of a motor disorder such as, but not limited to, Parkinson's disease, essential tremor, or dystonia (see infra). Accordingly, if analysis of a spiral drawn by a subject, according to the invention, comprising obtaining spiral indices $I_1$, $I_2$ and $I_5$ and utilizing these indices in Equation (1), yields a value of between 0 and 1, this indicates that the subject is exhibiting essentially normal motor function as measured by indices $I_1$, $I_2$ and $I_5$. If Equation (1) yields a value of between 1 and 2, this would indicate that the subject is exhibiting mildly abnormal motor function. If Equation (1) yields a value of between 2 and 3, this would indicate that the subject is exhibiting moderately abnormal motor function. If Equation (1) yields a value of between 3 and 4 or higher, this would indicate that the subject is exhibiting severely abnormal motor function. If Equation (1) yields a value between these ranges, such as a value of 1, 2, or 3, this would indicate that the subject is exhibiting motor function that is characterized either as borderline normal (value=1), mildly to moderately impaired (value=2), or moderately to severely impaired (value=3). Further, as the value of the Clinical Rating Score increases, the likelihood that the patient is suffering from a motor disorder increases as well.

Equation (1) was derived, at least in part, as follows.

Spirals and their corresponding indices were obtained from 25 normal control subjects and three groups of 15 patients suffering from Parkinson's Disease ("PD"), essential tremor ("ET") and dystonia ("DY"), respectively. Each of the spirals were independently rated by 22 movement disorder specialist neurologists based on a modified UPDRS scale: a 0–1 corresponding to a "normal" spiral; 1–2 corresponding to a "mildly abnormal" spiral; 2–3 corresponding to a "moderately abnormal" spiral; and 3–4 corresponding to a "severely abnormal" spiral. The criteria set forth in Table 2 were provided to aid the neurologists in rating patient spirals.

Grade 0: The spiral approaches an ideal spiral with a regular shape, evenly spaced loops, well centered, with a smooth fluid line and 3 to 10 loops.

Grade 1: The spiral is well executed but has one or two of the following:
 mild irregularity of spacing, shape, smoothness of the line, or wandering from the center.

Grade 2: The spiral is relatively well executed but has two or three of the following:
 mild to moderate irregularity of spacing, shape, smoothness of the line, or wandering from the center.

Grade 3: The spiral is relatively well executed but has two or three of the following:
 moderate to severe irregularity of spacing, shape, smoothness of the line, or wandering from the center.

Grade 4: The spiral is poorly executed or unrecognizable as a spiral and has more than three of the following:
 severe irregularity of spacing, shape, smoothness of the line, wandering from the center, many areas of in continuity, or there are more than 10 or less than 3 loops to the spiral.

Table 2: Spiral Analysis Rating System

To determine the top ten so-called "expert" physicians, a regression was performed between each physician's clinical ratings and the average clinical rating for each clinical rating (excluding that physician's own rating). The physicians with the top ten regression coefficients where chosen as the "expert" physicians, and as such the indices computed from the spirals rated by the ten experts were averaged.

Figure 5:
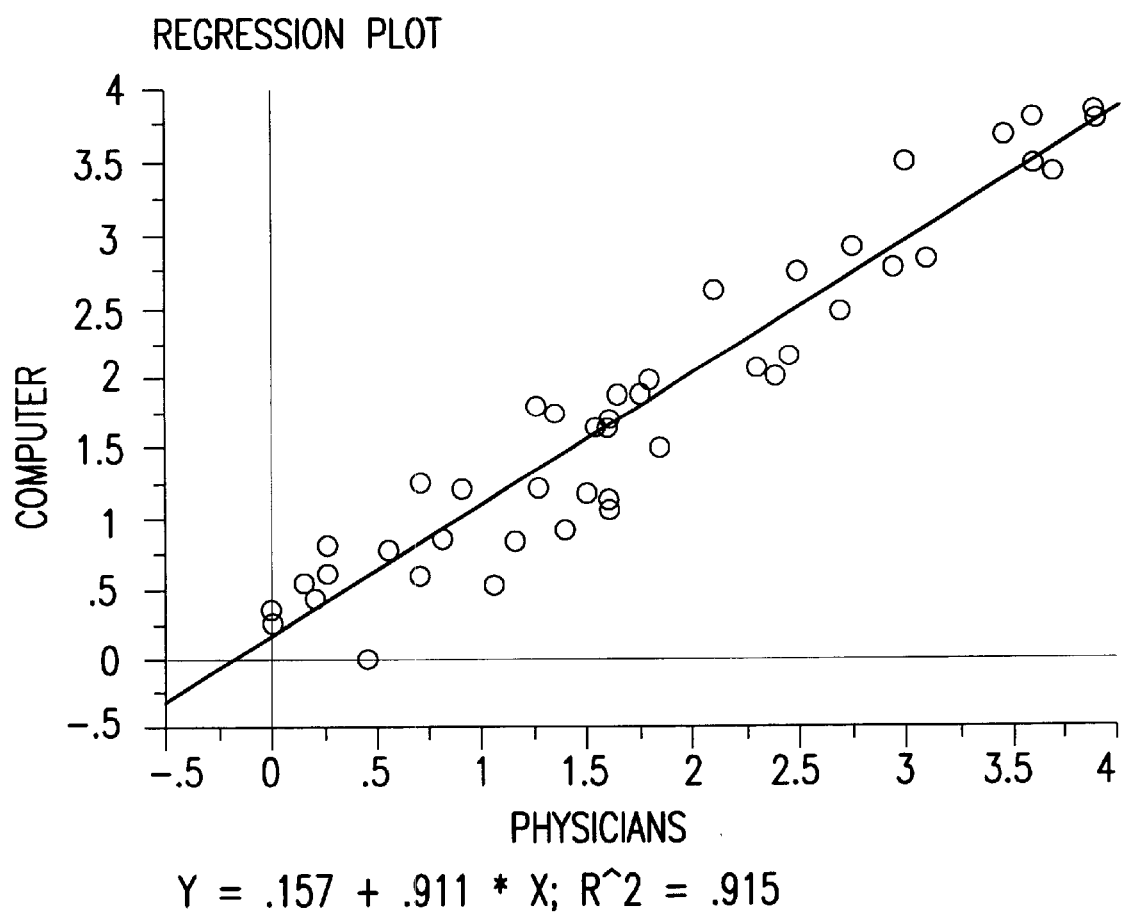
FIG. 5 is a regression plot comparing computer generated clinical ratings (degree of severity computations) and expert physician clinical ratings.

In order to characterize interdependencies between indices, linear and second order polynomial regressions were then performed for each index against the expert physician averages. Those indices with the most statistical significance and highest regression coefficients (r2), as shown in Table 3, were selected to define the clinical rating expression shown above in Equation (1). The clinical rating equation, which is a function of $I_1$, $I_2$ and $I_5$ has been shown to provide critical information on motor function and has been useful in quantifying spiral severity that directly correlates with normal subjects (as opposed to an ideal spiral) and clinical status as reflected by the UPDRS. Thus, beyond merely providing a quantitative measurement of motor function, Equation (1) provides a score which, because it correlates with the UPDRS, has a clinical significance readily appreciated by practitioners. Also, as shown in FIG. 5, regression of the original ten physician spiral DOS scores, as well as the new DOS scores, has consistently yielded significant correlations, i.e., $r^2$ from approximately 0.085 to 0.915 and a statistical significance less than 0.001.

TABLE 3

Simple Regression and Significance for Each Index (versus Expert Physician Average)

| Index No. | Description | Regression Coefficient | Significance |
|---|---|---|---|
| $I_1$ | First order smoothness. | 0.871 | <0.001 |
| $I_2$ | Second order smoothness. | 0.740 | <0.001 |
| $I_3$ | Tightness of Loops. | 0.010 | 0.530 |
| $I_4$ | First order "zero" crossing rate. | 0.000 | 0.980 |
| $I_5$ | Second order "zero" crossing rate. | 0.540 | <0.100 |
| $I_6$ | Residue of radius-angle regression (second order polynomial, least square) | 0.010 | 0.040 |
| $I_7$ | Residue of pressure-time regression | 0.140 | 0.010 |

TABLE 3-continued

Simple Regression and Significance for Each Index
(versus Expert Physician Average)

| Index No. | Description | Regression Coefficient | Significance |
|---|---|---|---|
| | (second order polynomial, least square) | | |
| $I_8$ | Residue of speed-time regression (second order polynomial, least square) | 0.080 | 0.060 |
| $I_9$ | X-axis frequency (dominant). | 0.190 | <0.001 |
| $I_{10}$ | Dominant X-axis frequency power. | 0.120 | 0.020 |
| $I_{11}$ | Y-axis frequency (dominant). | 0.160 | 0.010 |
| $I_{12}$ | Dominant Y-axis frequency power. | 0.030 | 0.300 |
| $I_{13}$ | Angular velocity frequency (dominant). | 0.290 | <0.001 |
| $I_{14}$ | Dominant angular speed frequency power. | 0.060 | 0.120 |
| $I_{15}$ | X-Y combined speed frequency (dominant). | 0.300 | <0.001 |
| $I_{16}$ | Dominant X-Y combined speed frequency power. | 0.420 | <0.001 |
| $I_{17}$ | Residue of angular velocity-time regression. | 0.230 | 0.030 |

In deriving the indices $I_1$, $I_2$ and $I_5$ of Equation (1), reference is first made to Equation (2) and (3) below which are well known mathematical equations describing the Cartesian coordinates of an ideal spiral:

$$x = \alpha\theta \sin(\theta + c) \quad \text{Equation (2);}$$

$$y = \alpha\theta \cos(\theta + c) \quad \text{Equation (3);}$$

where x and y are the Cartesian coordinates, $\alpha$ is a constant parameter, $\theta$ is an angle parameter, and c is a constant representing an initial angle. The polar equivalent, as shown by Equation (4) translates the spiral into a linear relation between r and $\theta$ while maintaining all clinical information with total fidelity as it is a point-to-point transformation of the original spiral:

$$r = \alpha\theta \quad \text{Equation (4);}$$

where $r = \sqrt{(x^2 + y^2)}$.

Referring again to Equation (1), first and second order smoothness, indices $I_1$ and $I_2$, are mathematical expressions of spiral "waviness." These indices do not indicate spiral irregularities and are not direct measures of tremor, i.e., tremor measurement is performed via spectral analysis using Fast Fourier transforms. Rather, smoothness indices $I_1$ and $I_2$ are designed to detect variations from a normal spiral shape. The mathematical relations for first and second order smoothness are shown below by Equations (5) and (6):

$$I_1 = \ln\left(\frac{1}{\Theta} \sum \left(\frac{\Delta r}{\Delta \theta} - \bar{r}_\theta\right)^2 |\Delta\theta|\right); \quad \text{Equation (5)}$$

$$I_2 = \ln\left(\frac{1}{\Theta} \sum \left(\frac{\Delta \frac{\Delta r}{\Delta \theta}}{\Delta \theta} - d\bar{r}_\theta\right)^2 |\Delta\theta|\right); \quad \text{Equation (6)}$$

wherein: $\Theta$ is the total angular change, $\bar{r}_\theta$ is the average slope of r–$\theta$, $\Delta$ is a difference operator reflecting discrete changes due to sampling by the digitizing tablet, and $d\bar{r}_\theta$ is the average slope of $\Delta r/\Delta \theta$ ~$\theta$.

The zero-crossing rate indices, $I_4$ and $I_5$, are used to characterize the graphic irregularity, i.e., the "lopsidedness" and "unsmoothness," of the handwritten spiral. The zero-crossing rate indices are both expressed in percentage terms, i.e., the higher the percentage, the more irregular the spiral. The first order zero crossing index Irregular movements such as dystonic tremors reveal the highest second order zero crossing rates because they are "irregularly" irregular, i.e., the change in the irregularity of the spiral with respect to the change in angle $\theta$. The zero order crossing rate index $I_4$ is defined below by Equation (7):

$$I_4 = \frac{1}{2(J-1)} \sum_{j=1}^{J-1} \left| \text{sign}\left(\frac{\Delta r}{\Delta \theta}\bigg|_{j+1} - \bar{r}_\theta\right) - \text{sign}\left(\frac{\Delta r}{\Delta \theta}\bigg|_{j} - \bar{r}_\theta\right) \right| * 100\%; \quad \text{Equation (7)}$$

wherein J is the total number of points collected and sign is a sign function where y=sign (x) and sign(x)=1 for x>0, sign(x)=0 for x=0 and sign(x)=–1 for x<0.

The second order zero crossing rate index $I_5$ is defined below by Equation (8):

$$I_5 = \frac{1}{2(J-1)} \sum_{j=1}^{J-1} \left| \text{sign}\left(\frac{\Delta \frac{\Delta r}{\Delta \theta}}{\Delta \theta}\bigg|_{j+1} - d\bar{r}_\theta\right) - \text{sign}\left(\frac{\Delta \frac{\Delta r}{\Delta \theta}}{\Delta \theta}\bigg|_{j} - \bar{r}_\theta\right) \right| * 100\%; \quad \text{Equation (8)}$$

Index $I_3$, reflecting spiral tightness, is defined below by Equation (9):

$$I_3 = (\Theta/R - 14\pi)/2\pi \quad \text{Equation (9)}$$

Tightness is the mathematical correlate of micrographia and is defined by how many turns of the spirals are drawn over its total angular change within the total radius R, normalized to 7 (or $14\pi$ because each full loop equals $2\pi$). Tightness is positive when a spiral is drawn with more that 0.7 "loops" per centimeter of radius and negative when the "loops" are fewer in number or more spread out.

The remaining indices listed in Table 1 can be obtained using standard calculations.

Thus, the present invention provides for a method for diagnosing, monitoring, and/or assessing Parkinson's Disease in a subject comprising: obtaining a spiral drawn by the subject on a digitizing tablet; generating one or more digital signals representing the spiral; processing the signals to derive one or more geometric indices representative of motor function, where the indices are preferably one or more of indices $I_1$–$I_{17}$ as set forth in Table 1 and are more preferably indices $I_1$, $I_5$, and $_2$ as set forth in Table 1; and computing from the geometric indices, using an expert-generated "standard of reference", a clinical rating score indicative of the diagnosis and/or severity of Parkinson's Disease. Preferably, the clinical rating score (also referred to herein as the "degree of severity") is calculated using Equation (1):

Clinical Rating Score=0.4615*$I_1$+0.0544* $I_5$–0.2331*$I_1^2$– 0.0726*$I_2^2$–0.001*$I_5^2$+0.2539*$I_1$*$I_2$+1.3668

The clinical rating score obtained for the subject may then be used, in conjunction with other clinical tests or physical examination, to diagnose Parkinson's Disease in a subject. In a non-limiting, example, if Equation (1) is used to establish the clinical rating, a score of at least 1, and preferably of at least 2, bears a positive correlation with the diagnosis of Parkison's Disceasse in the subject.

The clinical rating score may also be used to monitor the progress and/or response to treatment of a subject previously diagnosed as suffering from Parkinson's Disease. In a particular, nonlimiting embodiment, the present invention provides for a method for monitoring Parkinson's Disease in a subject comprising, on a first occasion,(a) obtaining a spiral drawn by the subject on a digitizing tablet; (b) generating one or more digital signals representing the spiral;(c) processing the signals to derive one or more geometric indices representative of motor function; and(d) computing from the geometric indices, using an expert-generated standard of reference, a clinical rating score indicative of the diagnosis of Parkinson's Disease; on a second occasion, separated from the first occasion by an interval of time, repeating steps (a)–(d); and comparing the clinical rating scores obtained at the first occasion and the second occasion, where an increase in the score has a positive correlation with a worsening of motor function and a decrease in the score has a positive correlation with an improvement in motor function.

The foregoing embodiments may be varied, for example by asking the subject to draw a geometric pattern other than a spiral, for example, a figure eight, a series of loops, concentric rectangles, etc. In these variations, the equations used to produce the indices would need to be altered so as to be representative of the new pattern, and the correlation with a clinical rating score would need to be calculated with respect to a standard of reference established by ratings, by one or more expert, of a plurality of drawings of the new pattern, as drawn by parkinsonian patients of varying severity and healthy subjects.

In other related embodiments, the method of the invention may be used to diagnose, monitor, and/or assess motor disorders other than Parkinson's disease, including, but not limited to, essential tremor, cerebellar tremor, dystonia, cerebral palsy, tardive dyskinesia, and the motor symptoms of multiple sclerosis and schizophrenia, and any movement abnormality of the upper limb. According to such embodiments, the present invention provides for a method for diagnosing, monitoring, and/or assessing the motor disorder in a subject comprising: obtaining a handwritten spiral (or other geometric pattern) drawn by the subject on a digitizing tablet; generating one or more digital signals representing the spiral (or other geometric pattern); processing the signals to derive one or more geometric indices representative of motor function; and computing a clinical rating from the geometric indices, using an expert—generated "standard of reference" established by one or more expert, preferably by a plurality of neurologists, who assigned scores commensurate with disease severity, using a fixed scale to drawings of a spiral (or other geometric pattern) by patients suffering from varying degrees of severity of the motor disorder as well as normal healthy subjects, where the clinical rating score derived by the method is indicative of the diagnosis and severity of the motor disorder. Using methods analogous to those set forth above with relation to Parkinson's Disease, the methods of the invention may be used to monitor the progress and/or response to treatment of a subject previously diagnosed as suffering from other motor disorders.

Figure 6:
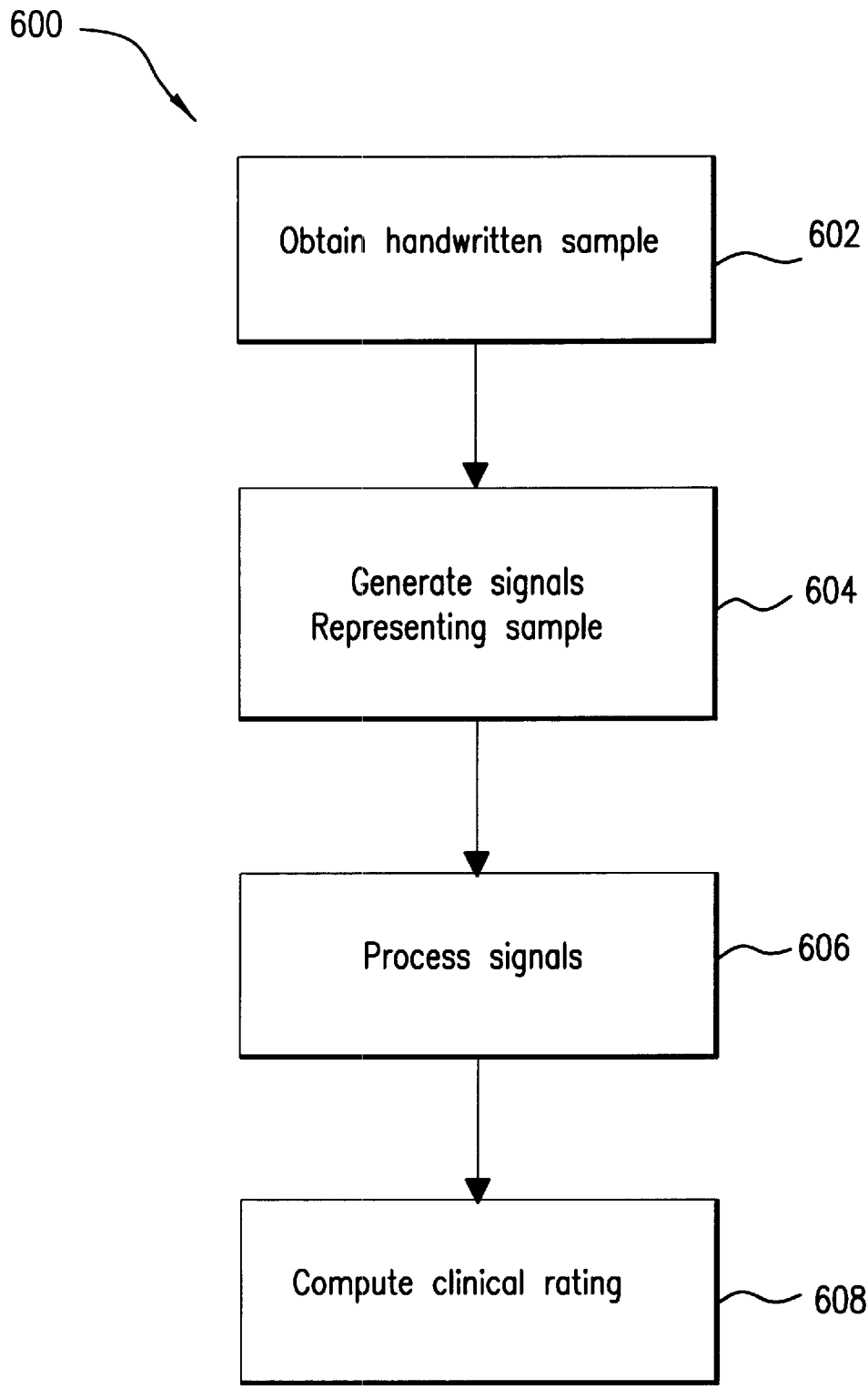
FIG. 6 is a flow chart showing a preferred method for analyzing movement disorders.

FIG. 6 shows a preferred method for clinically assessing motor function according to the present invention. The method 600 includes the steps of: obtaining a geometric pattern handwritten by a subject on a digitizing tablet, step 602; generating one or more signals representing the geo-metric pattern, step 604; processing the signals to derive one or more geometric indices representative of motor function, step 606; and computing from the geometric indices a clinical rating score indicative of motor function, step 608. The method of FIG. 6 can be implemented as a computer program in accordance with the system of FIG. 2. A detailed description of such an exemplar program now follows with reference to FIGS. 7 through 22.

Figure 7:
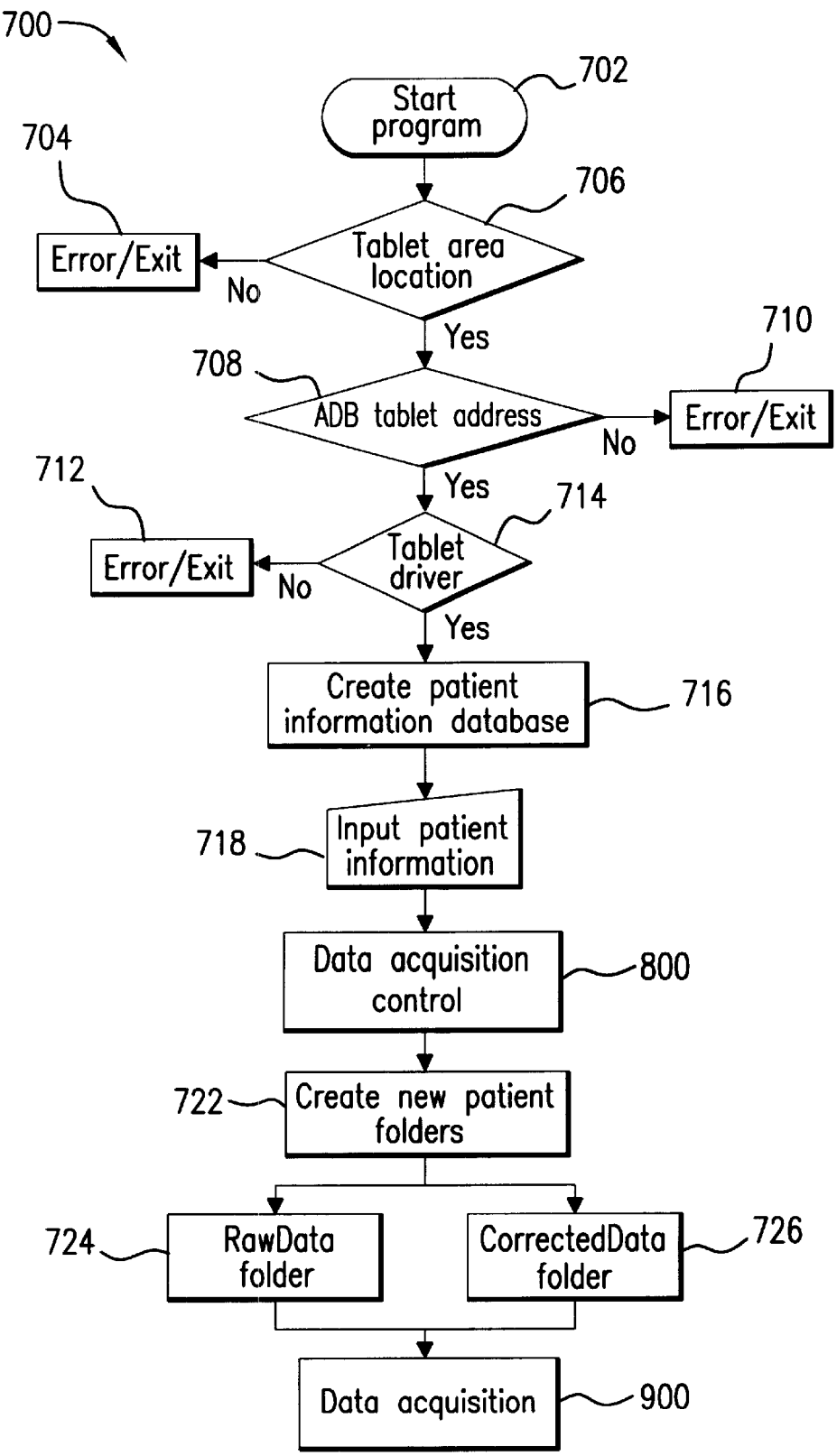
FIG. 7 is a flow chart showing a preferred method performed by the acquisition module of FIG. 2.

FIG. 7 shows a flow diagram 700 for the acquisition module 24 of FIG. 2. An exemplary computer program, trace.c, for performing spiral acquisition tasks is provided in Appendix A.

As shown in FIG. 7, after an operator starts the program, step 702, initial checks are performed to ensure that the electronic tablet is properly configured for data acquisition, steps 706, 708 and 714. These initial checks include checking the area location of the tablet, step 706, checking the tablet data address, step 708, and checking for an appropriate tablet driver, step 714. If any of these initial steps are unsuccessful, a corresponding error condition is generated and program execution is terminated, steps 704, 710 and 712. If the initial tablet checks are successful, the acquisition module continues by initializing a patient information database, step 716, and prompting the operator for patient information, step 718. Patient information may include, for example, the patient's name, age, sex and clinical condition. The program then performs data acquisition control functions, step 800, which are described below with respect to FIG. 8. After completion of step 800, new patient data files or "folders" are created, step 722, each including raw data and corrected data, steps 724 and 726, and data acquisition begins, step 900 (see FIG. 9).

Figure 8:
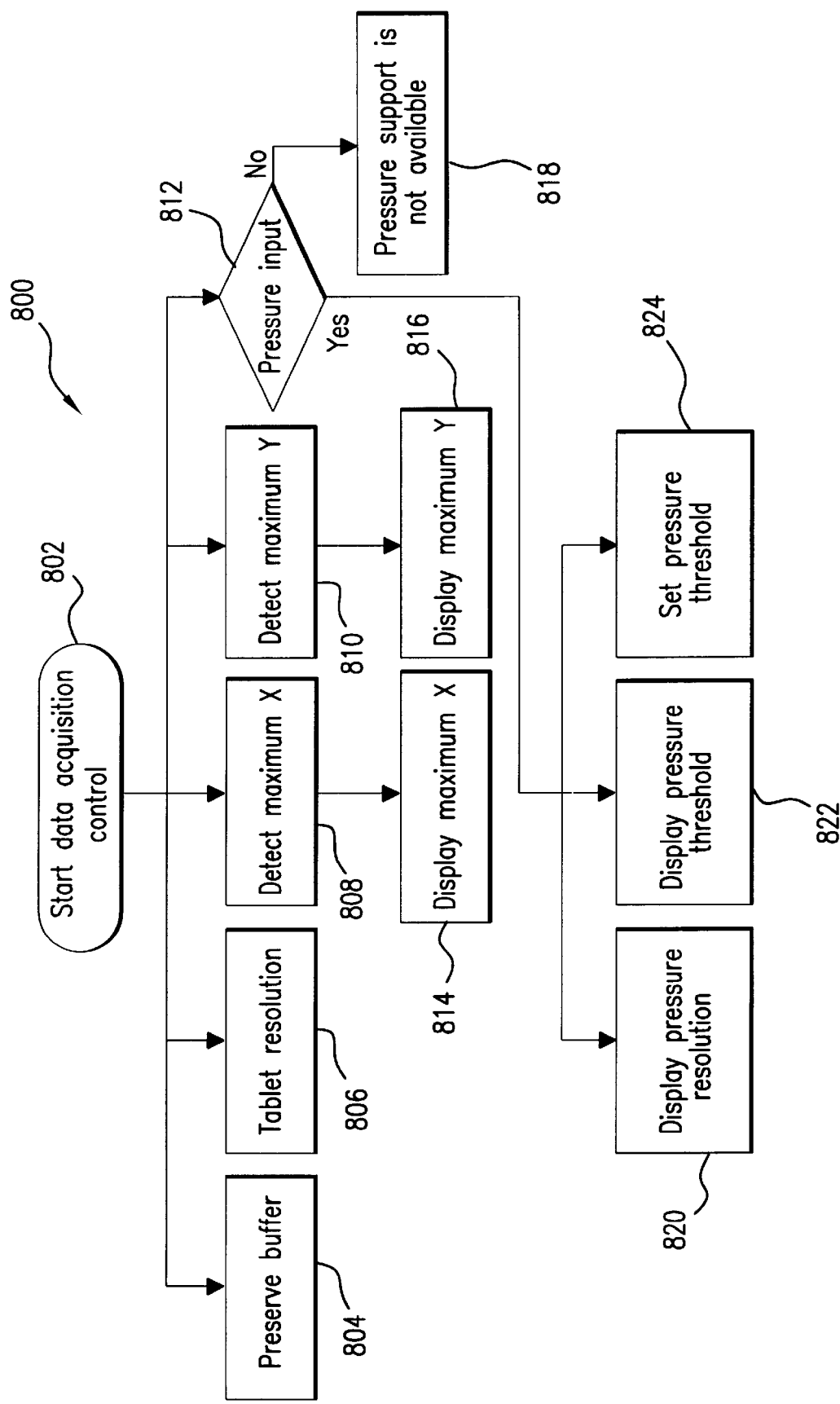
FIG. 8 is a flow chart showing a preferred method for controlling data acquisition in accordance with the method of FIG. 7.

Prior to the start of data acquisition, several additional control steps are executed, step 802, as shown in FIG. 8 to properly configure the system for data acquisition. These steps include preserving the tablet's data buffer, step 804, displaying the tablet resolution, step 806, detecting and displaying the maximum X-axis and Y-axis position values of the tablet, steps 808, 810, 814 and 816, and determining whether the tablet supports pressure data input, step 812. If the tablet does not support pressure data input, a flag is set indicating that pressure measurement is unavailable, step 818. If however the tablet supports pressure data input, then the pressure resolution (maximum pressure value) is displayed, step 820, and the pressure threshold (minimum pressure value) is displayed, step 822 and set, step 824.

Figure 9:
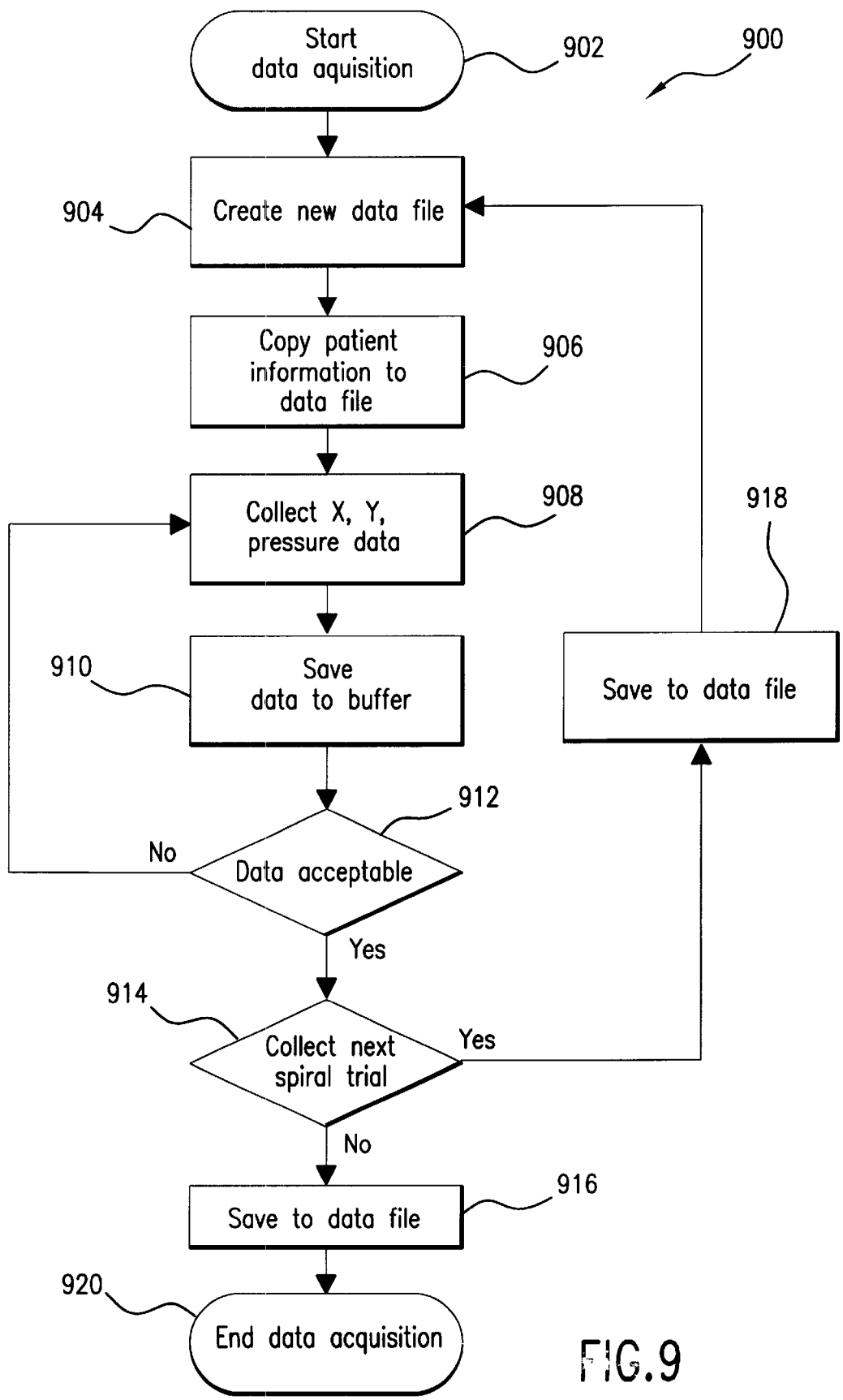
FIG. 9 is a flow chart showing a preferred method for acquiring data in accordance with the method of FIG. 7.

FIG. 9 shows a flow diagram of a preferred method 900 for acquiring data in accordance with the method of FIG. 7. After completion of steps 724 and 726 as shown in FIG. 7, data acquisition begins, step 902, and a new data file is created to capture spiral data, step 904. Patient information, such as the patient's name, age, sex and clinical condition, etc., described above with respect to step 718, is then copied into the data file, step 906. The digitizing tablet is then polled, and X-position, Y-position and pressure data is collected, step 908, and saved to a corresponding buffer, step 910. If the data is deemed to be unacceptable, another attempt is made to collect the X, Y and pressure data, step 908. If the collected data is acceptable, the test subject is instructed to draw another spiral, step 914, if so desired. If the patient draws another spiral, the previously collected data are saved to the data file, step 918, and steps 904, 906, 908, 910, 912 and 914 are repeated. Once no more data is to be entered, data is saved according to step 916 and the data acquisition phase is completed, step 920.

Figure 10:
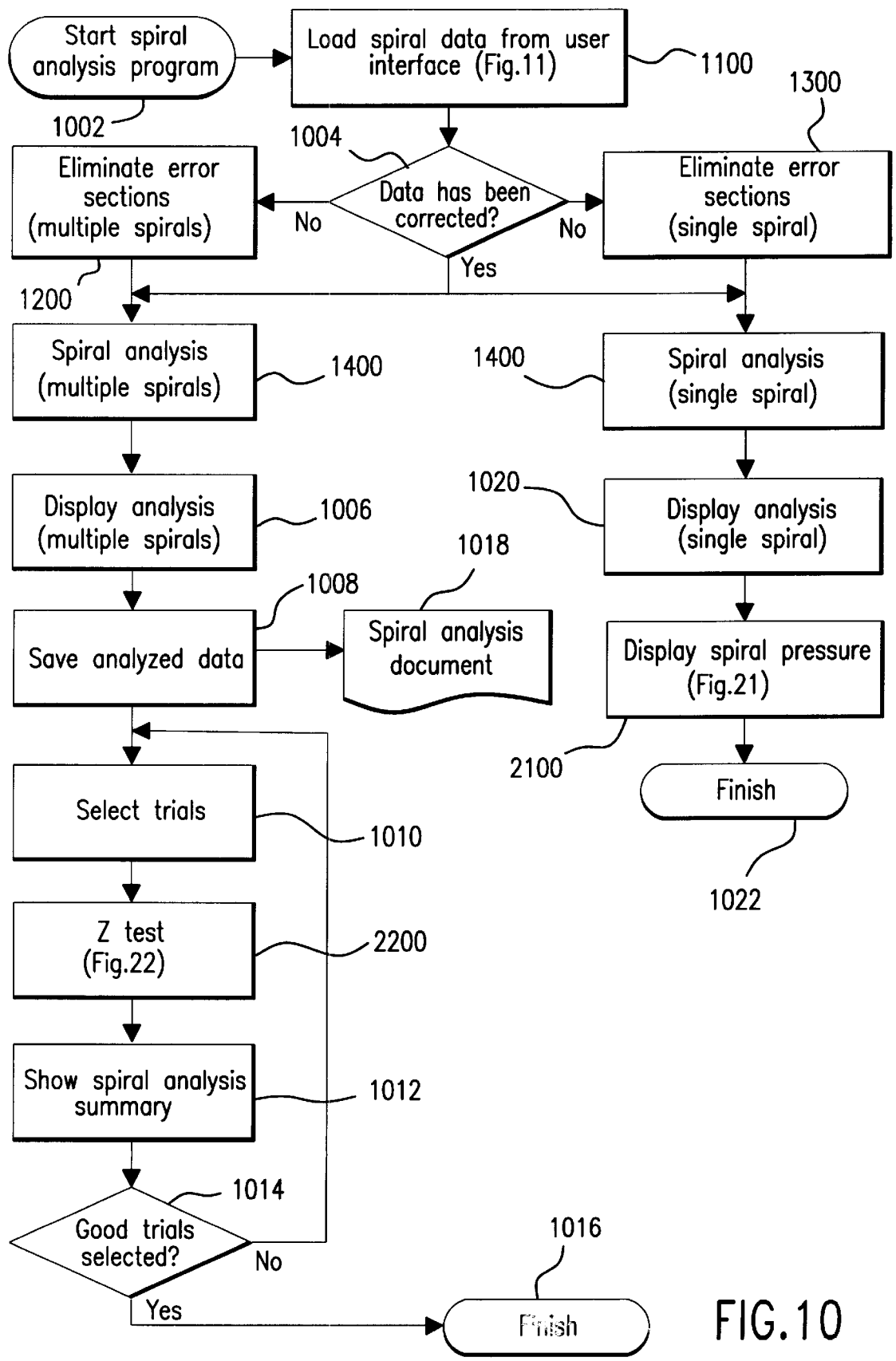
FIG. 10 is a flow chart showing a preferred method performed by the analysis module of FIG. 2.

FIG. 10 shows a preferred method 1000 performed by the analysis module of FIG. 2, and refers to methods depicted in greater detail in the flow charts of FIGS. 11, 12, 13, 14, 21 and 22, and described infra. After spiral data has been saved to the appropriate data file or files, the computerized analysis of the spiral data is initialized as shown by step 1002. Spiral data is then loaded from a user interface, step 1100, as described below with reference to FIG. 11.

Subsequent steps will depend upon whether the data relates to a single spiral or multiple spirals and whether or not, step 1004, the data is corrected.

Figure 13:
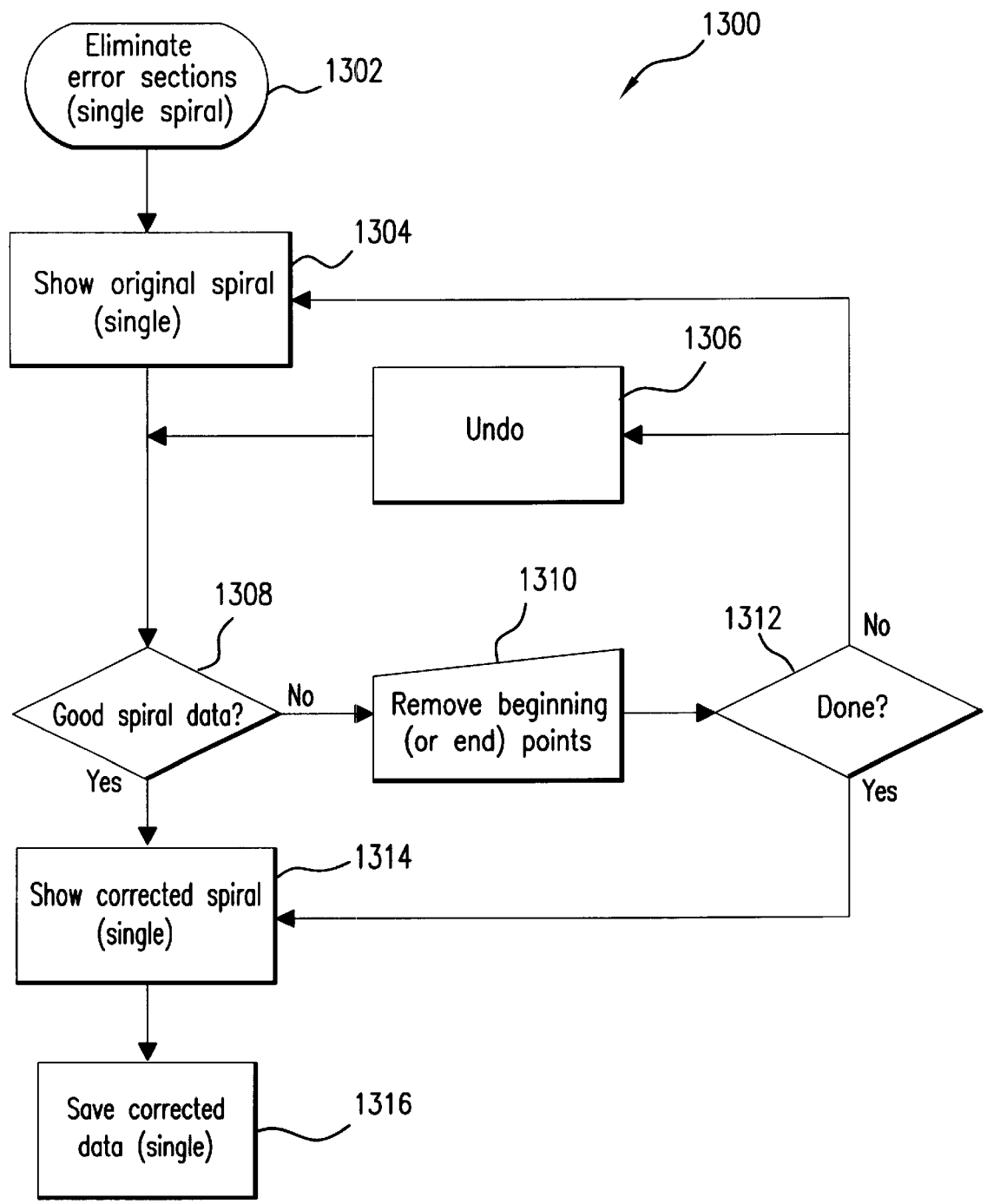
FIG. 13 is a flow chart showing a preferred method for manually eliminating error sections in accordance with the method of FIG. 10.

According to FIG. 10, if the data relates to a single spiral and has been corrected, it may be analyzed in step 1400 (FIG. 14); otherwise, the data is subjected to step 1300 to eliminate error sections, is depicted in FIG. 13. Once analysis has been performed, the results may be displayed, step 1020. Spiral pressure may also be displayed, step 2100, using steps depicted in FIG. 21, before the program for single spiral analysis finishes, step 1022.

Figure 12:
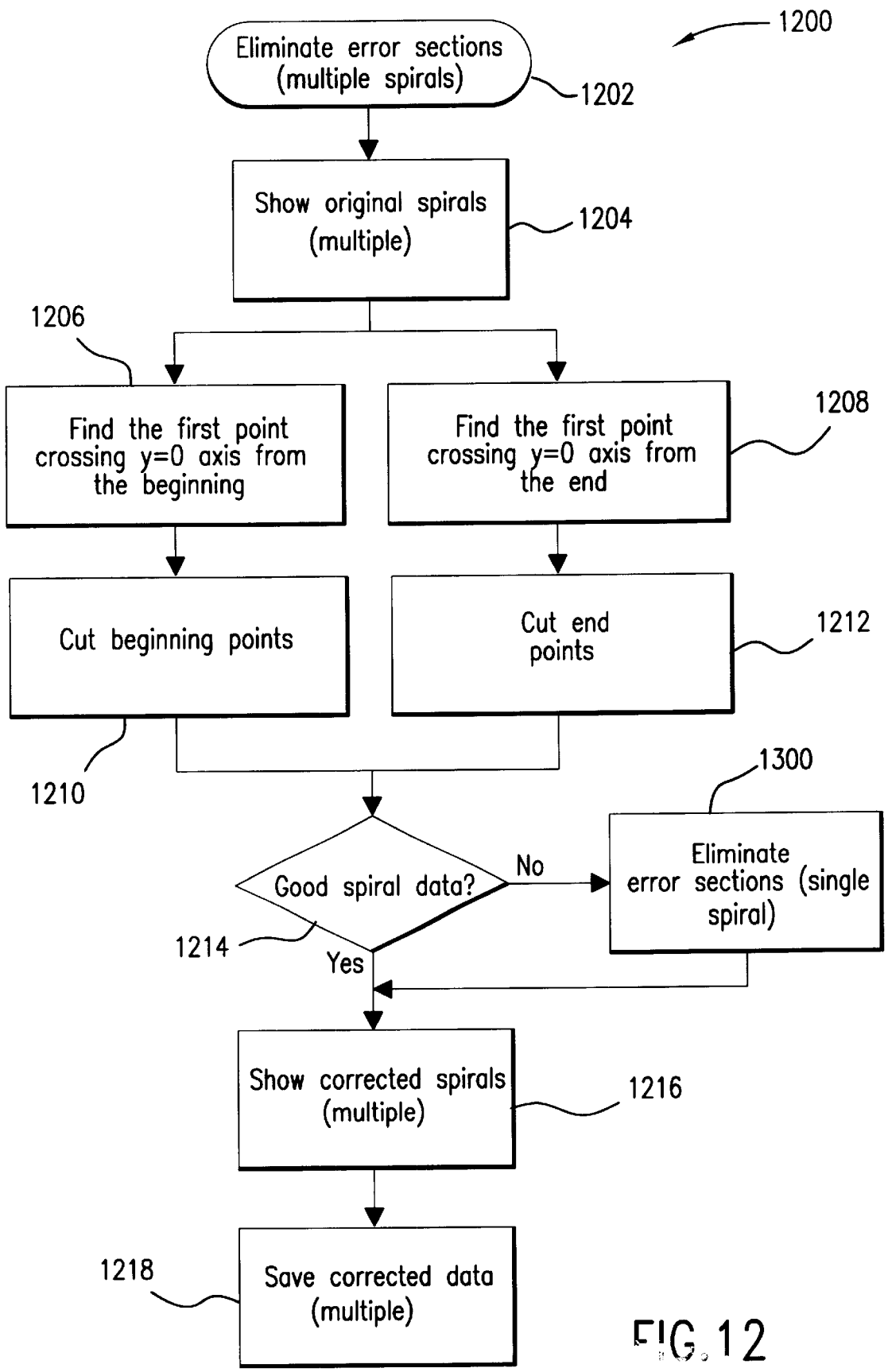
FIG. 12 is a flow chart showing a preferred method for automatically eliminating error sections in accordance with the method of FIG. 10.
Figure 14:
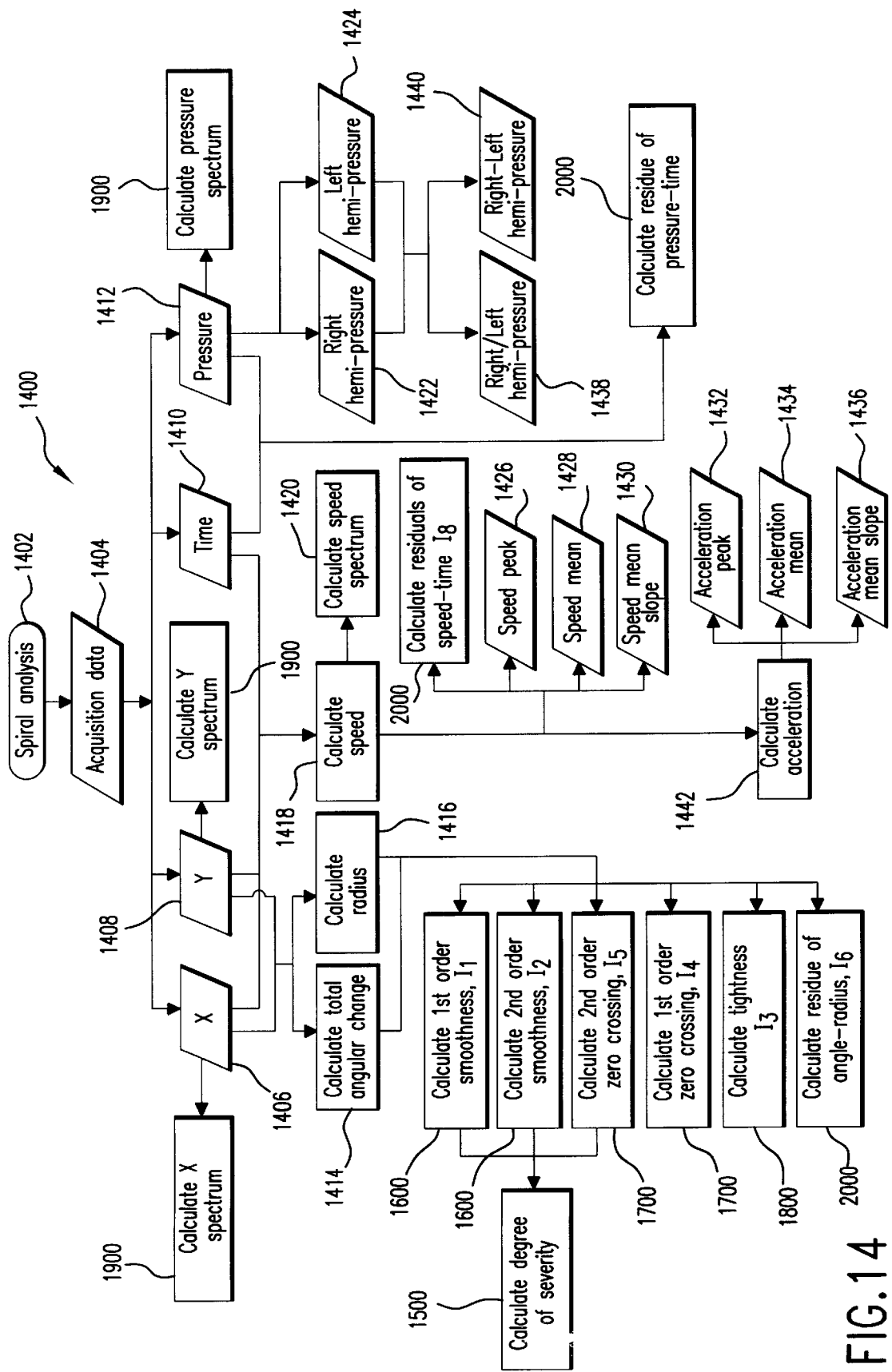
FIG. 14 is a flow chart showing a preferred method of analyzing a spiral in accordance with the method of FIG. 10.

Further according to FIG. 10, if the loaded data includes data for multiple spirals, then an automatic error section elimination procedure is performed, step 1200, as shown in FIG. 12, before the data is analyzed in step 1400 (FIG. 14). Once the multiple spiral data has been analyzed, it may be displayed, step 1006, saved, step 1008, and used to produce a spiral analysis document, step 1018. If a subset of trials in the data are to be analyzed, a set of trials may be selected, step 1010, and then subjected to the Z-test, step 2200 (FIG. 22) for hypothesis testing for the mean of current loaded data with known variance (normal data). A summary of spiral analysis of the selected trials may be shown, step 1012, and then it may be determined, step 1014, whether or not good trials had been selected for analysis. If it is determined that good trials had been selected, the program for multiple spiral analysis may finish, step 1016; otherwise, a new set of trials may be selected and subjected to Z-test analysis, step 2200 (FIG. 22), as set forth above, and the cycle repeated until a selection of good trials has been made.

Figure 11:
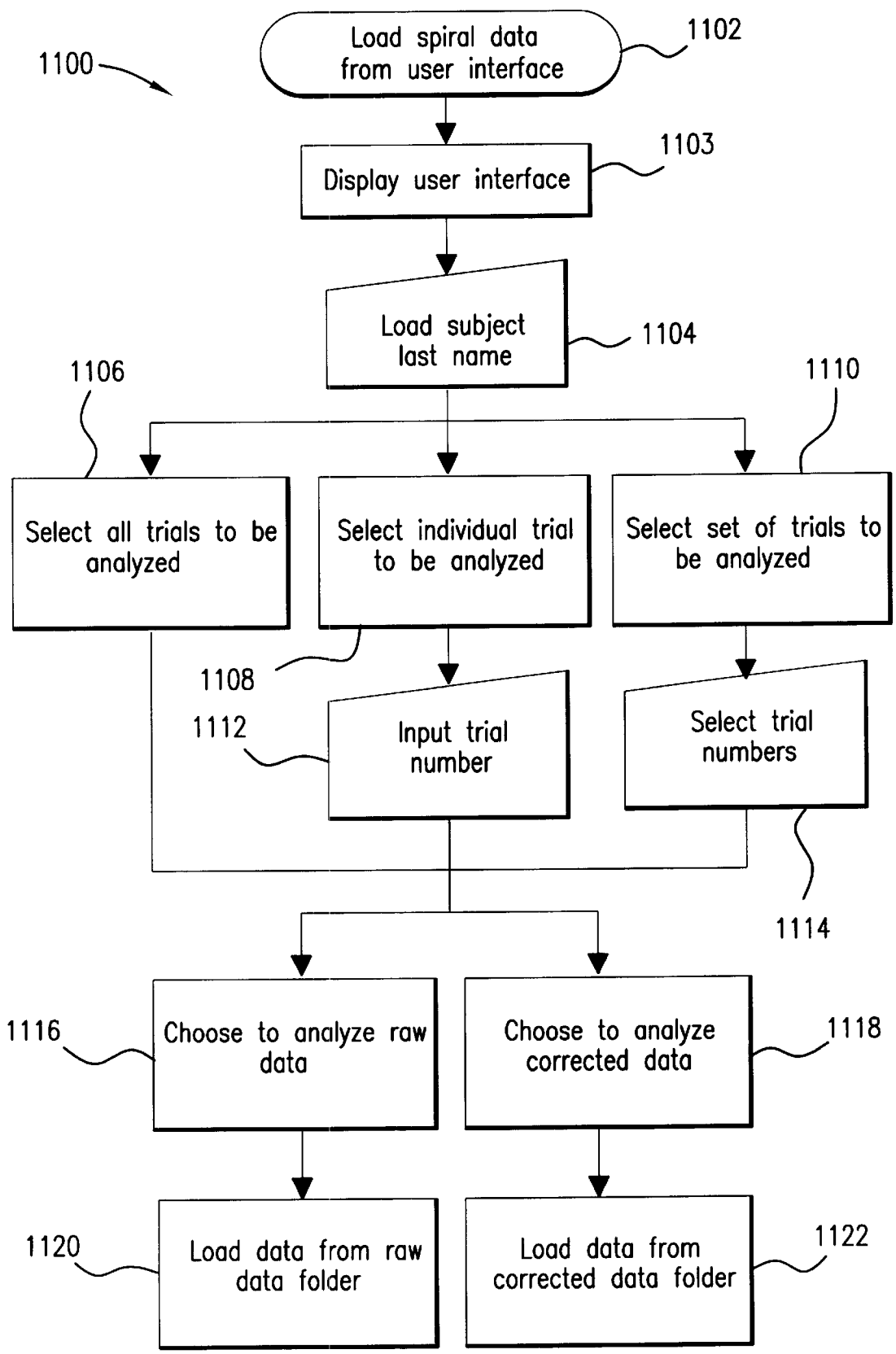
FIG. 11 is a flow chart showing a preferred method for loading data in accordance with the method of FIG. 10.

FIG. 11 is a flow chart showing a preferred method 1100 for loading data in accordance with the method of FIG. 10. In accordance with FIG. 11, the appropriate spiral data is loaded by displaying a user interface and entering the subject's last name, steps 1102, 1103 and 1104. The user then has the option of selecting all available trials, individual trials or a set of trials to be analyzed, steps 1106, 1108 and 1110, respectively. If an individual trial is selected, step 1108, then the user is asked to input the corresponding trial number, step 1112. If the user desires to select a specified set of trials to be analyzed, step 1110, then the user is asked to input the desired trial number, step 1114. After the selections are made, the user can choose to analyze raw data or corrected data according to steps 1116, 1120, 1118 and 1122.

FIG. 12 shows a preferred method 1200 for automatically eliminating error sections in accordance with the method of FIG. 10. This routine is initialized, step 1202, only when errors are to be eliminated in multiple spirals. As shown in FIG. 12, each of the original spirals are displayed to the user, step 1204, and checks are performed to find the first zero crossing points of the Y-axis (y=0) for each spiral with respect to the beginning points of each spiral, step 1206, and the first zero crossing of the Y-axis for each spiral with respect to the end points of each spiral, step 1208. Data occurring between the beginning of the spiral and the first Y-axis zero crossing from the beginning is deleted, step 1210, along with data occurring between the end of the spiral and the first Y-axis zero crossing from the end, step 1212. If the spiral data is determined to be satisfactory ("good"), step 1214, then the corrected spirals are displayed and saved to a file, steps 1216 and 1218, respectively. If the spiral data is unsatisfactory ("no good"), then error sections are eliminated on a spiral-by-spiral basis, step 1300, in accordance with the steps shown in FIG. 13.

A "good" spiral is one starting and ending at a Y-axis zero crossing. "Good" spiral data is defined as spiral data remaining after data occurring between the beginning (and/or end) and the first Y-axis zero crossing is deleted. Deletion of this data is often required because hand control is often diminished at the beginning and the end of the spiral. This diminished hand control, it has been found, in turn distorts the Y-axis zero-crossing of the spiral at the beginning and end of the spiral. Thus, in a preferred embodiment of the present invention, data corresponding to the beginning and/or end of the spiral is "edited-out."

FIG. 13 shows a preferred method 1300 for manually eliminating error sections in accordance with the method of FIG. 10. The error section elimination routine for single spirals is initiated for a single original spiral, step 1302. The original spiral is then displayed, step 1304. If the original spiral is good, step 1308, then it is displayed once again and saved to file, steps 1314 and 1316, respectively. If the original spiral is not good, then the spiral data is "edited" by removing beginning and/or end points of the spiral according to predefined parameters, step 1310. Upon completion of the "editing" step, step 1312, the operator is given an option to "undo" the edits made to the original spiral data, step 1306. If the corrected spiral data is determined to be good, step 1308, then the corrected data is displayed and saved according to steps 1314 and 1316.

In accordance with a preferred embodiment of the present invention, the user is allowed to select and delete "bad" portions of a spiral by selecting the corresponding Y-axis zero crossing. However, the spiral may be drawn so tightly that the user makes a mistake and thus selects the wrong point. The "undo" feature is thus provided for recovering any spiral portions that are deleted.

Figure 15:
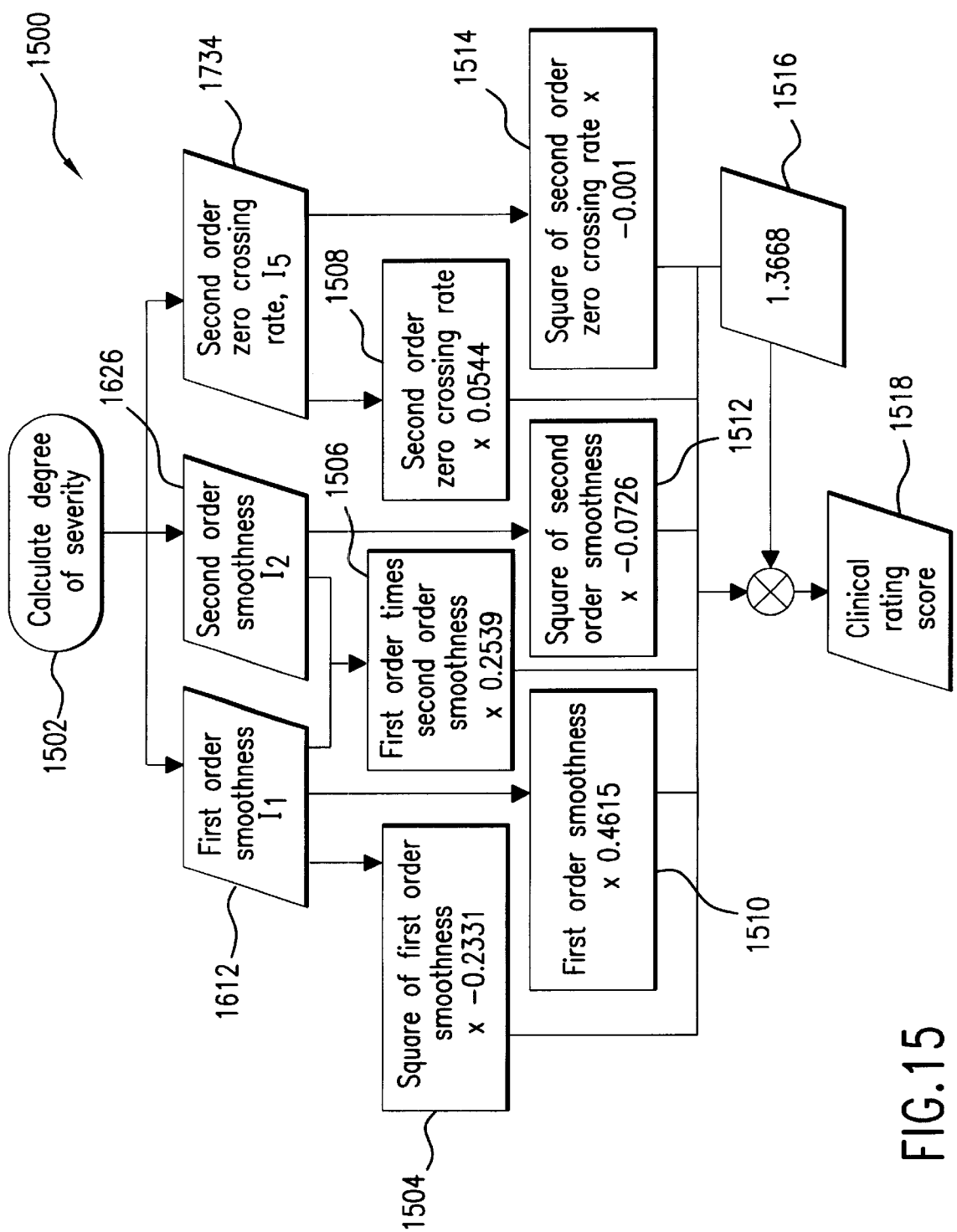
FIG. 15 is a flow chart showing a preferred method for determining a degree of severity in accordance with the method of FIG. 10.

FIG. 14 shows a preferred method 1400 for analyzing spiral data in accordance with the method of FIG. 10. The purpose of the spiral analysis again is to compute the degree of severity of motion disorder, step 1500 (see FIG. 15), and the various indices used to derive the degree of severity, e.g., steps 1600 and 1700 (see FIGS. 16 and 17). Although the spiral analysis method computes each of the indices shown above in Table 1, the present specific non-limiting embodiment of the spiral analysis method takes into account only the first order smoothness, index $I_1$, the second order smoothness, index $I_2$, and second order zero crossing rate, index $I_5$. The clinical rating score, also referred to as the degree of severity, is computed (step 1502) as shown in FIG. 15.

Referring again to FIG. 14, a spiral analysis routine is initialized, step 1402, and then the original or corrected data saved during data acquisition and error correction is accessed, step 1404. The spiral analysis then operates on the data, i.e., the time-stamped (1410) X-position (1406), Y-position (1408) and pressure (1412) data, as described below. The X and Y coordinates are used to calculate the following X-Y related parameters: the frequency spectrum of X and Y position, as determined in steps 1900. (see FIG. 19); the angular change of the spiral over time, step 1414; the radius of the spiral ($r=\sqrt{(X^2+Y^2)}$), step 1416; the speed at which the spiral is drawn, step 1418; and the speed spectrum 1420. Pressure readings are used to calculate the following pressure-related parameters: the frequency spectrum of pressure, step 1900; right hemi-pressure applied while drawing the spiral, step 1422; left hemi-pressure applied while drawing the spiral, step 1424; right/left hemi-pressure, step 1438, and right-left hemi-pressure, step 1440; and the residue of pressure-time, step 2000 (see FIG. 20). "Right/left hemi-pressure" is defined as the value of the right hemi-pressure divided by the value of the left hemi-pressure, and the "right-left hemi-pressure" is defined as the value of the right hemi-pressure subtracted by the value of the left hemi-pressure.

The X-position, Y-position and pressure parameters are then used to derive the indices shown above in Table 1. For example, the following indices are derived from the angular change, step 1414, and radius calculations, step 1416: first order smoothness ($I_1$), step 1600 (see FIG. 16); second order smoothness ($I_2$), step 1600 (see FIG. 16); tightness of the spiral (13), step 1800 (FIG. 18); first order zero crossing rate ($I_4$), step 1700 (see FIG. 17); second order zero crossing rate ($I_5$), step 1700 (see FIG. 17); and residue of angle-radius ($I_6$), step 2000 (see FIG. 20).

Figure 20:
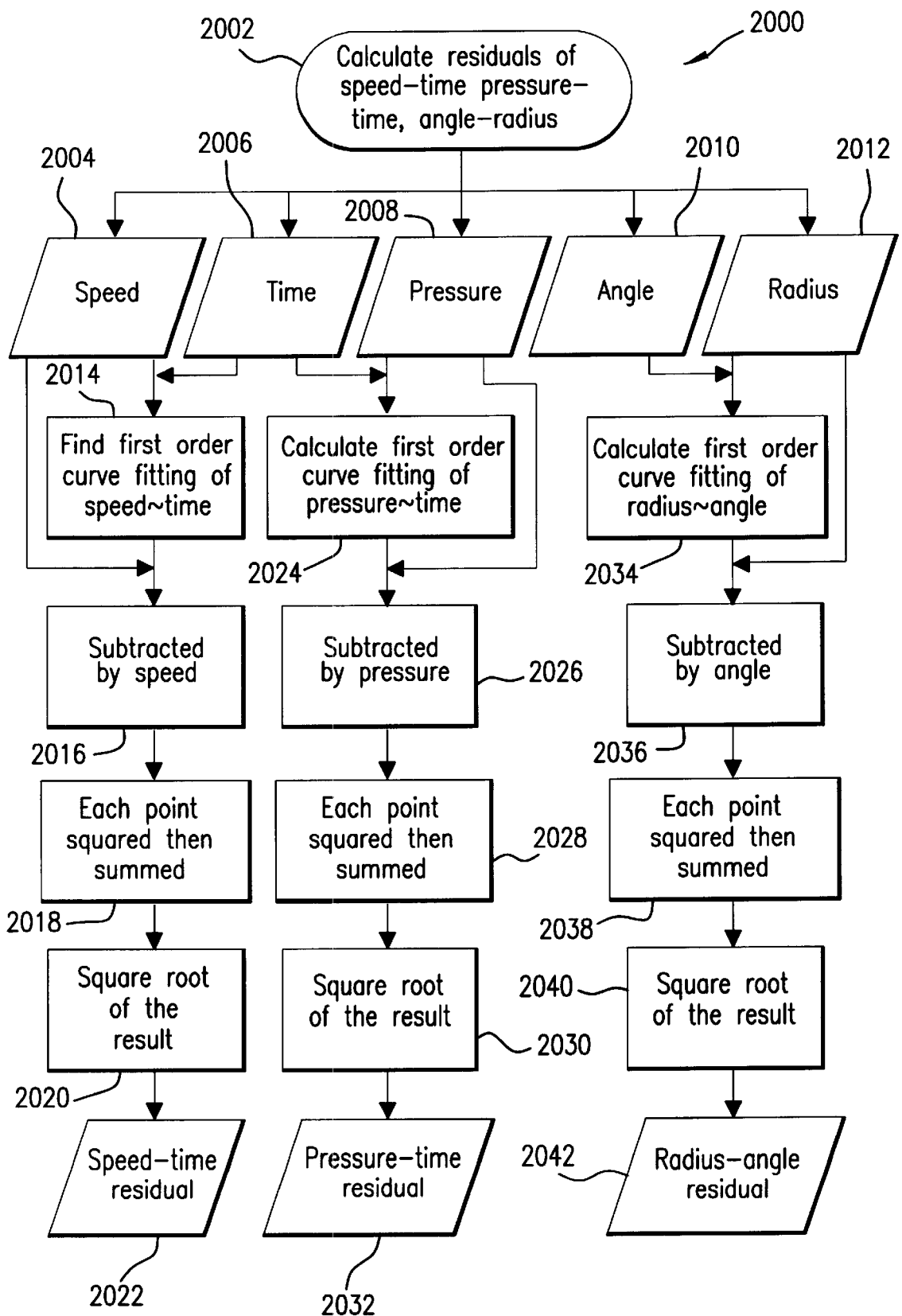
FIG. 20 is a flow chart showing a preferred method for computing speed-time, pressure-time and radius-angle residuals in accordance with the method of FIG. 10.

FIG. 14 further shows that the residuals of speed-time, index $I_8$, is computed from the calculated speed, step 2000 (FIG. 20). The following statistics are also computed from the calculated speed: the maximum speed, step 1426; the mean speed, step 1428; the speed mean slope, i.e., first order curve fitting slope of speed, step 1430; acceleration, step 1442; the maximum acceleration, step 1432; the mean acceleration (step 1434); and the acceleration mean slope, i.e., first order curve fitting slope of acceleration, step 1436.

FIG. 15 shows a preferred method for calculating (step 1502) a degree of severity (clinical rating score) in accordance with the method of FIG. 10. The degree of severity again is based on the computed values of the first order smoothness, second order smoothness and the second order zero crossing rate, indices $I_1$, $I_2$ and $I_5$. After indices $I_1$, $I_2$ and $I_5$ are computed to produce values 1612, 1626 and 1734, respectively (see FIGS. 16 and 17), the indices are processed in accordance with the derived clinical rating score (degree of severity) of Equation 1, steps 1504, 1506, 1508, 1510, 1512, 1514 and 1516 to yield the Clinical Rating Score, 1518 (also referred to herein as the "degree of severity").

Figure 16:
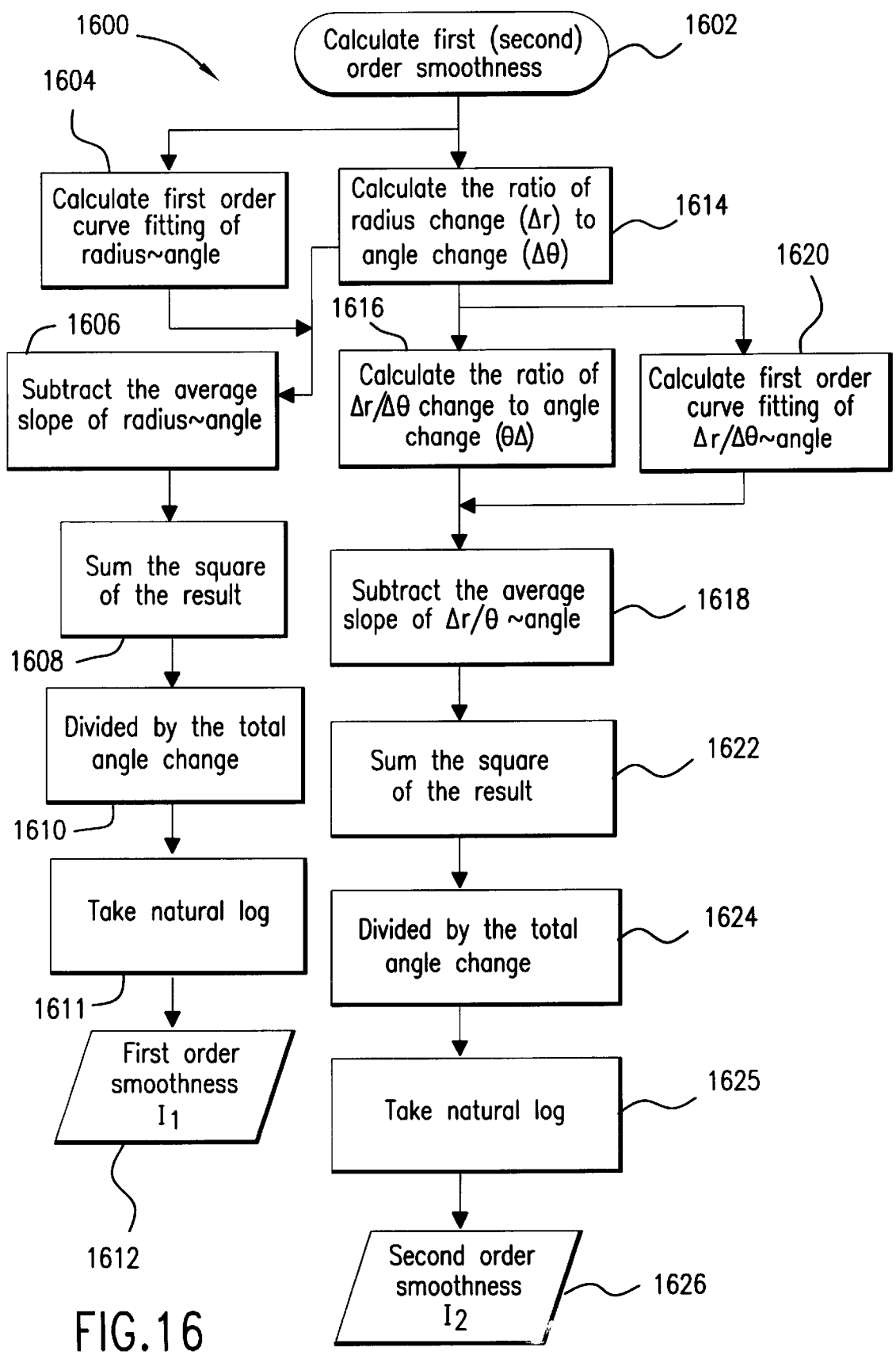
FIG. 16 is a flow chart showing a preferred method for computing a first order smoothness and second order smoothness of a handwritten spiral in accordance with the method of FIG. 10.

FIG. 16 shows a preferred method for computing a first order smoothness $I_1$ (1612) and second order smoothness $I_2$ (1626) of a handwritten spiral in accordance with the method of FIG. 10. The steps shown in FIG. 16 correspond to Equations 5 and 6 shown above.

Where first order smoothness is being calculated, the ratio of radius change ($\Delta r$) to angle change ($\Delta \theta$) is calculated, step 1614. Further, the first order curve fitting of radius versus angle is calculated, step 1604. In step 1606, the average slope determined in step 1604 (i.e., the first order curve fitting of radius versus angle) is subtracted from the ratio $\Delta r/\Delta \theta$ of step 1614. Step 1608 sums the square of the result of step 1606, and then the result of step 1608 is divided by the total angle change, step 1610. The first order smoothness $I_1$ (1612) is then calculated as the natural log (step 1611) of the result of step 1610.

To determine second order smoothness, the results of step 1614 are then used to calculate the ratio of $\Delta r/\Delta \theta$ change to angle change ($\Delta \theta$), step 1616, and to calculate the first order curve fitting of $\Delta r/\Delta \theta$ versus angle, step 1620. In step 1618, the average slope of $\Delta r/\theta$ versus angle (from step 1620) is subtracted from $\Delta r/\Delta \theta/\theta$. Step 1622 then sums the square of the result of step 1618. In step 1624, the result of step 1622 is divided by the total angle change. To determine the second order smoothness $I_2$ (1626), the natural log of the result of step 1624 is calculated, step 1625.

Figure 17:
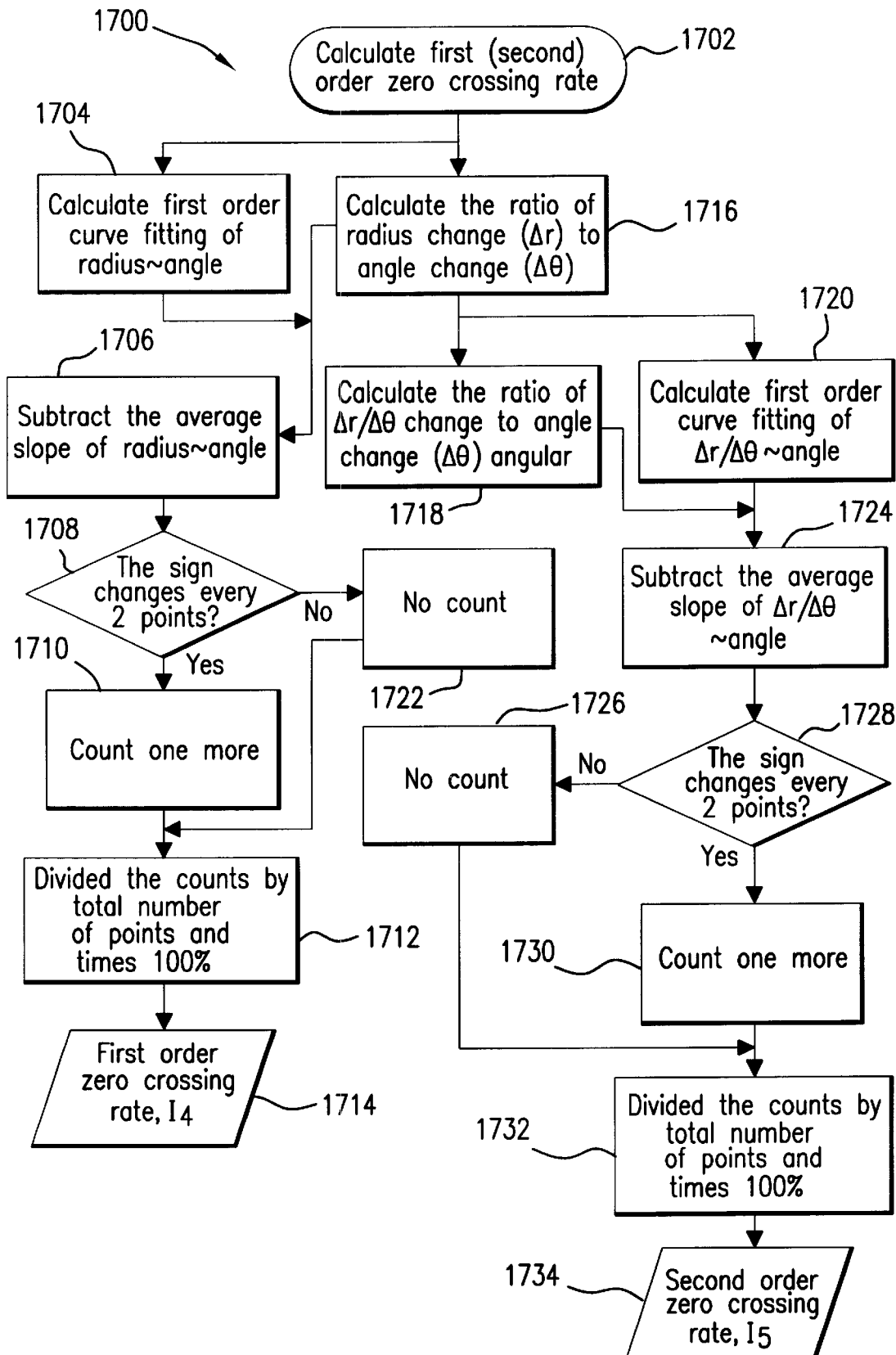
FIG. 17 is a flow chart showing a preferred method for computing a first order zero-crossing rate and a second order zero-crossing rate of a handwritten spiral in accordance with the method of FIG. 10.

FIG. 17 shows a preferred method 1700 for computing a first order zero-crossing rate and a second order zero-crossing rate of a handwritten spiral in accordance with the method of FIG. 10.

To calculate the first order zero crossing rate $I_4$ (see Equation (7)), the ratio of the radius change ($\Delta r$) to angle change ($\Delta \theta$) is calculated, step 1716. A first order curve fitting of the radius versus angle is then performed, step 1704. In step 1706, the average slope of the curve determined in step 1704 is subtracted from the result from step 1716. If (step 1708) the sign of the result from step 1706 changes every two points, then the count is incremented by one, step 1710, and divided by the total number of data points collected and multiplied by 100%, step 1712. This yields the first order zero-crossing rate $I_4$ (1714). If, in step 1708, the sign does not change every two points, then the count is not incremented (step 1722) and one proceeds to step 1712.

The computation of the second order zero-crossing rate $I_5$ (see Equation (8)) is similar, but involves an extra step, step 1718, to calculate the second order rate of change of the radius versus angle, namely the ratio of $\Delta r/\theta$ to $\Delta \theta$. The first order curve fitting of $\Delta r/\Delta \theta$ versus angle is calculated, step 1720, and then the average slope from step 1720 is subtracted from the result of step 1718, step 1724. If (step 1728) the sign of the result from step 1724 changes every two points, then the count is incremented by one, step 1730, and then divided by the total number of data points collected and multiplied by 100%, step 1732. This yields the second order zero-crossing rate $I_5$ (1734). If, in step 1728, the sign does not change every two points, then the count is not incremented (step 1726) and one proceeds to step 1732.

Figure 18:
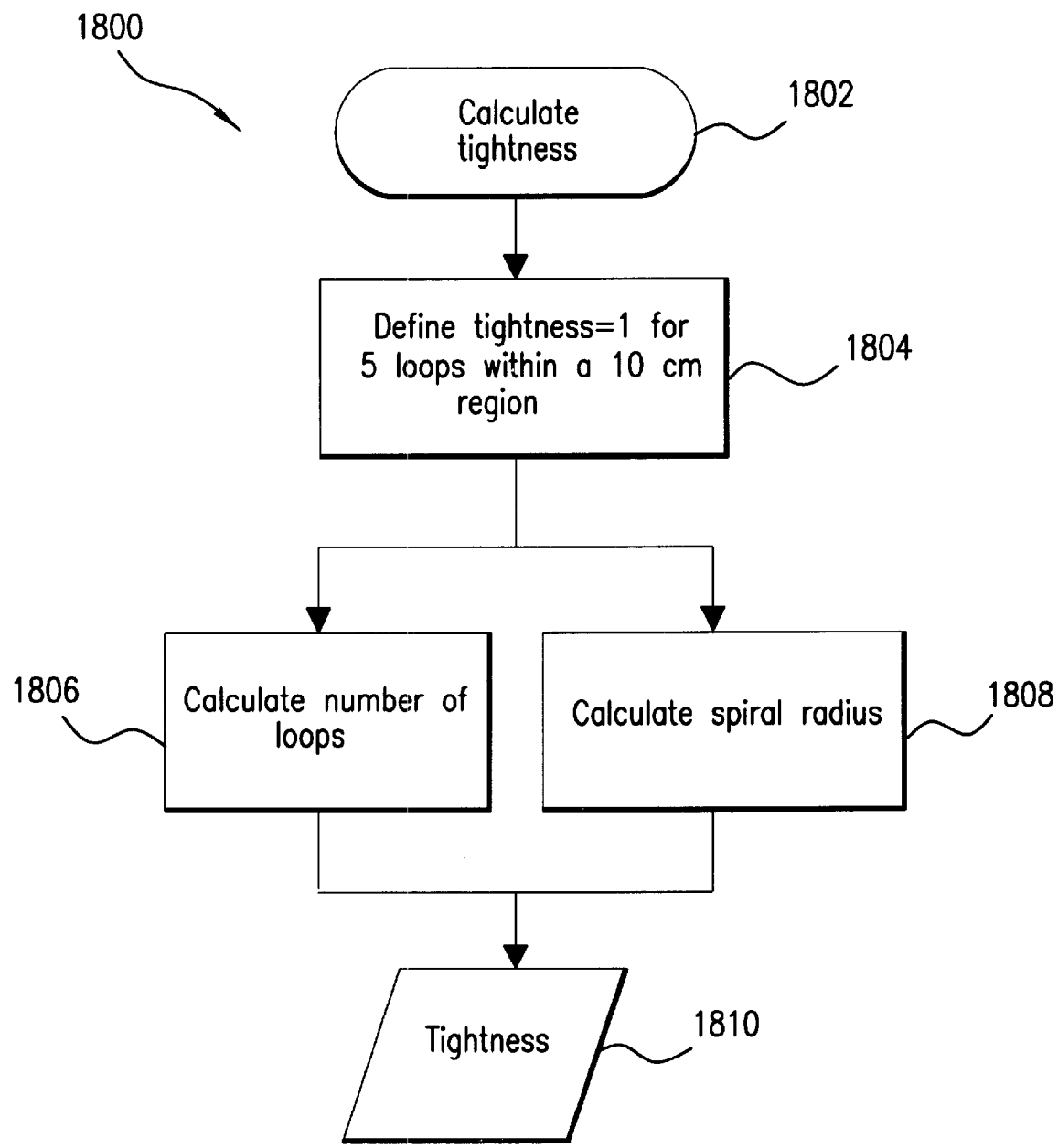
FIG. 18 is a flow chart showing a preferred method for characterizing the tightness of a handwritten spiral in accordance with the method of FIG. 10.

FIG. 18 shows a preferred method for characterizing the tightness of a handwritten spiral in accordance with the method of FIG. 10. To calculate spiral tightness (step 1802), a "tightness" value of 1 is defined (step 1804) when 5 loops are contained within a 10 cm region extending from the center of the spiral. A tightness value of 1 is assigned when a patient draws a spiral having five loops within a 10 cm region. If a patient draws, for example, only three loops within a 10 cm region, the spiral is less tight and the tightness value equals 0.6. The number of loops is calculated as the total angle change divided by $2\pi$, step 1806, and the maximum radius of the spiral is measured, step 1808. Then, tightness is calculated as the number of loops divided by the maximum radius, step 1810 (see also Equation (9)).

Figure 19:
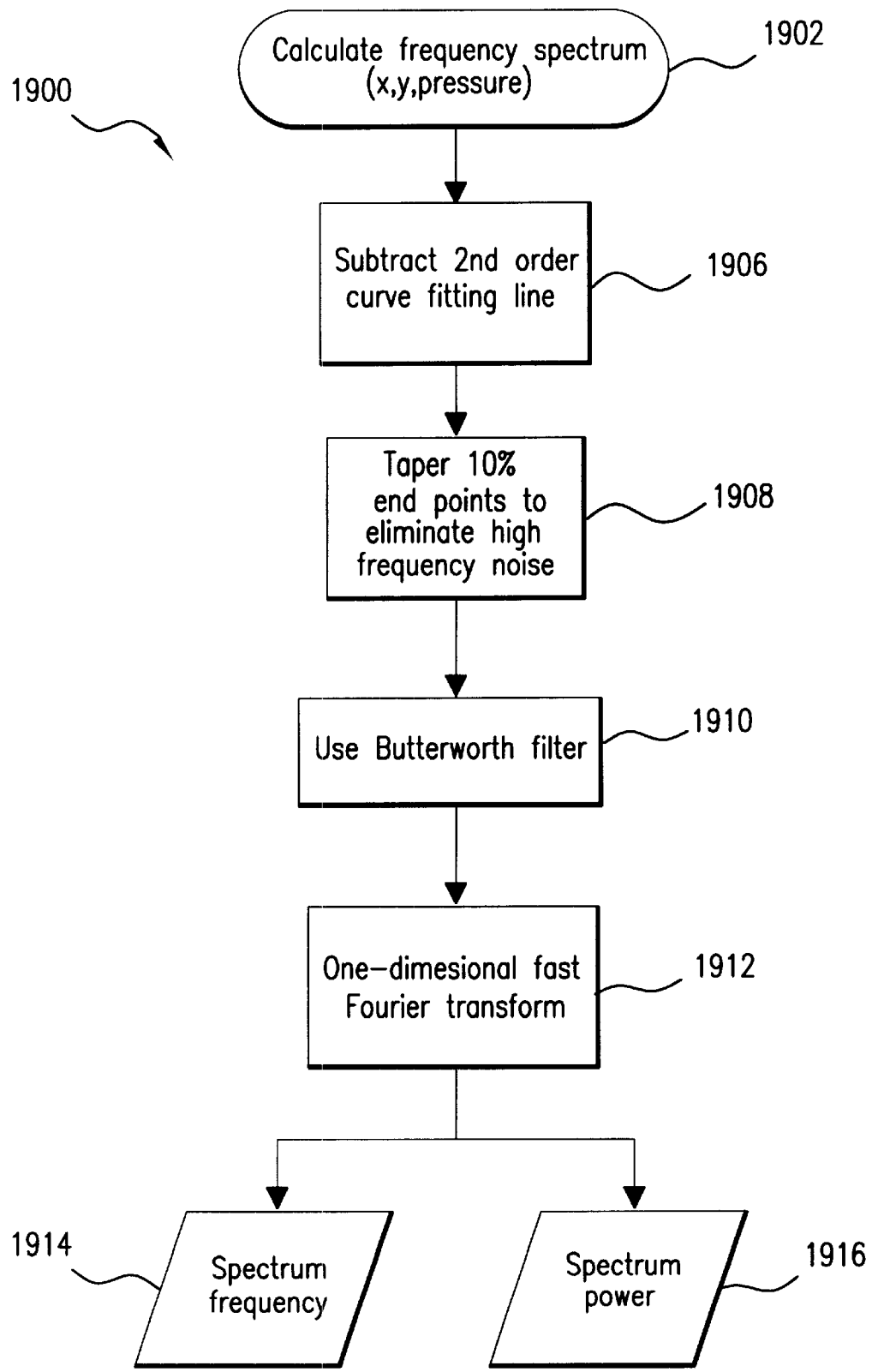
FIG. 19 is a flow chart showing a preferred method for performing a spectral analysis of X-position, Y-position and pressure data in accordance with the method of FIG. 10.

FIG. 19 is a flow chart showing a preferred method (1900) for performing a spectral analysis of X-position, Y-position and pressure data in accordance with the method of FIG. 10. Since a primary objective is to characterize the spectrum data caused by tremor, several spectrum analysis techniques are utilized. Most pressure data increases with the spiral radius and creates a high power low frequency peak. To ignore this spectrum, the curve fitting points for X-position, Y-position and pressure are subtracted (step 1906) from the measured X-position, Y-position and pressure data, step 1902. To avoid high frequency noise caused by the discontinuity of selected points, e.g., "leaking" effect of the FFT, the last 10% of end points are so-called "tapered" or eliminated in accordance with step 1908. In addition, it has been found that X-position, Y-position and pressure data has a basic low frequency component related to spiral loop execution, e.g., if a spiral has five loops drawn over five seconds, a 1 Hz frequency component appears in spectral analysis. Accordingly, a Butterworth filter is used to filter out this low component, step 1910. Next, as shown by step 1912, a fast Fourier transform (FFT) is performed on the data resulting from step 1910 with the number of points equal to a power of 2 These operations result in values for the spectrum frequency (1914) and spectrum power (1916).

FIG. 20 is a flow chart showing a preferred method 2000 for calculating residuals, step 2002, of speed-time, pressure-time and angle-radius, using measured values for speed (2004), time (2006), pressure (2008), angle (2010) and radius (2012) in accordance with the method of FIG. 10. To compute the speed-time residual, the time-stamped speed information is used to compute the first order curve fit of speed versus time, step 2014. Each of the actual speed values are then subtracted from each of the corresponding curve-fitted values, step 2016. The results are squared and then summed, step 2018, and the square root computed, step 2020, to derive the speed-time residual (2022).

To compute the pressure-time residual, the time-stamped speed information is used to compute the first order curve fit of pressure versus time, step 2024. Each of the actual pressure values are then subtracted from each of the corresponding curve-fitted values, step 2026. The results are squared and then summed, step 2028, and the square root computed, step 2030, to derive the pressure-time residual (2032)

To compute the radius versus angle residual, angle and radius measurements are used to compute the first order curve fit of radius versus angle, step 2034. Each of the actual angle values are then subtracted from each of the corresponding curve-fitted values, step 2036. The results are squared and then summed, step 2038, and the square root computed, step 2040, to derive the radius-angle residual (2042).

Figure 21A:
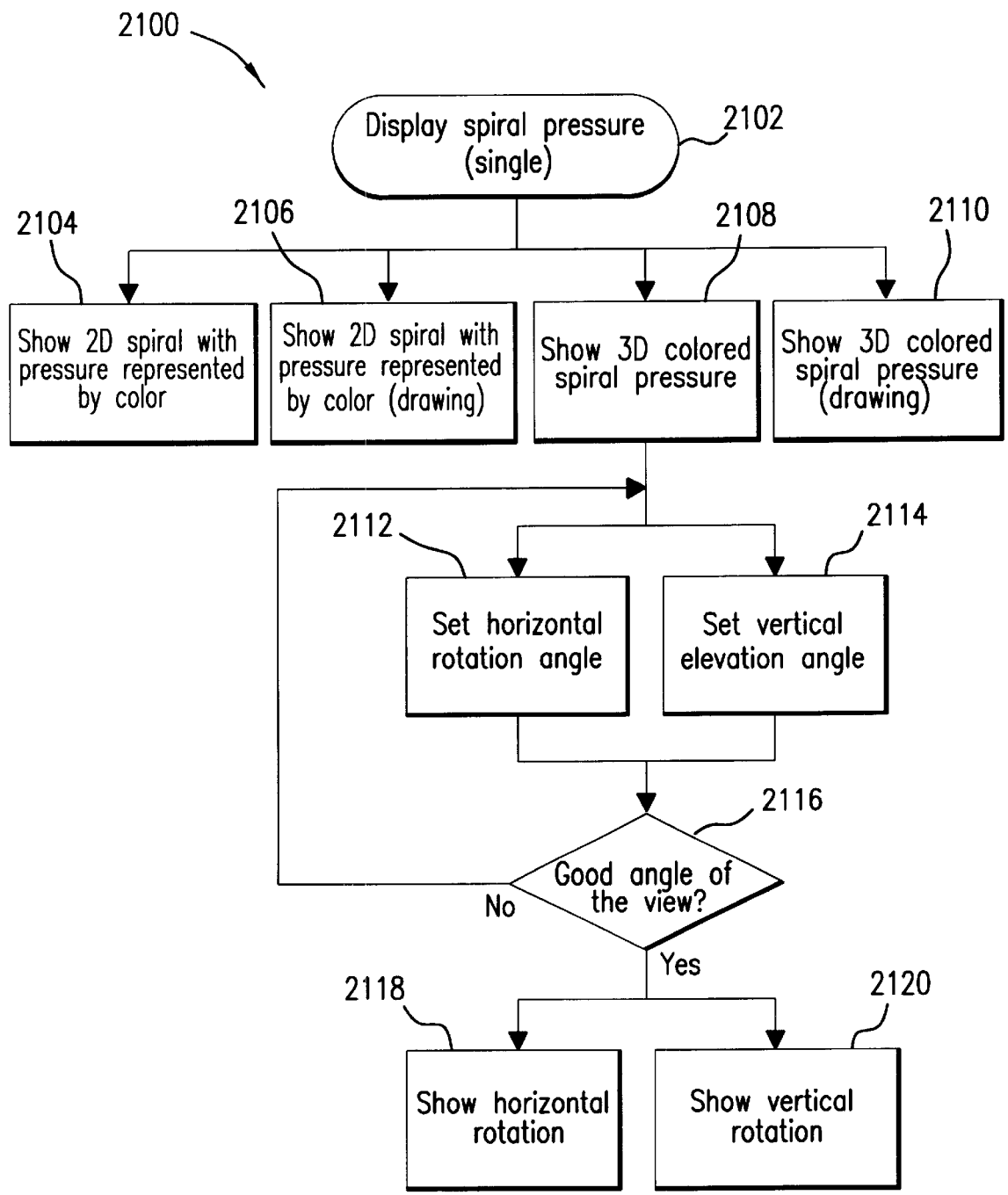
FIG. 21A is a flow chart corresponding to the acquisition module of FIG. 2.
Figure 21B:
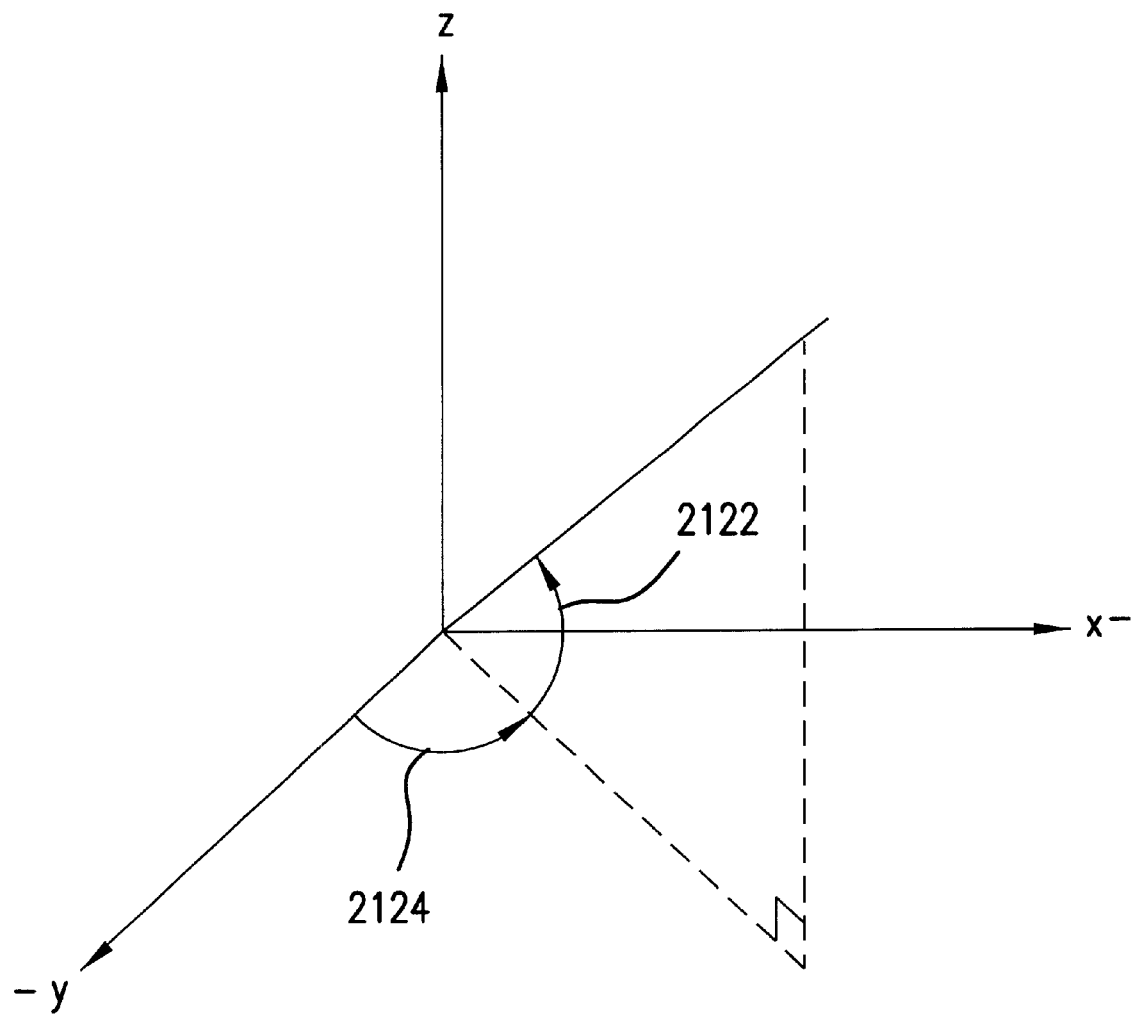
FIG. 21B defines the vertical elevation angle 2122 set according to step 2114 in FIG. 21A and the horizontal rotation angle 2124 set in step 2112 of FIG. 21A.

FIG. 21A is a flow chart (2100) showing a preferred method (2102) for displaying spiral pressure in accordance with the method of FIG. 10. "Still" (2104 and 2108) and animated (2106 and 2110) 2-D and 3-D spirals, wherein different pressure levels are represented by different colors, are examples of spiral pressure displays generated by the preferred method of FIG. 21A. 2-D animation reproduces the spiral drawn by the patient in real-time. To show an animated 3-D spiral, the patient can set the horizontal rotation or vertical elevation angle, and then rotate the spiral horizontally or vertically. According to steps 2112 and 2114, the horizontal rotation and vertical elevation angles are set, representing variables 2124 and 2122, respectively, as depicted in FIG. 21B. It is then determined whether the settings provide a good angle of the view, step 2116, and if so, horizontal rotation and vertical rotation are shown, steps 2118 and 2120, respectively.

Figure 22:
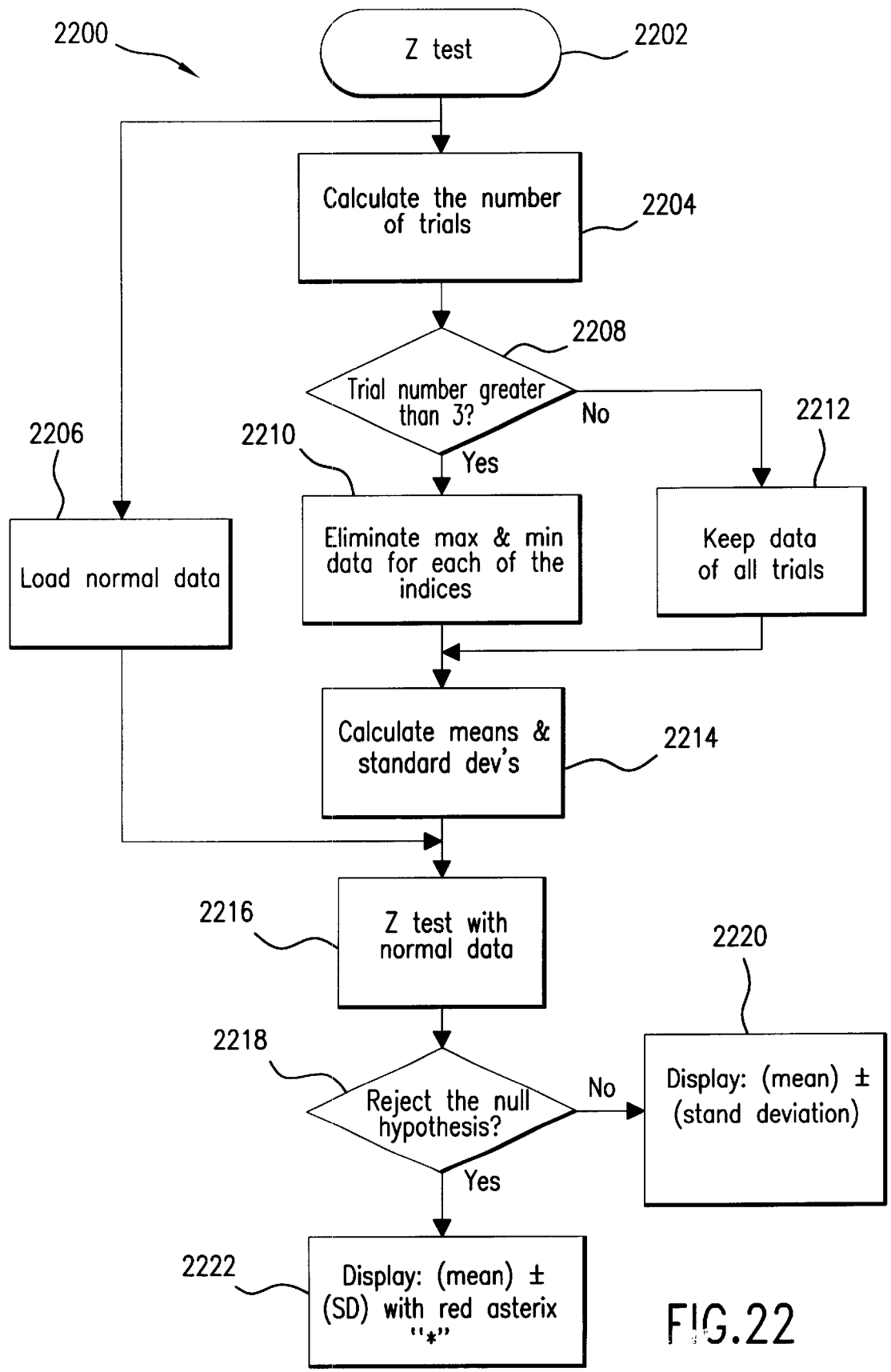
FIG. 22 is a flow chart corresponding to the acquisition module of FIG. 2.
Figure 23C:
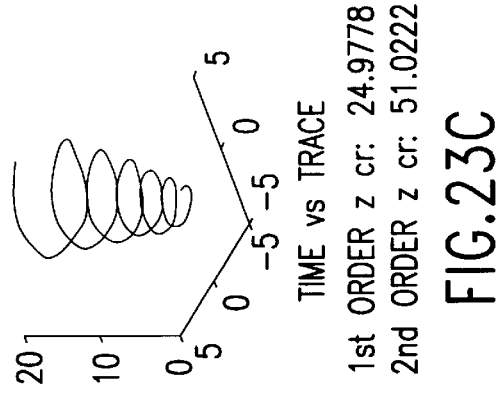
Figure 23B:
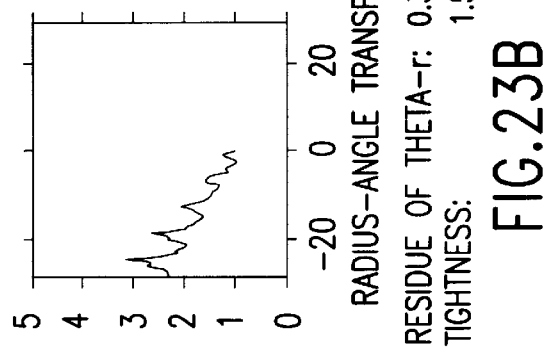
Figure 23A:
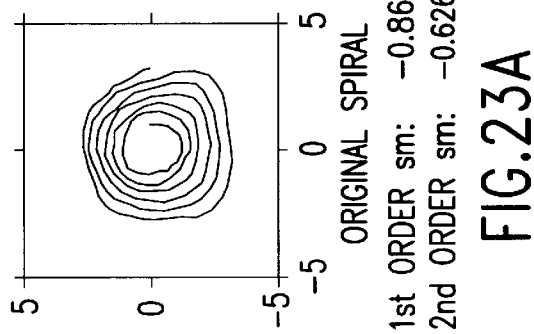
Figure 23F:
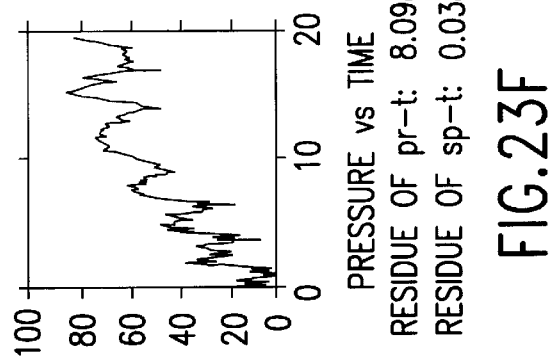
Figure 23E:
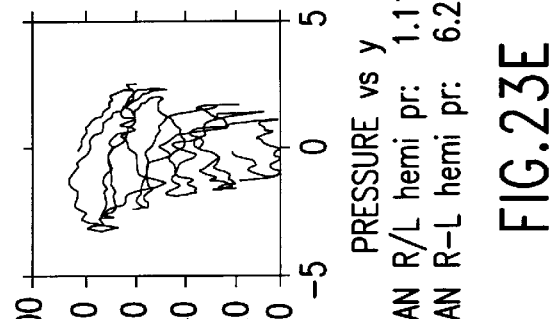
Figure 23D:
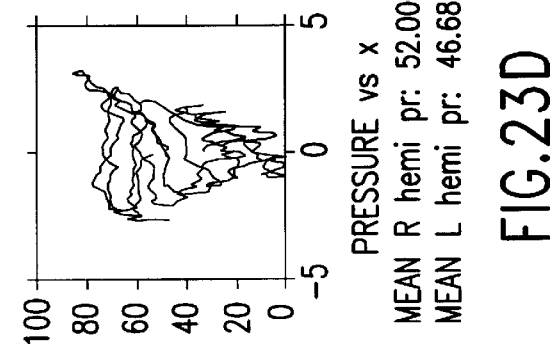
Figure 25C:
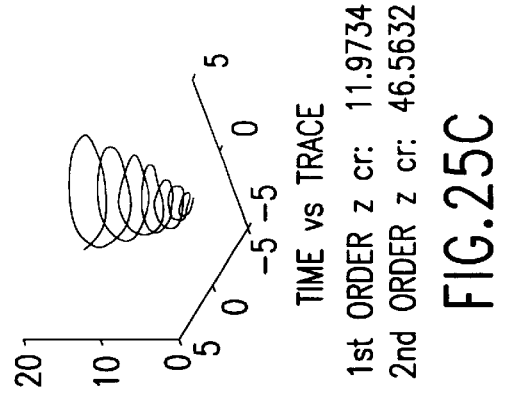
Figure 25B:
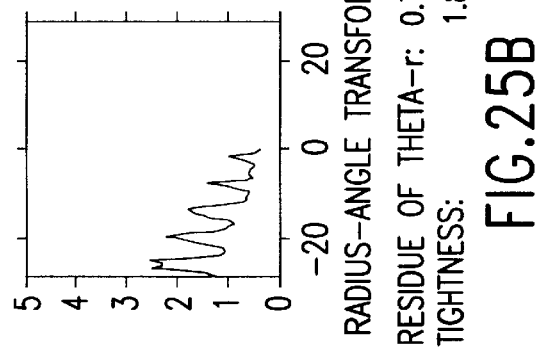
Figure 25A:
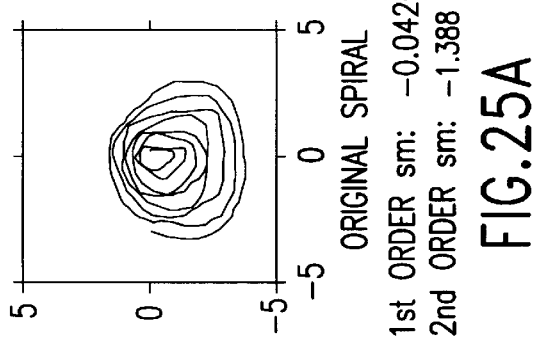
Figure 25F:
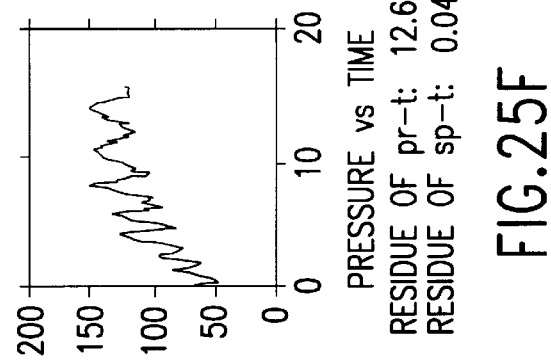
Figure 25E:
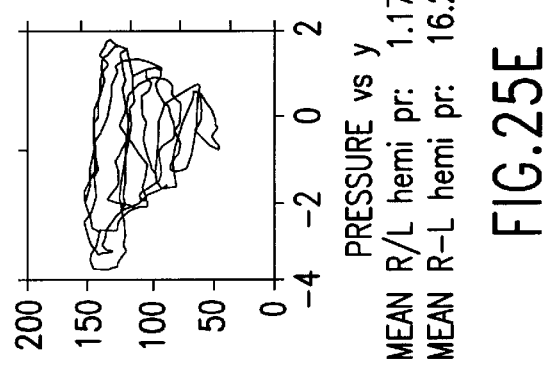
Figure 25D:
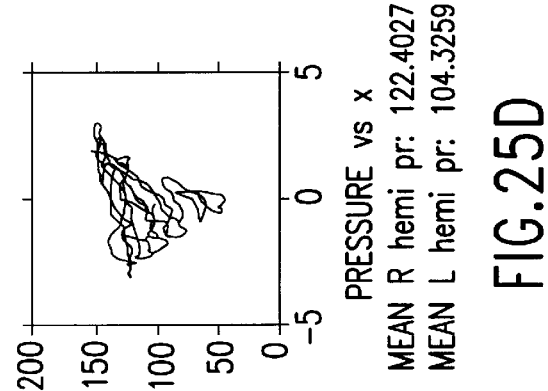

FIG. 22 is a flow chart (2200) showing a preferred nonlimiting method (2202) for performing a Z-test in accordance with the method of FIG. 10. First, the number of trials collected from one patient is obtained, step 2204. If (step 2208) this number is greater than 3 (for each hand), the maximum and minimum data are discarded for each index, step 2210. However, if there are only 3 (or less) trials for each hand, all the data is used (step 2212) in the Z-test. The means and standard deviations are calculated from the chosen data, step 2214. Comparing the results of the Z test using trial data, step 2216, with normal age-matched data loaded in step 2206, it is determined whether the data of every index rejects the null hypothesis or not, step 2218. Rejecting the null hypothesis (step 2222) implies that data does not belong to the group of normals, and data mean and standard deviation may be displayed with a special notation, such as, for example, a red asterisk (meaning it is significantly different from the normal). Accepting the null hypothesis (step 2220) indicates that the data falls within normal limits.

The present invention is further illustrated by the following working examples, presented to more clearly describe the invention but not by way of limitation.

EXAMPLE

EVALUATION OF A PARKINSON'S DISEASE PATIENT

FIGS. 23 through 28 illustrate test results, both graphically and numerically, for a 55 year-old right handed male (whose name has been redacted) who has been treated for Parkinson's Disease for three years, and who was evaluated by spiral analysis using the above-described methods. The subject was asked to draw 10 spirals with his right hand, and 10 spirals with his left hand, on a Kurta digitizing tablet, e.g., "Draw 10 spirals with each hand starting from the center 'x' and stop before you reach the outer boundaries." The outer boundaries defined a 10 cm×10 cm square. While drawing, the patient was comfortably seated with respect to the digitizing tablet without being subjected to any physical restraints, such as a harness, electrode wires, or other attachments that might hinder the patient's ability to draw the requested spirals. Further, the patient was not subject to any intimidating or invasive stimuli that would make him feel uneasy or uncomfortable while drawing the spirals.

FIGS. 23A–L through 25A–L depict three spirals drawn by the subject using his right hand, and FIGS. 26A–L through 28A–L depict three spirals drawn by the subject using his left hand, which are the first, fifth and tenth of the series of ten spirals drawn for each hand. The figures each have 12 subpart designated A–L, which depict, respectively, (A) the original spiral; (B) the radius—angle transform; (C) time vs. trace; (D) pressure vs. X; (E) pressure vs. Y; (F) pressure vs. Time; (G) X spectrum; (H) Y spectrum; (I) pressure spectrum; (J) speed; (K) speed spectrum; and (L) acceleration. In the upper right hand corner of each of FIGS. 23–28 is the degree of severity calculated using Equation (1) for that test. Various indices are set forth in each figure, as collected in Tables 5–7 below. In Table 5–7, right hand (e.g., "RH1") and left hand (e.g., "LH1") samples are provided along with statistical measures (e.g., mean, standard deviation, etc.) for each of the indicated indices or measured parameters. Columns labeled "(2)" in Tables 5–7 (e.g., "$I_1(2)$") indicate measurements wherein outliers, i.e., maximum and minimum data points, have been omitted. A summary of the results is presented in Table 4.

For three of the ten spirals drawn by the patient's right hand shown in FIGS. 23–25, the Clinical Rating Score (also referred to as the "degree of severity") was calculated to be, respectively (rounded to three significant figures), 1.15, 1.20 and 1.65. For three of the ten spirals drawn by the patient's left hand shown in FIGS. 26–28, the Clinical Rating Scores were 1.44, 1.44, and 1.83. As shown in Table 4, the summary results for all trials performed by this patient include average Clinical Rating Scores of 1.230±0.089 for his right hand and 1.504±0.135 for his left hand. These scores indicate that the patient exhibits mildly abnormal motor function and are consistent with other features of the patient's clinical condition. The slightly poorer scores of spirals drawn by the patient's left hand is likely due in part to the fact that the patient is right-handed. Beyond this explanation, however, the results further show that the R/L hemi-pressure ratio is slightly favored towards the right side of each spiral drawn by the subject. This confirms that the subject has a slight relative weakness on the left side. This disparity in the pressure exerted by the subject on the right versus left half of the drawn spirals ("hemi-spirals") was previously noted by the inventor as a distinguishing feature of Parkinson's Disease as opposed to other motor disorders such as essential tremor. Therefore, the fact that the patient suffers from left-sided weakness also probably contributed to the poorer execution of spirals drawn by his left hand.

TABLE 4

Example of Spiral Analysis Summary
Clinical Motor Physiology Laboratory
SPIRAL ANALYSIS SUMMARY
Date of study: xxxxxxxxx
Patient name: xxxxxxxxx
Dominant hand: Right
Clinical: Tr × 3 yrs., worse in action

|  | Dominant | | Non-dominant | |
| --- | --- | --- | --- | --- |
| (Average ± SD) | Patient | Normal | Patient | Normal |
| Degree of Severity: | 1.230 ± 0.089 | 0.333 ± 0.275 | 1.504 ± 0.135 | 0.581 ± 0.321 |
| Peak frequencies: | | | | |
| X | 0.881 ± 0.163 | 0.760 ± 0.125 | 0.900 ± 0.234 | 0.809 ± 0.201 |
| Power | 0.001 ± 0.000 | 0.002 ± 0.001 | 0.001 ± 0.005 | 0.002 ± 0.001 |
| Y | 0.887 ± 0.228 | 0.778 ± 0.161 | 3.122 ± 1.859 | 0.883 ± 0.356 |
| Power | 0.001 ± 0.000 | 0.002 ± 0.001 | 0.007 ± 0.005 | 0.003 ± 0.002 |
| Pressure | 2.559 ± 2.270 | 0.777 ± 0.334 | 0.461 ± 0.095 | 0.870 ± 0.625 |
| Power | 0.035 ± 0.024 | 0.017 ± 0.015 | 0.014 ± 0.007 | 0.029 ± 0.040 |
| Speed average: | 5.580 ± 0.504 | 8.954 ± 3.014 | 5.276 ± 0.262 | 8.821 ± 2.831 |
| Pressure-time res.: | 11.027 ± 1.199 | 10.307 ± 4.336 | 13.261 ± 2.340 | 12.212 ± 5.520 |
| Tightness: | 1.977 ± 0.224 | 1.266 ± 0.332 | 1.676 ± 0.195 | 1.140 ± 0.299 |
| R/L hemi-pres. ratio | 1.196 ± 0.031 | 1.052 ± 0.179 | 1.225 ± 0.038 | 0.906 ± 0.132 |

TABLE 5

|  | DOS (1) | DOS (2) | $I_1$ (1) | $I_1$ (2) | $I_2$ (1) | $I_2$ (2) | $I_1$ (1) | $I_1$ (2) | $I_1$ (1) |
| --- | --- | --- | --- | --- | --- | --- | --- | --- | --- |
| RH1 | 1.1548 | 1.1548 | −0.8619 | −0.8619 | −0.62683 |  | 1.5914 |  | 24.9778 |
| RH2 | 1.1778 | 1.1778 | −0.64614 | −0.64614 | −1.2811 | −1.2811 | 2.1588 | 2.1588 | 12.6984 |
| RH3 | 1.2008 | 1.2008 | −0.90647 | −0.90647 | −1.8008 | −1.8008 | 2.143 | 2.143 | 16.5195 |
| RH4 | 1.3396 | 1.3396 | −0.10198 | −0.10198 | −1.3518 | −1.3518 | 1.7449 | 1.7449 | 10.4053 |
| RH5 | 1.2053 | 1.2053 | −0.45788 | −0.45788 | −1.7007 | −1.7007 | 1.7114 | 1.7114 | 14.2282 |
| RH6 | 1.2777 | 1.2777 | −0.36082 | −0.36082 | −1.932 |  | 2.4627 |  | 12.0101 |
| RH7 | 1.1161 | 1.1161 | −0.59165 | −0.59165 | −1.3798 | −1.3798 | 2.0819 | 2.0819 | 14.788 |
| RH8 | 1.3663 | 1.3663 | −0.022792 |  | −1.5042 | −1.5042 | 1.7992 | 1.7992 | 9.5672 |
| RH9 | .82955 |  | −1.3055 |  | −1.5806 | −1.5806 | 2.3095 | 2.3095 | 20.2222 |
| RH10 | 1.6518 |  | −0.042043 | 0.042043 | −1.388 | −1.388 | 1.8641 | 1.8641 | 11.9734 |
| Mean | 1.232 | 1.2298 | −0.5297 | −0.4961 | −1.4546 | −1.4984 | 0.9867 | 1.9766 | 14.739 |
| SD | 0.2092 | 0.0892 | 0.4194 | 0.3196 | 0.3594 | 0.1829 | 0.2857 | 0.2229 | 4.7507 |
| Coef var | 0.1698 | 0.0725 | 0.7917 | 0.6443 | 0.2471 | 0.1221 | 0.1438 | 0.1133 | 0.3223 |
| LH11 | 1.4443 | 1.4443 | −0.38157 | −0.38157 | −1.2773 | −1.2773 | 1.5822 | 1.5822 | 15.9812 |
| LH12 | 1.5165 | 1.5165 | −0.40719 | −0.4.719 | −0.75933 | −0.75933 | 1.5381 | 1.5381 | 13.4771 |
| LH13 | .94823 |  | −0.90461 |  | −1.6843 |  | 1.9825 | 1.9825 | 17.6334 |
| LH14 | 1.2864 | 1.2864 | −0.71565 | −0.71565 | −1.1411 | −1.411 | 2.06 |  | 17.6471 |
| LH15 | 1.4382 | 1.4382 | −0.58282 | −0.58282 | −0.3704 | −0.3704 | 1.9812 | 1.9812 | 13.7858 |
| LH16 | 1.4118 | 1.4118 | −0.39302 | −0.39302 | −1.5575 | −1.5575 | 1.6768 | 1.6768 | 13.8736 |
| LH17 | 1.5916 | 1.5916 | −0.24714 | −0.24714 | −0.94846 | −0.94846 | 1.5831 | 1.5831 | 13.029 |
| LH18 | 1.655 | 1.655 | −0.11493 | −0.11493 | −0.74297 | −0.74297 | 1.5469 | 1.5469 | 10.9925 |
| LH19 | 1.686 | 1.686 | 0.10461 |  | −0.02371 |  | 1.5185 | 1.5185 | 14.0015 |
| LH20 | 1.8317 |  | 0.062897 | 0.062897 | −0.42992 | −0.42992 | 1.4456 |  | 12.6316 |
| Mean | 1.481 | 1.5037 | −0.3579 | −0.3474 | −0.8935 | −0.9034 | 1.6915 | 1.6762 | 14.3063 |
| SD | 0.2446 | 0.135 | 0.3239 | 0.2479 | 0.5337 | 0.4107 | 0.2269 | 0.1946 | 2.1521 |
| Coef var | 0.1652 | 0.0897 | 0.9048 | 0.7136 | 0.5973 | 0.4547 | 0.1341 | 0.1161 | 0.1504 |
| R-1 | −0.249 | −0.274 | −0.1718 | −0.1487 | −0.5611 | −0.595 | 0.2952 | 0.3004 | 0.4327 |
| (R-1)/min avg | −20% | −22% | 32% | 30% | 39% | 40% | 17% | 18% | 3% |
| R 1 | 0.8319 | 0.8138 | 1.4799 | 1.628 | 1.628 | 1.6586 | 1.1745 | 1.1792 | 1.0302 |
|  | $I_2$ (2) | $I_2$ (1) | $I_1$ (2) | $I_2$ (1) | $I_2$ (2) | $I_2$ (1) | $I_2$ (2) | $I_3$ (1) | |

TABLE 5-continued

|  |  |  |  |  |  |  |  |  |
|---|---|---|---|---|---|---|---|---|
| RH1 |  | 51.0222 | 51.0222 | 0.38106 | 0.38106 | 8.098 |  | 0.038298 |
| RH2 | 12.6984 | 53.869 | 53.869 | 0.30373 | 0.30373 | 10.6044 | 10.6044 | 0.038016 |
| RH3 | 16.5193 | 50.6936 | 50.6936 | 0.29748 | 0.29748 | 8.9082 | 8.9082 | 0.045505 |
| RH4 | 10.4053 | 53.7788 | 53.7788 | 0.30648 | 0.30648 | 11.0235 | 11.0235 | 0.048276 |
| RH5 | 14.2282 | 53.9597 | 53.9397 | 0.20716 |  | 13.9784 |  | 0.049109 |
| RH6 | 12.6101 | 52.086 | 52.086 | 0.72075 | 0.72075 | 10.5863 | 10.5863 | 0.050588 |
| RH7 | 14.788 | 55.4292 |  | 0.83008 |  | 11.0729 | 11.0729 | 0.049743 |
| RH8 |  | 52.8474 | 52.8474 | 0.64191 | 0.64191 | 10.7624 | 10.7624 | 0.054327 |
| RH9 | 20.2222 | 53.7778 | 53.7778 | 0.71368 | 0.71368 | 12.6562 | 12.6562 | 0.038887 |
| RH10 | 11.9734 | 46.5632 |  | 0.74962 | 0.74962 | 12.6003 | 12.6003 | 0.045247 |
| Mean | 14.1056 | 52.4027 | 52.7543 | 0.5152 | 0.5143 | 11.0291 | 11.0268 | 0.0458 |
| SD | 3.1244 | 2.5109 | 1.336 | 0.2358 | 0.2092 | 1.7433 | 1.199 | 0.0057 |
| Coef var | 0.2215 | 0.0479 | 0.0253 | 0.4577 | 0.4067 | 0.1581 | 0.1087 | 0.1246 |
| LH11 | 15.9812 | 50.2938 | 50.2938 | 0.56805 | 0.56805 | 13.5407 | 13.5407 | 0.038145 |
| LH12 | 13.4771 | 48.9218 | 48.9218 | 0.31959 |  | 10.6127 | 10.6127 | 0.037592 |
| LH13 | 17.6334 | 55.9165 |  | 0.37699 | 0.37699 | 10.3387 |  | 0.042021 |
| LH14 |  | 50.8824 | 50.8824 | 0.77406 | 0.77406 | 10.5926 | 10.5926 | 0.048177 |
| LH15 | 13.7858 | 48.0382 | 48.0382 | 0.56693 | 0.56693 | 12.1393 | 12.1393 | 0.044442 |
| LH16 | 13.8736 | 50.2747 | 50.2747 | 0.58609 | 0.58609 | 15.1891 | 15.1891 | 0.042006 |
| LH17 | 13.029 | 48.441 | 48.441 | 0.52291 | 0.52291 | 11.9951 | 11.9951 | 0.050465 |
| LH18 |  | 48.3458 | 48.3458 | 0.59228 | 0.59228 | 17.1123 | 17.1123 | 0.041822 |
| LH19 | 14.0115 | 50.4798 | 50.4798 | 0.85511 |  | 14.9071 | 14.9071 | 0.041647 |
| LH20 | 12.6316 | 45.7895 |  | 0.53129 | 0.53129 | 19.4151 |  | 0.045579 |
| Mean | 14.3029 | 49.7383 | 49.4597 | 0.5693 | 0.5648 | 13.5843 | 13.2611 | 0.0432 |
| SD | 1.6709 | 2.6541 | 1.1347 | 0.1589 | 0.109 | 3.0496 | 2.3401 | 0.0041 |
| Coef var | 0.1168 | 0.0534 | 0.0229 | 0.02792 | 0.193 | 0.2245 | 0.1765 | 0.0942 |
| R-1 | -0.1973 | 2.6643 | 3.2946 | -0.0541 | -0.0505 | -2.5552 | -2.2343 | 0.0026 |
| (R-1)/min avg | -1% | 5% | 7% | -11% | -10% | -23% | -20% | 6% |
| R 1 | 0.9862 | 1.0536 | 1.0666 | 0.9049 | 0.9106 | 0.8119 | 0.8315 | 1.0604 |

TABLE 6

| $I_9$ (2) | R hemi-pr | R hemi-pr | L hemi-pr | L hemi-pr | R/L hemi-pr | R/L hemi-pr | R-1 hemi-pr | R-1 hemi-pr | $L_9$ (1) | $L_9$ (2) |
|---|---|---|---|---|---|---|---|---|---|---|
| 0.038298 | 52.0065 |  | 46.6814 |  | 1.1141 |  | 6.2649 |  | .73242 | 0.73242 |
|  | 64.5163 | 64.5163 | 55.1889 | 55.1889 | 1.169 | 1.169 | 9.9227 | 9.9227 | .64453 |  |
| 0.045505 | 76.9135 | 76.1935 | 63.7189 | 63.7189 | 1.2071 | 1.2071 | 14.1878 | 14.1878 | .89355 | 0.89355 |
| 0.048276 | 95.8088 | 95.8088 | 76.1316 | 76.1316 | 1.2585 |  | 18.5634 | 18.5634 | .99609 | 0.99609 |
| 0.049109 | 99.1634 | 99.1634 | 79.9005 | 79.9005 | 1.2411 | 1.2411 | 17.8361 | 17.8361 | 1.1865 |  |
| 0.050588 | 99.6287 | 99.6287 | 80.3297 | 80.3297 | 1.2402 | 1.2402 | 19.203 |  | 1.0254 | 1.0254 |
| 0.049743 | 103.9507 | 103.9507 | 88.9418 | 88.9418 | 1.1687 | 1.1687 | 12.6125 | 12.6125 | .65918 | 0.65918 |
|  | 121.2796 | 121.2796 | 103.8818 | 103.8818 | 1.1675 | 1.1675 | 14.2604 | 14.2604 | .99609 | 0.99609 |
| 0.038887 | 110.1692 | 110.1692 | 92.0322 | 92.0322 | 1.1971 | 1.1971 | 12.8632 | 12.8632 | 1.0547 | 1.0547 |
| 0.045247 | 122.4027 |  | 104.4259 |  | 1.1733 | 1.1733 | 16.2855 | 16.2855 | .68848 | 0.68848 |
| 0.0457 | 94.5839 | 96.4288 | 79.1133 | 80.0157 | 1.1937 | 1.1955 | 14.1999 | 14.5664 | 0.8877 | 0.8807 |
| 0.0848 | 23.3196 | 18.0487 | 19.3931 | 15.5417 | 0.0441 | 0.0314 | 4.0444 | 2.882 | 0.1929 | 0.163 |
| 0.1016 | 0.2465 | 0.1872 | 0.2451 | 0.1942 | 0.0369 | 0.0263 | 0.2848 | 0.1979 | 0.2173 | 0.1851 |
| 0.038145 | 72.5222 |  | 53.9127 |  | 1.3452 |  | 15.7708 | 15.7708 | 1.04 | 1.04 |
|  | 76.3246 | 76.3246 | 59.6489 | 59.6489 | 1.2796 | 1.2796 | 16.3487 | 16.3487 | .64453 | 0.64453 |
| 0.042021 | 76.4277 | 76.4277 | 62.4038 | 62.4038 | 1.2247 | 1.2247 | 16.4023 | 16.4023 | .55664 |  |
| 0.048177 | 83.76 | 83.76 | 80.8509 | 80.8509 | 1.036 |  | 2.238 |  | .81299 | 0.81299 |
| 0.044442 | 96.7673 | 96.7673 | 79.8378 | 79.8378 | 1.212 | 1.212 | 15.3905 | 15.3905 | .98145 | 0.98145 |
| 0.042006 | 118.085 | 118.085 | 94.5711 | 94.5711 | 1.2486 | 1.2486 | 17.5477 | 17.5477 | 1.2012 | 1.2012 |
|  | 128.5904 | 128.5904 | 110.7784 | 110.7784 | 1.1608 | 1.1608 | 15.095 | 15.095 | .64453 | 0.64453 |
| 0.041822 | 128.3619 | 128.3619 | 102.0986 | 102.0986 | 1.2573 | 1.2573 | 19.4558 |  | .68848 | .68848 |
| 0.041647 | 138.5198 | 138.5198 | 116.0474 | 116.0474 | 1.1936 | 1.1936 | 12.6962 | 12.6962 | 3.3105 |  |
| 0.045579 | 153.1476 |  | 125.2732 |  | 1.225 | 1.225 | 15.6597 | 15.6597 | 1.1865 | 1.1865 |
| 0.043 | 107.2509 | 105.8548 | 88.5423 | 88.2796 | 1.218 | 1.2249 | 14.6605 | 15.6138 | 1.1067 | 0.9 |
| 0.003 | 29.5843 | 25.492 | 25.1052 | 21.1239 | 0.0813 | 0.0375 | 4.6945 | 1.402 | 0.8085 | 0.2336 |
| 0.0705 | 0.2758 | 0.2408 | 0.2835 | 0.2393 | 0.0668 | 0.0306 | 0.3202 | 0.0898 | 0.7306 | 0.2595 |
| 0.0027 | -12.6669 | -9.4261 | -9.429 | -8.2639 | -0.0244 | -0.0294 | -0.4605 | -1.0474 | -0.219 | -0.0192 |
| 6% | -13% | -10% | -12% | -10% | -2% | -2% | -3% | -7% | -25% | -2% |
| 1.0634 | 0.8819 | 0.911 | 0.8935 | 0.9064 | 0.98 | 0.976 | 0.9686 | 0.9329 | 0.8021 | 0.9786 |

| $I_{10}$ (1) | $I_{10}$ (2) | $I_{11}$ (1) | $I_{11}$ (2) | $I_{12}$ (1) | $I_{12}$ (2) | Pressure Freq |
|---|---|---|---|---|---|---|
| 0.0019174 |  | 0.71045 | 0.71045 | 0.0098593 | 0.0098593 | 3.3325 |
| 0.0088205 | 0.008205 | 0.65186 | 0.63186 | 0.0076059 | 0.0076059 | 5.2881 |
| 0.0057855 | 0.0057855 | 0.68848 | 0.68848 | 0.0042904 | 0.0042904 | 0.5127 |
| 0.0076752 | 0.0076752 | 0.55664 |  | 0.0047153 | 0.047153 | 5.4199 |
| 0.0081621 | 0.0081621 | 0.62988 | 0.62988 | 0.0053581 | 0.0053581 | 0.54199 |
| 0.0048277 |  | 1.1719 | 1.1719 | 0.0025282 |  | 0.55664 |

TABLE 6-continued

| | | | | | | |
|---|---|---|---|---|---|---|
| 0.0073768 | 0.0073768 | 0.99609 | 0.99609 | 0.0059338 | 0.059338 | 0.38086 |
| 0.012387 | 0.012387 | 1.0547 | 1.0547 | 0.0072785 | 0.0072785 | 0.46875 |
| 0.0053825 | 0.0053825 | 1.1133 | 1.1133 | 0.0046343 | 0.0046341 | 5.5957 |
| 0.0076754 | 0.0076754 | 3.9111 | | 0.01191 | | 4.3506 |
| 0.0009 | 0.0008 | 1.1484 | 0.8771 | 0.0016 | 0.0006 | 2.6448 |
| 0.0004 | 0.0002 | 0.9964 | 0.2279 | 0.0033 | 0.0002 | 2.3563 |
| 0.4861 | 0.2714 | 0.8676 | 0.2598 | 2.0415 | 0.308 | 0.8909 |
| 0.0078855 | 0.0078855 | 4.0723 | 4.0723 | 0.011312 | 0.011312 | 5.1855 |
| 0.0094965 | 0.0094965 | 4.8193 | 4.8193 | 0.010443 | 0.010443 | 0.46875 |
| 0.0053134 | 0.0053134 | .64453 | | 0.007945 | .0007945 | 0.57129 |
| 0.0056247 | 0.0056247 | 3.4937 | 3.4937 | 0.012812 | | 0.39551 |
| 0.0079653 | 0.0079653 | 0.68848 | 0.68848 | 0.0056112 | .00056112 | 0.39551 |
| 0.0027589 | | 5.1562 | | 0.011253 | 0.011253 | 0.4248 |
| 0.013553 | .0013553 | 4.8779 | 4.8779 | 0.011633 | 0.11663 | 0.62988 |
| 0.0046506 | 0.0046506 | 0.99609 | 0.99609 | 0.0052555 | | 0.4541 |
| 0.011848 | | 1.1792 | 1.1792 | 0.0057202 | 0.0057202 | 0.28564 |
| 0.0062246 | 0.0062246 | 4.8486 | 4.8486 | 0.098915 | 0.098915 | 0.35156 |
| 0.0018 | 0.0008 | 3.0776 | 3.1219 | 0.007 | 0.0071 | 0.9163 |
| 0.0035 | 0.0003 | 1.9567 | 1.8594 | 0.0055 | 0.0053 | 1.5034 |
| 1.9434 | 0.3825 | 0.6358 | 0.5956 | 0.7925 | 0.7567 | 1.6408 |
| −0.0009 | 0 | −1.9292 | −2.2449 | −0.0053 | −0.0064 | 1.7285 |
| −108% | 4% | −168% | −256% | −328% | −1036% | 189% |
| 0.4796 | 1.042 | 0.3732 | 0.2809 | 0.2337 | 0.0088 | 2.8865 |

TABLE 7

| Pressure Freq | Pressure Power | Pressure Power | Speed peak | Speed peak | Speed mean | Speed mean | Speed mean s | Speed mean s |
|---|---|---|---|---|---|---|---|---|
| 3.3325 | 0.096296 | | 8.3495 | | 4.0833 | | 0.007768 | |
| 5.2881 | 0.061731 | 0.061731 | 9.5933 | 9.5933 | 4.8141 | 4.8141 | 0.057164 | 0.057164 |
| 0.5127 | 0.0044982 | | 12.2647 | 12.2647 | 6.1768 | 6.1768 | 0.050443 | 0.050443 |
| 5.44199 | 0.05208 | 0.05208 | 11.6228 | 11.6228 | 5.8715 | 5.8715 | 0.12527 | 0.12527 |
| 0.54199 | 0.027901 | 0.027901 | 15.0426 | | 6.0457 | 6.0457 | 0.1517 | 0.1517 |
| 0.55664 | 0.0082316 | 0.0082316 | 13.3404 | 13.3404 | 6.012 | 6.012 | 0.16833 | 0.16833 |
| | 0.0052711 | 0.0052711 | 10.7915 | 10.7915 | 5.2681 | 5.2681 | 0.094529 | 0.094529 |
| 0.46875 | 0.012483 | 0.012483 | 14.1176 | 14.1176 | 6.1778 | | 0.17908 | |
| | 0.058576 | 0.058576 | 10.161 | 10.161 | 5.2236 | 5.2236 | 0.13968 | 0.13968 |
| 4.3506 | 0.05491 | 0.05491 | 10.8455 | 10.8455 | 5.2258 | 5.2258 | 0.059048 | 0.059048 |
| 2.5589 | 0.0382 | 0.0351 | 11.6129 | 11.5921 | 5.4899 | 5.5797 | 0.1033 | 0.1058 |
| 2.2762 | 0.0311 | 0.0242 | 2.0962 | 1.5643 | 0.691 | 0.5044 | 0.0579 | 0.0467 |
| 0.8872 | 0.814 | 0.6889 | 0.1805 | 0.1349 | 0.1259 | 0.0904 | 0.5608 | 0.4418 |
| | 0.061452 | | 9.9972 | | 6.1496 | | 0.17253 | 0.17253 |
| 0.86875 | 0.0094384 | 0.0094384 | 10.7797 | 10.7797 | 5.3819 | 5.3819 | 0.10134 | 0.10134 |
| 0.57129 | 0.0073217 | 0.0073217 | 11.0506 | 11.0506 | 5.5366 | 5.5366 | 0.17892 | 0.17892 |
| 0.39551 | 0.0051118 | | 10.7443 | 10.7443 | 4.9679 | 4.9679 | 0.19278 | 0.19278 |
| 0.39551 | 0.0077278 | 0.6077278 | 10.1037 | 10.1037 | 5.272 | 5.272 | −0.02886 | |
| 0.4248 | 0.02284 | 0.02284 | 12.7809 | | 5.4773 | 5.4773 | 0.22708 | |
| 0.62906 | 0.0082204 | 0.0082204 | 12.735 | 12.735 | 5.5803 | 5.5803 | 0.061202 | 0.061202 |
| 0.4541 | 0.012612 | 0.012612 | 10.1842 | 10.1842 | 5.0876 | 5.0876 | 0.10128 | 0.10128 |
| | 0.015209 | 0.015209 | 11.3279 | 11.3279 | 4.204 | | 0.062106 | .0062106 |
| 0.35156 | 0.025622 | 0.025622 | 11.4363 | 11.4363 | 4.903 | 4.903 | 0.020919 | 0.020919 |
| 0.4614 | 0.0176 | 0.0136 | 11.114 | 11.0452 | 5.256 | 5.2758 | 0.1033 | 0.1044 |
| 0.0945 | 0.0169 | 0.0071 | 0.9967 | 0.8347 | 0.5153 | 0.2623 | 0.0877 | 0.0722 |
| 0.205 | 0.9605 | 0.5217 | 0.0897 | 0.0756 | 0.098 | 0.0497 | 0.8491 | 0.6917 |
| 2.0975 | 0.0206 | 0.0215 | 0.4989 | 0.5469 | 0.2338 | 0.3039 | 0 | 0.0014 |
| 455% | 118% | 158% | 4% | 5% | 4% | 6% | 0% | 1% |
| 5.5456 | 2.1758 | 2.5799 | 1.0449 | 1.0495 | 1.0445 | 1.0576 | 0.9996 | 1.0132 |

| $I_{13}$ (1) | $I_{13}$ (2) | $I_{14}$ (1) | $I_{14}$ (2) | $I_{15}$ (1) | $I_{15}$ (2) | $I_{16}$ (1) | $I_{16}$ (2) |
|---|---|---|---|---|---|---|---|
| 0.21973 | 0.21973 | 0.051075 | 1.1133 | 1.1133 | 2.88106 | | |
| 0.50537 | 0.50537 | 0.047243 | | 0.65918 | 0.63918 | 1.39E.05 | 1.39E.05 |
| 0.4834 | 0.4834 | 0.19419 | 0.19419 | 0.74707 | 0.74707 | 8.73E.06 | 8.73E.06 |
| 0.9668 | | 0.076818 | 0.076818 | 0.71777 | 0.71777 | 2.56E.05 | 2.56E.05 |
| 0.54199 | 0.54199 | 0.26958 | | 0.38086 | 0.38086 | 1.13E.05 | 1.13E.05 |
| 0.11719 | | 0.14149 | 0.14149 | 1.0986 | 1.0986 | 5.90E.05 | |
| 0.36621 | 0.36621 | 0.25658 | 0.25658 | 0.82031 | 0.82031 | 1.08E.05 | 1.08E.05 |
| 0.4541 | 0.4541 | 0.22589 | 0.22589 | 0.80566 | 0.80566 | 1.08E.05 | 1.08E.05 |
| 0.41016 | 0.41016 | 0.086152 | 0.086152 | 0.10254 | | 1.76E.05 | 1.76E.05 |
| 0.32227 | 0.32227 | 0.1218 | 0.1218 | 1.1372 | | 2.05E.05 | 2.05E.05 |
| 0.4387 | 0.4129 | 0.1471 | 0.1442 | 0.7603 | 0.7928 | 0 | 0 |
| 0.2278 | 0.1066 | 0.0843 | 0.0745 | 0.3318 | 0.2368 | 0 | 0 |
| 0.5193 | 0.2583 | 0.573 | 0.5167 | 0.4365 | 0.2986 | 0.8231 | 0.3591 |
| 0.39551 | 0.39551 | 0.045468 | 0.045468 | 0.64453 | 0.64453 | 1.08E.05 | |
| 0.27832 | 0.27832 | 0.11044 | 0.11044 | 0.82031 | 0.82031 | 3.06E.05 | 3.03E.05 |

TABLE 7-continued

| | | | | | | | |
|---|---|---|---|---|---|---|---|
| 0.35156 | 0.35156 | 0.088712 | 0.088712 | 1.0693 | | 1.51E.05 | 1.51E.05 |
| 1.1719 | | 0.09231 | 0.09321 | 0.32959 | | 5.31E.05 | |
| 0.13184 | | 0.044955 | | 0.83496 | 0.83496 | 1.34E.05 | 1.34E.05 |
| 0.41016 | 0.41016 | 0.069383 | 0.069383 | 0.76172 | 0.76172 | 2.03E.05 | 2.03E.05 |
| 0.16113 | 0.16113 | 0.11091 | | 0.33691 | 0.33691 | 2.03E.05 | 2.03E.05 |
| 0.38086 | 0.38086 | 0.0719 | 0.0719 | 0.67383 | 0.67383 | 2.27E.05 | 2.27E.05 |
| 0.16113 | 0.16113 | 0.059927 | 0.059927 | 0.37354 | 0.37354 | 1.12E.05 | 1.12E.05 |
| 0.32227 | 0.32227 | 0.081702 | 0.081702 | 0.68848 | 0.68848 | 2.17E.05 | 2.17E.05 |
| 0.3765 | 0.3076 | 0.0776 | 0.0775 | 0.6533 | 0.6418 | 0 | 0 |
| 0.2981 | 0.0997 | 0.0237 | 0.0203 | 0.2428 | 0.1896 | 0 | 0 |
| 0.7919 | 0.324 | 0.3055 | 0.2618 | 0.3717 | 0.2955 | 0.5714 | 0.3177 |
| 0.0623 | 0.1053 | 0.0695 | 0.0668 | 0.1069 | 0.1511 | 0 | 0 |
| 17% | 34% | 90% | 86% | 16% | 24% | 16% | 23% |
| 1.1654 | 1.3423 | 1.8961 | 1.8618 | 1.1637 | 1.2354 | 0.8593 | 0.8146 |

Although the present invention has been described in connection with particular embodiments thereof, it is to be understood that various modifications, alterations and adaptions may be made by those skilled in the art without departing from the spirit and scope of the invention. It is intended that the invention be limited only by the appended claims.

Various publications are cited herein, the contents of which are hereby incorporated by reference in their entireties.

What is claimed is:

1. A system for clinically assessing motor function in a subject comprising:
   an electronic digitizing tablet having a writing device for obtaining a geometric pattern handwritten by the subject and providing one or more digital signals representing said pattern; and
   a microprocessor for processing said signals to derive one or more geometric indices representative of motor function and for computing from said indices, using an expert-generated standard of reference to select and assign weightings to said,indices a clinical rating score indicative of motor function.

2. The system according to claim 1, further comprising a display device for displaying said geometric indices and clinical ratings.

3. The system according to claim 1, where the geometric pattern is an Archimedes spiral and the geometric indices are spiral indices.

4. The system according to claim 3, further comprising a display device for displaying said spiral indices and clinical ratings.

5. The system according to claim 3, wherein said microprocessor comprises:
   means for computing a first order smoothness index;
   means for computing a second order smoothness index; and
   means for computing a second order zero-crossing rate index.

6. The system according to claim 5, wherein said microprocessor comprises means for computing said clinical rating score as a function of said first order smoothness index, said second order smoothness index, and said second order zero-crossing rate index.

7. A method for clinically assessing motor function in a subject comprising:
   obtaining a geometric pattern handwritten by the subject on a digitizing tablet;
   generating one or more signals representing said geometric pattern;
   processing said signals to derive one or more geometric indices representative of motor function; and
   computing from said geometric indices, using an expert-generated standard of reference to select and assign weightings to said indices, a clinical rating score indicative of motor function in the subject.

8. The method according to claim 7, where the geometric pattern is an Archimedes spiral.

9. The method according to claim 8, wherein said processing step comprises:
   computing a first order smoothness index;
   computing a second order smoothness index; and
   computing a second order zero-crossing rate index.

10. The method according to claim 9, wherein said step of computing the clinical rating comprises using said first order smoothness index, said second order smoothness index, and said second order zero-crossing rate index.

11. A method for diagnosing Parkinson's Disease in a subject comprising:
    obtaining a spiral drawn by the subject on a digitizing tablet;
    generating one or more digital signals representing the spiral;
    processing the signals to derive one or more geometric indices representative of motor function; and
    computing from the geometric indices, using an expert-generated standard of reference to select and assign weightings to said indices, a clinical rating score indicative of the diagnosis of Parkinson's Disease.

12. The method of claim 11, wherein the geometric indices are indices $I_1$–$I_{17}$ as set forth in Table 1.

13. The method of claim 12, where the clinical rating score is calculated using the equation:

$$0.4615*I_1+0.0544*I_5-0.2331*I_1^2-0.0726*I_2^2-0.001*I_5^2+0.2539*I_1*I_2+1.3668.$$

14. The method of claim 13, where a clinical rating score of at least one bears a positive correlation with the diagnosis of Parkinson's Disease.

15. A method for monitoring Parkinson's Disease in a subject comprising:
    (i) on a first occassion,
       (a) obtaining a spiral drawn by the subject on a digitizing tablet;
       (b) generating one or more digital signals representing the spiral;
       (c) processing the signals to derive one or more geometric indices representative of motor function; and (d) computing from the geometric indices, using an expert-generated standard of reference to select and assign weightings to said indices, a clinical rating score indicative of the diagnosis of Parkinson's Disease;

(ii) on a second occasion, separated from the first occasion by an interval of time, repeating steps (a)–(d); and (iii) comparing the clinical rating scores obtained at the first occasion and the second occasion, where an increase in the score has a positive correlation with a worsening of motor function and a decrease in the score has a positive correlation with an improvement in motor function.

16. The method of claim 15, wherein the geometric indices are indices $I_1$–$I_{17}$ as set forth in Table 1.

17. The method of claim 16, where the clinical rating score is calculated using the equation:

$$0.4615*I_1 + 0.0544*I_5 - 0.2331*I_1^2 - 0.0726*I_2^2 - 0.001*I_5^2$$
$$+ 0.2539*I_1*I_2 + 1.3668.$$

\* \* \* \* \*